United States Patent [19]

Piwinski et al.

[11] Patent Number: 5,151,423

[45] Date of Patent: Sep. 29, 1992

[54] HETEROCYCLIC N-OXIDE DERIVATIVES OF SUBSTITUTED BENZO[5,6]CYCLOHEPTAPYRIDINES, COMPOSITIONS AND METHODS OF USE

[75] Inventors: John J. Piwinski, Parsippany; Michael J. Green, Skillman; Jesse Wong, Union, all of N.J.

[73] Assignee: Schering Corporation, Kenilworth, N.J.

[21] Appl. No.: 625,261

[22] Filed: Dec. 10, 1990

Related U.S. Application Data

[63] Continuation-in-part of Ser. No. 345,604, May 1, 1989, Pat. No. 5,089,496.

[30] Foreign Application Priority Data

Apr. 30, 1990 [EP] European Pat. Off. ........ 90108225.5

[51] Int. Cl.$^5$ ............... A61K 31/495; A61K 31/50; C07D 401/04; C07D 221/06
[52] U.S. Cl. .................... 514/254; 514/253; 514/269; 514/275; 514/256; 514/290; 544/295; 544/298; 544/238; 544/322; 544/333; 544/361; 544/405; 546/93
[58] Field of Search ............... 546/202, 203, 187, 196, 546/93; 544/295, 298, 238, 322, 333, 361, 405; 514/253, 254, 269, 275, 256, 290

[56] References Cited

U.S. PATENT DOCUMENTS

| | | | |
|---|---|---|---|
| 3,326,924 | 6/1967 | Villani | 260/293 |
| 3,357,986 | 12/1967 | Villani | 260/293 |
| 3,409,621 | 11/1968 | Villani | 514/290 |
| 3,419,565 | 12/1968 | Villani | 260/294 |
| 3,682,930 | 8/1972 | Bourquin et al. | 260/293 |
| 3,717,647 | 2/1973 | Villani | 260/294 |
| 3,749,786 | 7/1973 | Bourquin et al. | 424/267 |
| 3,960,894 | 6/1976 | Bourquin et al. | 260/332 |
| 4,128,549 | 12/1978 | Bourquin et al. | 546/202 |
| 4,282,233 | 8/1981 | Villani | 424/267 |
| 4,355,036 | 10/1982 | Villani | 424/267 |
| 4,356,184 | 10/1982 | Deason et al. | |
| 4,609,664 | 9/1986 | Hasspacher | 514/324 |
| 4,616,023 | 10/1986 | Remy et al. | 514/323 |
| 4,659,716 | 4/1987 | Villani et al. | 514/290 |

FOREIGN PATENT DOCUMENTS

| | | |
|---|---|---|
| 47226 | 9/1980 | European Pat. Off. . |
| 42544 | 10/1984 | European Pat. Off. . |
| 0152897 | 8/1985 | European Pat. Off. . |
| 0341860 | 11/1989 | European Pat. Off. . |
| 1470314 | 4/1964 | Fed. Rep. of Germany . |

OTHER PUBLICATIONS

Villani et al. "Derivatives of 10, 11-Dihydro-5H-Dibenzo [a,b] Cycloheptene . . . ", J. Med. Chem. vol. 15, No. 7, pp. 750-754 (1972).
Villani et al., "N-Substituted 11-(-4-Piperidylidene)-5,6-Dihydro-11H-Benzo(5,6)Cyclohepta (1,2-b)Pyridines", Arzneimittel-Forschung/-Drug Research, vol. 36 (II), No. 9, 1311-1314 (1986).
Maurer et al., *J. Chromatogr.*, 382, (1986), 147-165.
Maurer et al., *J. Chromatogr.*, 430, (1988), 31-41.
Maurer et al., *J. Clin. Chem. Clin. Biochem.*, 25, No. 9, 620, 1987 with translation.

*Primary Examiner*—Cecilia Tsang
*Attorney, Agent, or Firm*—James R. Nelson

[57] ABSTRACT

Heterocyclic N-oxide derivatives of substituted benzo[5,6]cycloheptapyridines, and pharmaceutically acceptable salts and solvates thereof are disclosed, which possess anti-allergic and anti-inflammatory activity. Methods for preparing and using the compounds are also described.

31 Claims, No Drawings

HETEROCYCLIC N-OXIDE DERIVATIVES OF SUBSTITUTED BENZO[5,6]CYCLOHEPTAPYRIDINES, COMPOSITIONS AND METHODS OF USE

The present application is a continuation-in-part of U.S. application Ser. No. 345,604, filed May 1, 1989, now U.S. Pat. No. 5,089,496 the benefit of which is claimed under 35 U.S.C. 120.

BACKGROUND OF THE INVENTION

The present invention relates to heterocyclic N-oxide derivatives of substituted benzo[5,6]cycloheptapyridines and to pharmaceutical compositions and methods of using such compounds.

U.S. Pat. Nos. 3,326,924, 3,717,647 and 4,282,233, European published Application No. 0042544 and Villani et al., *Journal of Medicinal Chemistry*, Vol. 15, No. 7, pp 750–754 (1972) and *Arzn. Forch* 36 1311–1314 (1986) describe certain 11-(4-piperidylidene)-5H-benzo[5,6]cyclohepta[1,2-b]pyridines as antihistamines. U.S. Pat. No. 4,355,036 describes certain N-substituted piperidylidene compounds.

WO 88/03138 discloses compounds of the formula

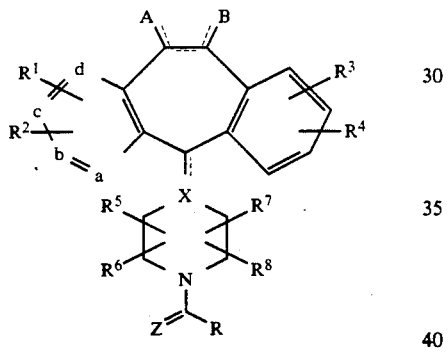

or a pharmaceutically acceptable salt or solvate thereof, wherein:

- one of a, b, c and d represents N or NR$^9$ where R$^9$ is O, —CH$_3$ or —(CH$_2$)$_n$CO$_2$H where n is 1 to 3, and the remaining a, b, c and d groups are CH, which remaining a, b, c and d groups optionally may be substituted with R$^1$ or R$^2$;
- R$^1$ and R$^2$ may be the same or different and each independently represents halo, —CF$_3$, —OR$^{10}$, —COR$^{10}$, —SR$^{10}$, —N(R$^{10}$)$_2$, —NO$_2$, —OC(O)R$^{10}$, —CO$_2$R$^{10}$, —OCO$_2$R$^{11}$, alkynyl, alkenyl or alkyl, which alkyl or alkenyl group may be substituted with halo, —OR$^{10}$ or —CO$_2$R$^{10}$;
- R$^3$ and R$^4$ may be the same or different and each independently represents H, any of the substituents of R$^1$ and R$^2$, or R$^3$ and R$^4$ together may represent a saturated or unsaturated fused C$_5$-C$_7$ ring;
- R$^5$, R$^6$, R$^7$ and R$^8$ each independently represent H, —CF$_3$, alkyl or aryl, which alkyl or aryl may be substituted with —OR$^{10}$, —SR$^{10}$, —N(R$^{10}$)$_2$, —NO$_2$, —COR$^{10}$, —OCOR$^{10}$, —OCO$_2$R$^{11}$, —CO$_2$R$^{10}$, —OPO$_3$R$^{10}$ or one of R$^5$, R$^6$, R$^7$ and R$^8$ may be taken in combination with R as defined below to represent —(CH$_2$)$_r$— where r is 1 to 4 which may be substituted with lower alkyl, lower alkoxy, —CF$_3$ or aryl;
- R$^{10}$ represents H, alkyl or aryl;
- R$^{11}$ represents alkyl or aryl;
- X represents N or C, which C may contain an optional double bond to carbon atom 11;
- the dotted line between carbon atoms 5 and 6 represents an optional double bond, such that when a double bond is present, A and B independently represent H, —R$^{10}$, —OR$^{11}$ or —OC(O)R$^{10}$, and when no double bond is present between carbon atoms 5 and 6, A and B each independently represent H$_2$, —(OR$^{10}$)$_2$, alkyl and H, (alkyl)$_2$, —H and —OC(O)R$^{10}$, H and —OR$^{10}$, =O, aryl and H, =NOR$^{10}$ or —O—(CH$_2$)$_p$—O— where p is 2, 3 or 4 and R$^{10}$ is as previously defined;
- Z represents O, S or H$_2$ such that
  - (a) when Z is O, R may be taken in combination with R$^5$, R$^6$, R$^7$ or R$^8$ as defined above, or R represents H, aryl, alkyl, —SR$^{11}$, —N(R$^{10}$)$_2$, cycloalkyl, alkenyl, alkynyl or —D wherein —D represents heterocycloalkyl,

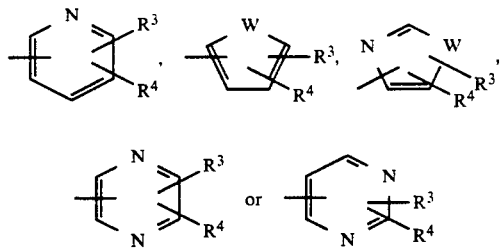

wherein R$^3$ and R$^4$ are as previously defined and W is O, S or NR$^{10}$ wherein R$^{10}$ is as defined above, said cycloalkyl, alkyl, alkenyl and alkynyl being optionally substituted with from 1–3 groups selected from halo, —CON(R$^{10}$)$_2$, aryl, —CO$_2$R$^{10}$, —OR$^{12}$, —SR$^{12}$, —N(R$^{10}$)$_2$, —N(R$^{10}$)CO$_2$R$^{10}$, —COR$^{12}$, —NO$_2$ or —D, wherein —D and R$^{10}$ are as defined above and R$^{12}$ represents R$^{10}$, —(CH$_2$)$_m$OR$^{10}$ or —(CH$_2$)$_q$CO$_2$R$^{10}$ wherein R$^{10}$ is as previously defined, m is 1 to 4 and q is 0 to 4, said alkenyl and alkynyl R groups not containing —OH, —SH or —N(R$^{10}$)$_2$ on a carbon containing a double or triple bond respectively;

- (b) when Z represents S, R represents in addition to those R groups above, aryloxy or alkoxy; and
  - (c) when Z represents H$_2$, R represents —COOR$^{10}$, —E—COOR$^{10}$ or —E—OR$^{12}$ where E is alkanediyl which may be substituted with —OR$^{10}$, —SR$^{10}$, —N(R$^{10}$)$_2$ or —D where D, R$^{10}$ and R$^{12}$ are as previously defined. These compounds are disclosed as being useful in the treatment of allergy and inflammation.

SUMMARY OF THE INVENTION

We have now surprisingly found that N-oxide compounds having the structural formula I below possess both potent antihistaminic and PAF antagonistic activities:

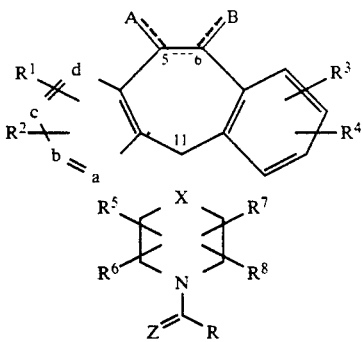

or a pharmaceutically acceptable salt or solvate thereof, wherein:

R represents an N-oxide heterocyclic group of the formula (i), (ii), (iii) or (iv)

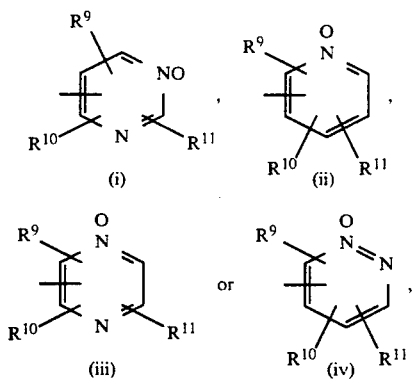

or R represents an alkyl group substituted with a heterocyclic N-oxide group of the formula (i), (ii), (iii) or (iv) above;

one of a, b, c and d represents N or $NR^{12}$ where $R^{12}$ is O, $-CH_3$ or $-(CH_2)_nCO_2H$ where n is 1 to 3, and the remaining a, b, c and d groups are CH, which remaining a, b, c and d groups optionally may be substituted with $R^1$ or $R^2$;

$R^1$ and $R^2$ may be the same or different and each independently represents halo; $-CF_3$, $-OR^{13}$, $-COR^{13}$, $-SR^{13}$, $-S(O)_eR^{14}$ where e is 1 or 2, $-N(R^{13})_2$, $-NO_2$, $-OC(O)R^{13}$, $-CO_2R^{13}$, $-OCO_2R^{14}$, $-CN$, $-NR^{13}OC(O)R^{13}$, alkynyl, alkenyl or alkyl, which alkyl group may be substituted with halo, $-OR^{13}$ or $-CO_2R^{13}$ and which alkenyl group may be substituted with halo, $-OR^{14}$ or $-CO_2R^{13}$;

$R^3$ and $R^4$ may be the same or different and each independently represents H or any of the substituents of $R^1$ and $R^2$, or $R^3$ and $R^4$ together may represent a saturated or unsaturated $C_5$-$C_7$ carbocyclic ring fused to the benzene ring;

$R^5$, $R^6$, $R^7$ and $R^8$ each independently represent H, $-CF_3$, alkyl or aryl, which alkyl or aryl may be substituted with $-OR^{13}$, $-SR^{13}$, or $-N(R^{13})_2$; in addition, $R^5$ may be combined with $R^6$ to represent =O or =S and/or $R^7$ may be combined with $R^8$ to represent =O or =S;

$R^9$, $R^{10}$, and $R^{11}$ may be the same or different and each is independently selected from H, halo, $-CF_3$, $-OR^{13}$, $-C(O)R^{13}$, $-SR^{13}$, $-S(O)_eR^{14}$ where e is 1 or 2, $-N(R^{13})_2$, $-NO_2$, $-CO_2R^{13}$, $-OCO_2R^{14}$, $-OCOR^{13}$, alkyl, aryl, alkenyl or alkynyl, which alkyl may be substituted with $-OR^{13}$, $-SR^{13}$ or $-N(R^{13})_2$ and which alkenyl may be substituted with $OR^{14}$ or $SR^{14}$;

$R^{13}$ represents H, alkyl or aryl;
$R^{14}$ represents alkyl or aryl;
$R^{15}$ represents H or alkyl;
X represents N, CH or C;

when X represents C, an optional double bond indicated by the dotted lines to carbon atom 11 is present, and when X is N or CH, the double bond is absent;

the dotted line between carbon atoms 5 and 6 represents an optional double bond, such that when a double bond is present, A and B each independently represent $-R^{13}$, halo, $-OR^{14}$, $-OC(O)R^{13}$ or $-OCO_2R^{14}$ and when no double bond is present between carbon atoms 5 and 6, A and B each independently represent $H_2$, $-(OR^{14})_2$, [H and halo], dihalo, [alkyl and H], (alkyl)$_2$, [—H and $-OC(O)R^{13}$], [H and $-OR^{13}$], =O, [aryl and H], =$NOR^{15}$ or $-O-(CH_2)_p-O-$ where p is 2, 3 or 4 and $R^{13}$ is as previously defined; and Z represents =O or =S.

Preferably, b, c and d are CH; a is N or $N^+-O^-$; $R^1$ and $R^2$ each independently represent H, alkyl (e.g., $CH_3$), OH or halo; the dotted lines between positions 5 and 6 are absent and A and B are both [H, H] or one of A or B is [H, OH] and the other represents [H, H] or the dotted line between positions 5 and 6 is present and A and B are both H; $R^3$ and $R^4$ each independently represent H, halo or alkyl, most preferably halo, e.g., chloro in the 8-position; $R^5$, $R^6$, $R^7$, and $R^8$ each represent H; and X represents C and the dotted line drawn to X represents a double bond or X represents N and the dotted line is absent.

In another embodiment of the invention, when Z represents O in formula I, R represents an N-oxide heterocyclic group of the formula (ia), (iia), (iiia) or (iva):

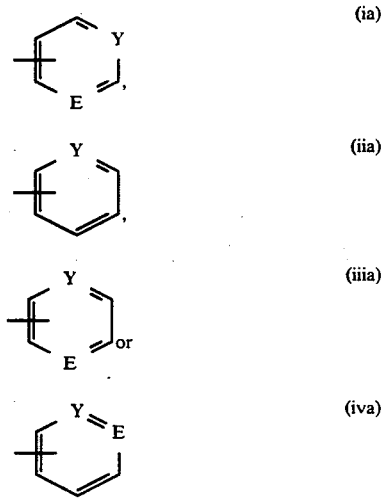

wherein Y represents $N^+-O^-$ and E represents $N^+-O^-$ or N, or R represents an alkyl group substituted with one of said N-oxide heterocyclic groups (ia), (iia), (iiia) or (iva). In this embodiment, the definitions of a, b, c, d, A, B, $R^1$, $R^2$, $R^3$, $R^4$, $R^5$, $R^6$, $R^7$, $R^8$, X and the dotted lines are as set forth above for formula I. Preferably, in this embodiment, b, c and d are CH; a is N or N+—O−; R¹ and R² each independently represent H, alkyl (e.g., CH₃) or halo; the dotted lines between positions 5 and 6 are absent and A and B are both H, H or one of A or B is H,OH and the other represents H, H or the dotted line between positions 5 and 6 is present and A and B are both H; R³ and R⁴ each independently represent H, halo or alkyl, most preferably halo, e.g., chloro in the 8-position; R⁵, R⁶, R⁷, and R⁸ each represent H, or R⁵ and R⁶ or R⁷ and R⁸ together represent =O or =S; and X represents C and the dotted line drawn to X represents a double bond or X represents N and the dotted line is absent.

Another embodiment of the invention involves compounds of the formula Ib:

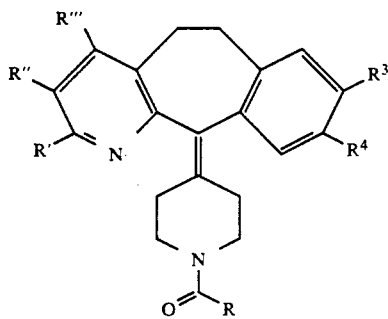

where at least one of R', R" and R"' is other than H and each independently represents halo, phenyl, substituted phenyl, hydroxy, mercapto, alkyl of 2 to 6 carbon atoms, alkyl—C(O)—, alkyl substituted with a hydroxy or CF₃; R³ and R⁴ are the same or different and are as defined above, preferably H or halo, e.g., chloro in the 8-position; and R in formula Ib represents a heterocyclic N-oxide group of the formula (ia), (iia), (iiia) or (iva) above, or alkyl substituted with a heterocyclic N-oxide group of the formula (ia), (iia), (iiia) or (iva) above.

A further preferred embodiment of the invention involves compounds of the formula Ic:

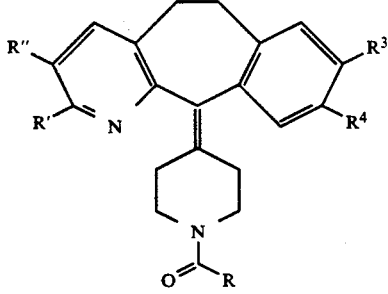

where R' and R" are independently H, halo, alkyl, OH or CF₃; R³ and R⁴ are the same or different and are as defined above, preferably H or halo, e.g., chloro in the 8-position; and R in formula Ic represents a heterocyclic N-oxide group of the formula (i), (ii), (iii) or (iv) above, or alkyl substituted with a heterocyclic N-oxide group of the formula (i), (ii), (iii) or (iv) above.

Preferably one or both of R³ and R⁴ in formula Ic is halo, e.g., chloro or fluoro. The most preferred value of R³ and/or R⁴ is a halogen located at carbon atom 8 and/or 9, as shown in the following numbered ring structure showing the tricyclic portion of the compounds of the invention:

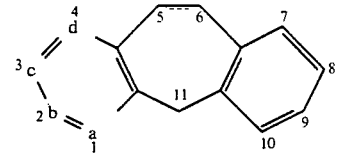

Compounds of the invention include:

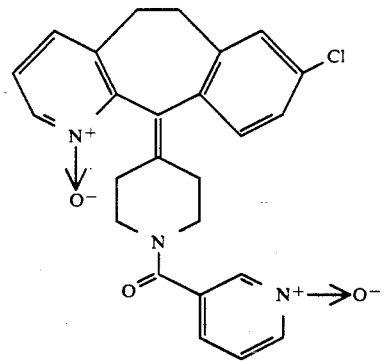

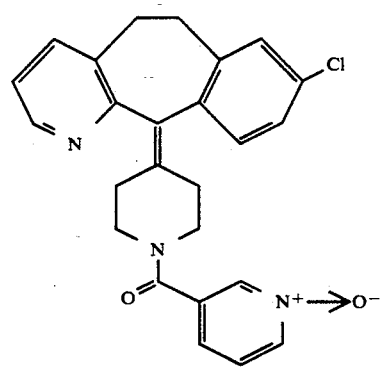

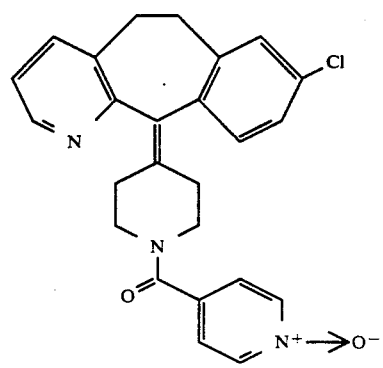

-continued
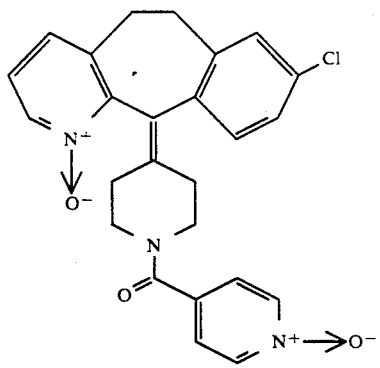
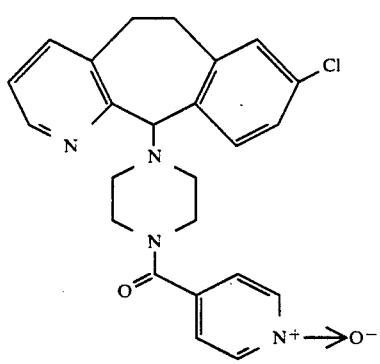
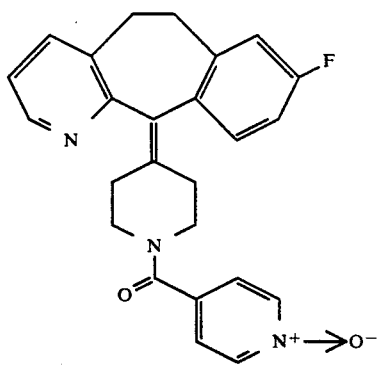
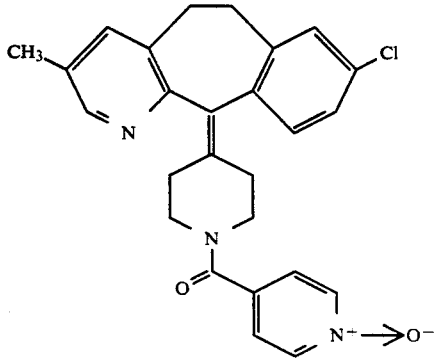
-continued
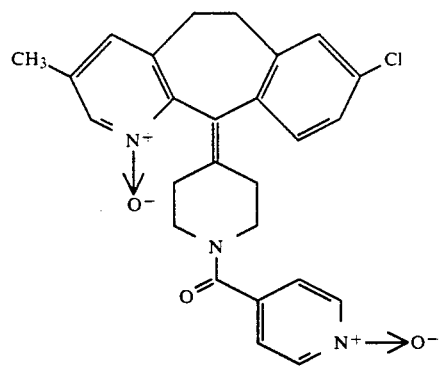
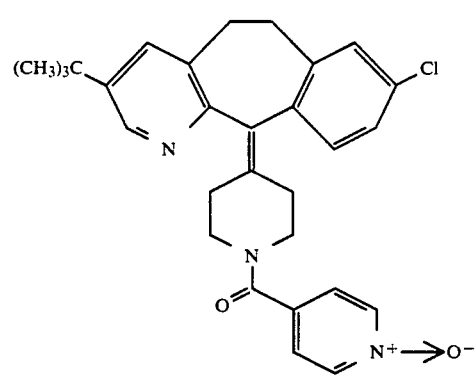
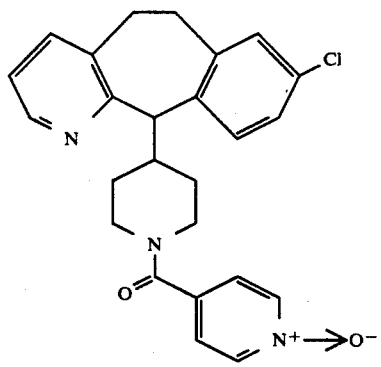
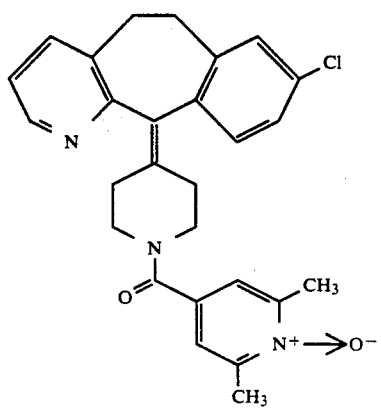

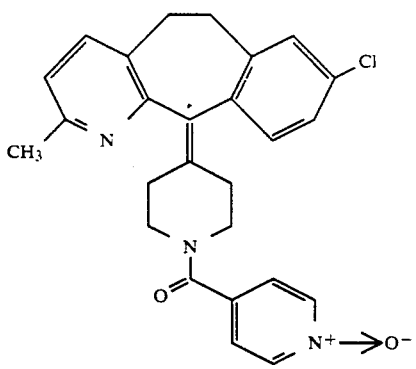

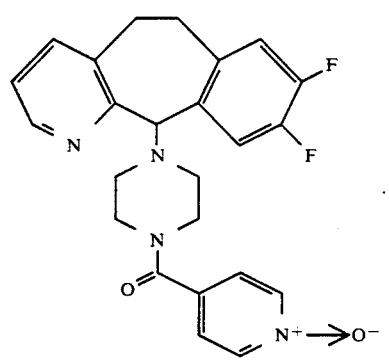

Particularly preferred compounds include:

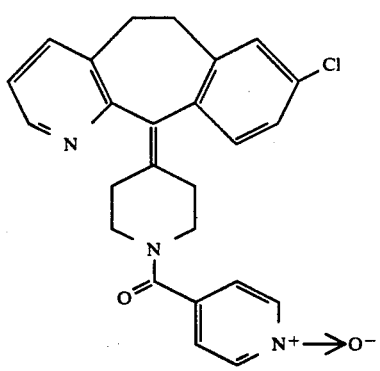

and

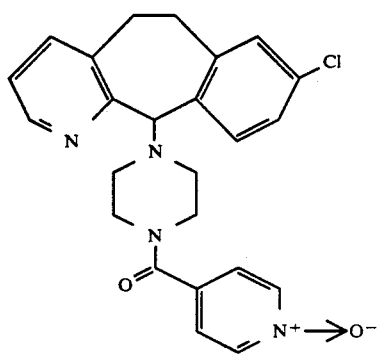

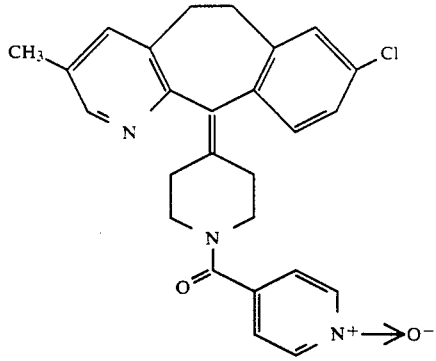

The invention also is directed at a process for producing a compound having structural formula I wherein the substituents are as previously defined by:

a) reacting a compound of formula II below with a compound of formula RCOOH in the presence of a coupling agent

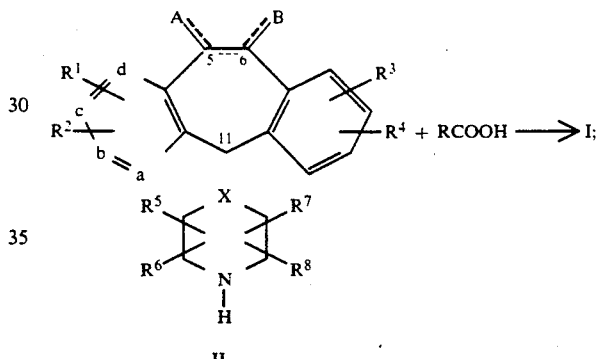

b) reacting a compound of formula II with a compound of formula III in the presence of base to produce compounds of structural formula I

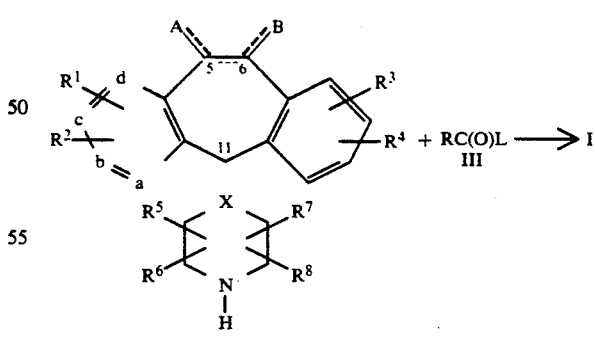

wherein L designates a leaving group such as halo, e.g., Cl; or c) a compound of formula IV can be reacted with an oxidizing agent such as meta-chloroperbenzoic acid (MCPBA) or hydrogen peroxide in acetic acid to form a compound of formula I

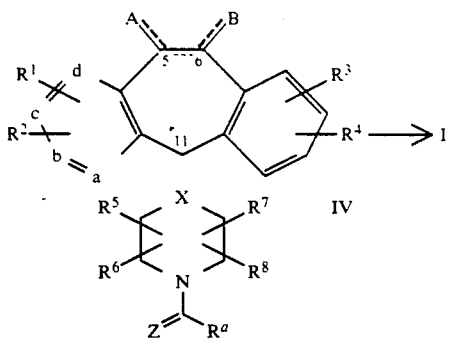

wherein $R^a$ represents

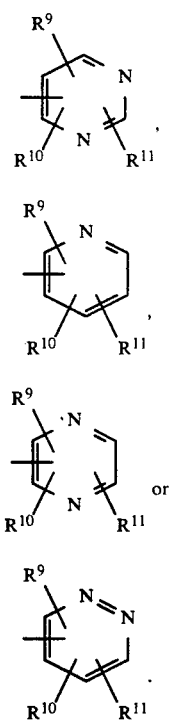

(Usually, oxidation of other basic amino groups in the molecules also occurs in this last process.)

The invention also encompasses a pharmaceutical composition which comprises a compound of formula I as defined above in combination with a pharmaceutically acceptable carrier.

The invention further encompasses a method of treating allergy or inflammation in a mammal, comprising administering a compound of formula I to said mammal in an amount effective to treat allergy or inflammation, respectively.

The invention also comprises a method for making a pharmaceutical composition comprising mixing a compound of formula I with a pharmaceutically acceptable carrier.

As used herein, the following terms are used as defined below unless otherwise indicated:

alkyl—(including the alkyl portions of alkoxy, alkylamino and dialkylamino)—represents straight and branched carbon chains and contains from one to twenty carbon atoms, preferably one to six carbon atoms;

cycloalkyl—represents saturated carbocyclic rings branched or unbranched of from 3 to 20 carbon atoms, preferably 3 to 7 carbon atoms;

alkenyl—represents straight and branched carbon chains having at least one carbon to carbon double bond and containing from 2 to 12 carbon atoms, preferably from 3 to 6 carbon atoms;

alkynyl—represents straight and branched carbon chains having at least one carbon to carbon triple bond and containing from 2 to 12 carbon atoms, preferably from 2 to 6 carbon atoms;

aryl (including the aryl portion of aryloxy)—represents a carbocyclic group containing from 6 to 15 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, $CF_3$, amino, alkylamino, dialkylamino, $-COOR^{15}$ or $-NO_2$;

substituted phenyl—represents a phenyl group in which 1 to 3 hydrogen atoms thereof are replaced by the same or different substituents independently chosen from hydroxy, alkyl, halo, nitro, alkoxy, trifluoromethyl, cyano, cycloalkyl, alkenyloxy, alkynyloxy, SH, $S(O)_pR^a$[wherein p is 0, 1 or 2 and $R^a$ is alkyl or aryl]; and halo—represents fluoro, chloro, bromo and iodo.

Certain compounds of the invention may exist in different isomeric (e.g., enantiomers and diastereoisomers) as well as conformational forms. The invention contemplates all such isomers both in pure form and in admixture, including racemic mixtures.

The compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

As noted above, the pyridine and benzene ring structures of formula I may contain one or more substituents $R^1$, $R^2$, $R^3$ and $R^4$. In compounds where there is more than one such substituent, they may be the same or different. Thus compounds having combinations of such substituents are within the scope of the invention. Also, the lines drawn into the rings from the $R^1$, $R^2$, $R^3$ and $R^4$ groups indicate that such groups may be attached at any of the available positions. For example, the $R^1$ and $R^2$ groups may be attached to a carbon atom at the 1, 2, 3 or 4 positions while the $R^3$ and $R^4$ groups may be attached at any of the 7, 8, 9 or 10 positions.

$R^5$, $R^6$, $R^7$ or $R^8$ are attached to the piperidyl, piperidylidenyl or piperazinyl ring. As such they may be the same or different. The variables $R^5$, $R^6$, $R^7$ or $R^8$, in addition to representing H, may represent variables attached to the same or different carbon atoms in said ring. For example, when $R^5$ and $R^6$, or $R^7$ and $R^8$ are combined to represent =O or =S, they are attached to the same carbon atom.

The N-oxides are illustrated herein using the terms NO, N→O, N—O and N+O−. All are considered equivalent as used herein.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts and quaternary ammonium salts. For example, the pyrido-nitrogen atoms may form salts with strong acid, while compounds having basic substituents such as amino groups also form salts with weaker acids.

Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The quaternary ammonium salts are prepared by conventional methods, e.g., by reaction of a tertiary amino group in a compound of formula I with a quaternizing compound such as an alkyl iodide, etc. The free base forms differ from their respective salt forms somewhat in certain physical properties, such as solubility in polar solvents, but the salts are otherwise equivalent to their respective free base forms for purposes of the invention.

All such acid, base and quaternary salts are intended to be pharmaceutically acceptable salts within the scope of the invention and all acid and base salts are considered equivalent to the free forms of the corresponding compounds for purposes of the invention.

The following processes may be employed to produce compounds of general structural formula I.

A. A compound of general formula II may be coupled with a compound of the formula RCOOH in the presence of coupling agent such as 1-(3-dimethylaminopropyl)-3-ethyl carbodiimde hydrochloride (DEC), N,N'-dicyclohexylcarbodiimide (DCC) or N,N'-carbonyl-diimidazole (CDI) to produce compounds of general structural formula I:

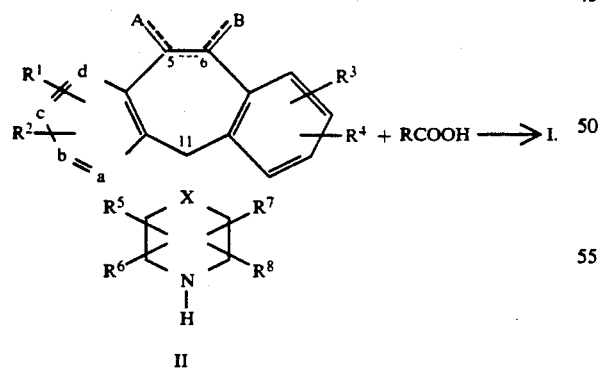

The reaction is usually conducted in an inert solvent such as tetrahydrofuran or methylene chloride at a temperature between about 0° C. and reflux, preferably at about room temperature. When the coupling agent is DCC or DEC, the reaction is preferably run in the presence of 1-hydroxybenzotriazole (HOBT). Method A is the method of choice for preparing the compounds of the invention.

B. A compound of formula II may also be reacted with a compound of formula III in the presence of base to produce compounds of structural formula I:

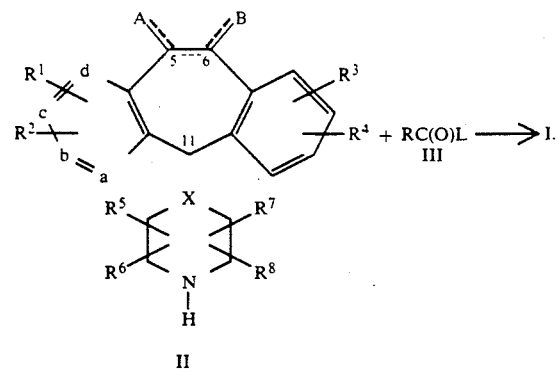

Representative examples of appropriate bases are pyridine and triethylamine. L designates a suitable leaving group. For example, a compound of compound III may be an acyl halide (e.g., L represents halo) or an acyl anhydride, (e.g., L is —O—C(O)—R). The leaving group may also be alkoxy, in which case the compounds of formula I may be produced by refluxing a compound of formula II with an excess of a compound of formula III.

Compounds of general formula II may be prepared from a compound of formula V below by the methods described in WO 88/03138:

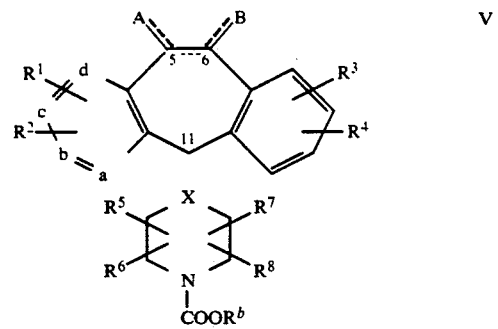

wherein $R^b$ represents alkyl or aryl, e.g., ethyl, 2,2,2-trichloroethyl or phenyl.

C. Alternatively, a compound of formula IV can be reacted with an oxidizing agent an inert solvent such as meta-chloroperbenzoic acid (MCPBA) in methylene chloride or hydrogen peroxide in acetic acid to form a compound of formula I:

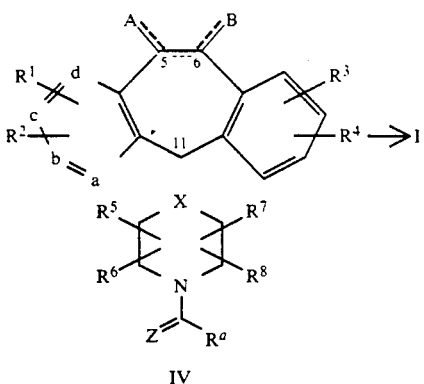

IV wherein $R^a$ represents

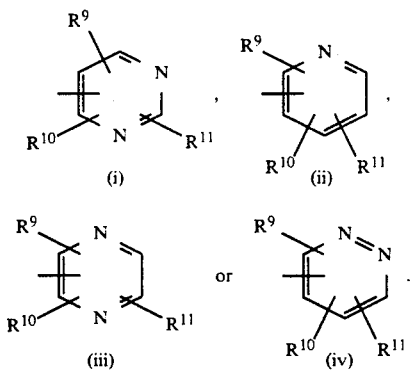

The reaction is usually conducted anywhere from $-15°$ C. to reflux. This method may also oxidize other basic amino groups on the compounds of formula I.

The compounds of formula IV can be prepared employing the methods A and B above, but using compounds of the formula $R^a$COOH or $R^a$COL in place of the compound of III. The compounds of formula IV may also be prepared by reacting a compound of formula VI with a compound of formula $R^a$COL:

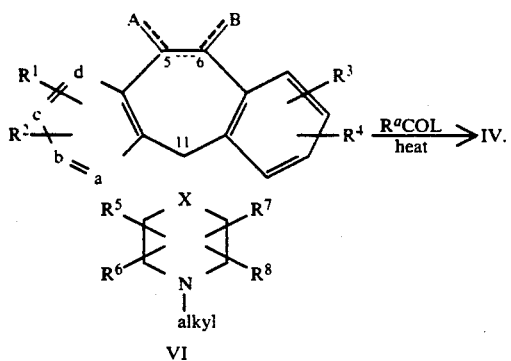

Preferably the reaction is run in the presence of an appropriate nucleophile (e.g. LiI, etc.) in an inert solvent (e.g., toluene, dioxane or xylenes). L is a suitable leaving group such as halo or OC(O)$R^a$. An appropriate base, may be added, and heating is usually required. Typically, a temperature ranging from 50°–150° C. (preferably 100°–120° C.) is utilized depending on the boiling point of the solvent. The compounds of formula VI can be prepared as described in WO 88/03138.

In general, WO 88/03138 describes the starting materials for use in preparing the compounds of the invention. Rather than repeat those process details here, reference is made to pages 19–38 of WO 88/03138 for that purpose. For example, WO 88/03138 discloses how to make the starting materials having a double bond in the 5-6 bridgehead position, having a double or single bond at the 11-position of the tricyclic ring system, having piperazine groups attached at the 11-position of the tricyclic ring system, having substitution on the bridgehead carbon atoms 5 and/or 6, and/or having various $R^1$, $R^2$, $R^3$, and/or $R^4$ substituents on the tricyclic portion of the compounds of the invention, etc. In addition to these, the following methodologies can be employed to prepare compounds of the invention having the tricyclic ring N atom N-oxidized and/or having $R^1$ and/or $R^2$ substituents on the pyridine ring of the tricyclic ring system in the compounds of the invention.

PREPARATION OF PYRIDINE N-OXIDES

The corresponding N-oxides of the invention (e.g., when a, b, c or d in formula I is N—O— can be prepared by treating the corresponding non-oxidized compound (provided that X is carbon) with an appropriate oxidizing agent in an inert solvent. Suitable oxidizing agents are 3-chloroperoxybenzoic acid in methylene chloride or peracetic acid in acetic acid. The reaction is usually carried out at low temperature (e.g. $-10°$ C.) in order to minimize the formation of side products, although higher temperatures are sometimes employed. If X=N, then this nitrogen may be protected as its salt or other complex (e.g., complex with BF$_3$) before oxidation.

SUBSTITUTION ON THE PYRIDINE RING

Various methods can be used as described in WO 88/03138 to provide compounds which are substituted on the pyridine ring, i.e., in positions 2-, 3- and or 4-positions of the tricyclic ring system. For example, the cyclization methods described on pages 20–30 of WO 88/03138 can already have the appropriate substituents on the pyridine ring in place. A variety of substituted pyridines are known in the literature and can be employed in these syntheses. Alternatively, the azaketone of formula XIX (from page 27 of WO 88/03138) wherein $R^1$ and $R^2$ are both H can be converted to the appropriately substituted azaketone where $R^1$ and $R^2$ are non-H substituents. If both $R^1$ and $R^2$ are desired to be non-H substituents the procedure would be repeated.

The azaketone is thus reacted with an oxidizing agent such as meta-chloroperoxybenzoic acid (MCPBA) or hydrogen peroxide to produce the corresponding compound in which the nitrogen of the pyridine ring is as an N-oxide:

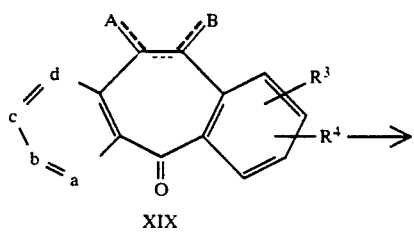

XIX

-continued

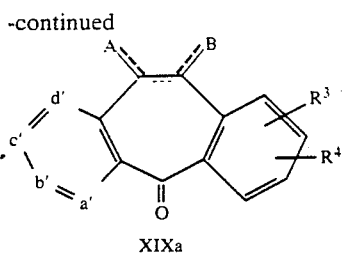

XIXa where one of a', b', c' or d' is N→O and the others are CH or CR$^1$ or CR$^2$. This reaction is normally run at temperatures from −15° C. to reflux, more typically at about 0° C. The reaction is preferably conducted in an inert solvent such as methylene chloride for MCPBA or acetic acid for hydrogen peroxide.

The azaketone N-oxide of formula XIXa can then be reacted with a chlorinating agent such as SO$_2$Cl$_2$ or SOCl$_2$ to form a compound of formula XIXb. Typically, this reaction results in monosubstitution of Cl in the ortho or para-position relative to the N atom of the ring.

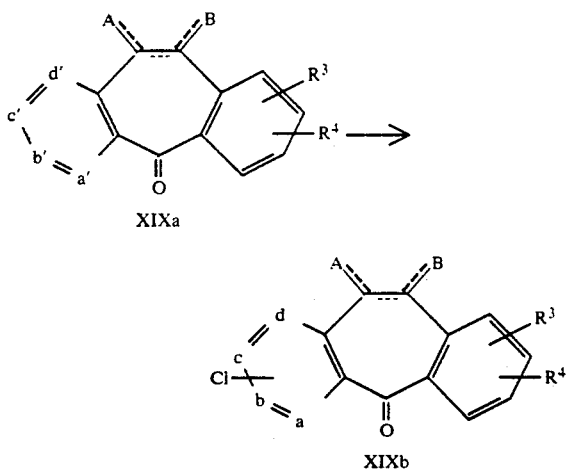

To provide the disubstituted products, steps 1 and 2 above are repeated.

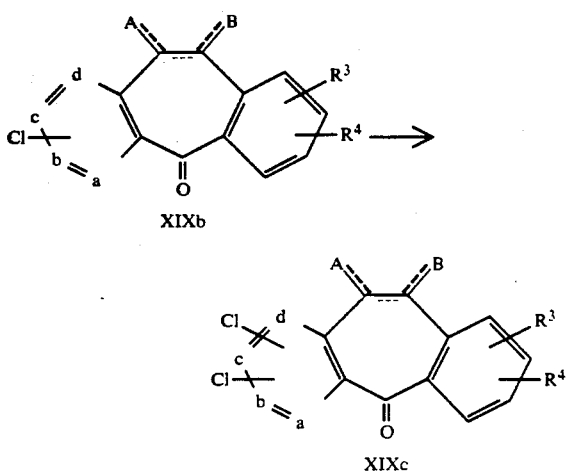

Typically, the resulting disubstituted compounds have Cl ortho and para relative to the N atom of the pyridine ring.

The mono or disubstituted compounds of formulas XIXb and XIXc above can be reacted with various nucleophiles such as alkoxides, amines, thiols, etc. This will result in compounds where one or both of the Cl substituents are replaced by the nucleophile to provide a compound of formula XIXd or a compound easily converted to formula XIXd.

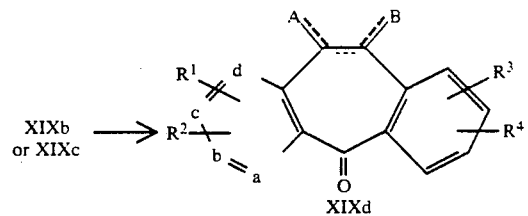

The substituted ketone formula XIXd can then be converted to the target compound of the invention by the methods described above and in WO 88/03138 and in U.S. Pat. No. 3,326,924.

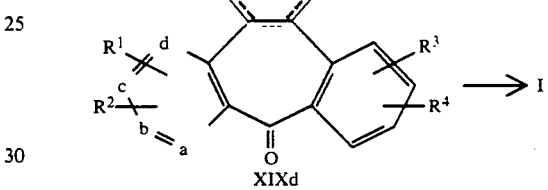

Alternatively, the Cl substituted azaketones of formula XIXb or XIXc above can be converted to the corresponding derivatives of formula II above R$^1$ and/or R$^2$ is Cl by methods analogous to those described above. At this point the Cl substitunt(s) can be displaced by an appropriate nucleophile to provide the desired substituent. Suitable nucleophiles include alkoxide, amines, thiols, etc. This reaction usually requires higher temperatures (e.g., from about 100° to about 200° C.) than the displacement reaction to produce ketone XIXd above. It is also usually conducted in a sealed vessel in an inert solvent. The compound of formula II is then converted compound of formula I as described above.

Various electrophilec species can also be added to the pyridine ring from the corresponding halo-substituted pyridine (formula II where R$^1$ is halo, preferably bromo or iodo). Transmetallation of the halo derivative using an alkyl lithium (e.g. n-BuLi) provides the lithio derivative, which can then be quenched with the appropriate electrophile (e.g. R$^1$L, etc.).

Where Z represents sulfur, a compound of formula I where Z is oxygen is reacted with P$_2$S$_5$, Lawesson's reagent, or another reagent capable of introducing sulfur in place of oxygen. The reaction may take place at elevated temperature in pyridine, toluene or other suitable solvents. In this and other reactions, numerous conversions of a compound of formula I (Z=O) to another compound of formula I (Z=S) are possible.

In the above processes, it is sometimes desirable and/or necessary to protect certain R$^1$, R$^2$, R$^3$ and R$^4$ etc., groups during the reactions. Conventional protecting groups are operable as described in Greene, T. W., "Protective Groups In Organic Synthesis," John Wiley & Sons, New York, 1981. For example, the groups listed in column 1 of the following table may be protected as indicated in column 2 of the table:

TABLE 1
PROTECTED GROUPS

| 1. GROUP TO BE PROTECTED | 2. PROTECTED GROUP |
| --- | --- |
| —COOH | —COOalkyl, —COObenzyl, —COOphenyl, 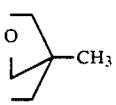 |
| >NH | >NCOalkyl, >NCObenzyl, >NCOphenyl |
| >CO | 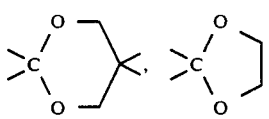 |
| —OH | 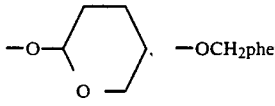, —OCH$_2$phenyl, —OCH$_3$, OSi(CH$_3$)$_2$(t-Bu), |
| —NHR, wherein R is any substituent on an amino group within the scope of the claims | 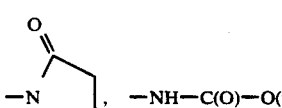, —NR—CO—CF$_3$, —NRCOCH$_3$, —NRCH$_2$— phenyl |
| —NH$_2$ | 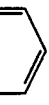, —NH—C(O)—O(t-Bu) |

Other protecting groups well known in the art also may be used. After the reaction or reactions, the protecting groups may be removed by standard procedures.

The compounds of the invention possess platelet-activating factor ("PAF") and histamine antagonistic properties. The compounds of the invention are, therefore, useful when PAF and/or histamine are factors in the disease or disorder. This includes allergic diseases such as asthma, adult respiratory distress syndrome, urticaria and inflammatory diseases such as rheumatoid arthritis and osteoarthritis. For example, PAF is an important mediator of such processes as platelet aggregation, smooth muscle contraction (especially in lung tissue), vascular permeability and neutrophil activation. Recent evidence implicates PAF as an underlying factor involved in airway hyperreactivity.

The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vivo test mimics clinical use of PAF antagonists to provide data which simulates clinical use of the compounds described herein.

A. In Vitro Studies

Platelet Aggregation Assay

Platelet-activating factor (PAF) causes aggregation of platelets by a receptor-mediated mechanism. Therefore, PAF-induced platelet aggregation provides a simple and convenient assay to screen compounds for PAF antagonism.

Human blood (50 ml) was collected from healthy male donors in an anticoagulant solution (5 ml) containing sodium citrate (3.8%) and dextrose (2%). Blood was centriguged at 110×g for 15 min. and the supernatant platelet-rich plasma (PRP) carefully transferred into a polypropylene tube. Platelet-poor-plasma (PPP) was prepared by centrifuging PRP at 12,000×g for 2 min. (Beckman Microfuge B). PRP was used within 3 hr. of drawing the blood.

PAF was dissolved in chloroform:methanol (1:1, v/v) at a concentration of 2 mg/ml and stored at $-70°$ C. An aliquot of this solution was transferred to a polypropylene tube and dried under a flow of nitrogen gas. To the dried sample was added Hepes-saline-BSA (BSA=bovine serum albumen) buffer (25 mM Hepes, pH 7.4, 1254 mM NaCl, 0.7 mM MgCl$_2$ and 0.1% BSA) to obtain a 1 mM solution and sonicated for 5 min. in a bath sonicator. This stock solution was further diluted to appropriate concentrations in Hepes-saline-BSA buffer. Collagen (Sigma) and adenosine diphosphate (ADP) (Sigma) were purchased as solutions. Test compounds were initially dissolved in dimethyl sulfoxide (DMSO) at a concentration of 50 mM and then further diluted in Hepes-saline-BSA buffer to achieve appropriate concentrations.

When an aggregating agent such as PAF is added to PRP, platelets aggregate. An aggregometer quantifies this aggregation by measuring and comparing light (infra-red) transmission through PPP and PRP. Aggregation assays were performed using a dual-channel aggregometer (Model 440, Chrono-Log Corp., Havertown, Pa.). PRP (0.45 ml) in aggregometer cuvettes was continually stirred (37° C.). Solutions (50 μL) of test compounds or vehicel were added to the PRP and, after incubation for 2 min., 10–15 μl aliquots of PAF solution were added to achieve a final concentration of $1-5\times10^{-8}M$. Incubations were continued until the increase in light transmission reached a maximum (usually 2 min.). This increase in light transmission reflecting platlet aggregation is transmitted to a computer by the Chrono-Log model 810 AGGRO/LINK interface. The AGGRO/LINK calculates the slope of transmission change, thus providing the rate of aggregation. Values for inhibition were calculated by comparing rates of aggregation obtained in the absence and the presence of the compound. For each experiment, a standard PAF antagonist such as 8-chloro-6,11-dihydro-11-(1-acetyl-4-piperidylidene)-5H-benzo[5,6]cyclohepta[1,2-b]pyridine was used as a positive control.

Compounds that inhibit PAF-induced aggregation were tested against several other aggregating agents including collagent (0.2 mg/ml) and ADP (2 μM). Compounds showing no activity against these latter agents were considered to be specific PAF antagonists. Results are shown in TABLE 2 below.

B. In Vivo Studies: Agonist-Induced Responses

Spasmogen-Induced Bronchospasm in Guinea Pigs

Male Hartley guinea pigs (450-550 g) were obtained from Charles River Breeding Laboratories. The animals were fasted overnight and the following day were anesthetized with 0.9 ml/kg i.p. of dialurethane (containing 0.1 g/ml diallylbarbituric acid, 0.4 g/ml ethylurea and 0.4 g/ml urethane). The left jugular vein was cannulated for the administration of compounds. The trachea was cannulated and the animals were ventilated by a rodent respirator at 55 strokes/min. with a stroke volume of 4 ml. A side arm to the tracheal cannula was connected to a pressure transducer to obtain a continuous measure of inflation pressure. Bronchoconstriction was measured as the percent increase in inflation pressure that peaked within 5 min. after challenge with spasmogen. The animals were challenged i.v. with either histamine (10 ug/kg), methacholine (10 μg/kg), 5-hydroxytryptamine (10 μg/kg), or PAF (0.4 μg/kg in isotonic saline containing 0.25% BSA). Each animal was challenged with only a single spasmogen. The effect of a compound on the bronchospasm is expressed as a percent inhibition of the increase in inflation pressure compared to the increase in a control group. Results are shown in TABLE 2 below.

and antihistaminic properties to varying degrees, i.e., certain compounds have strong PAF antagonistic activity, but have weaker antihistaminic activity. Other compounds are strong antihistamines but weaker PAF antagonists. Several of the compounds are both strong PAF antagonists and potent antihistamines. Consequently, it is within the scope of this invention to use each of these compounds when clinically appropriate. For example, if a strong PAF antagonist is required, but weaker antihistaminic activity is necessary, such a compound could be chosen by the clinician. Alternatively, if both potent PAF antagonism and antihistaminic activity are required, a different compound of the invention would be utilized by the clinician.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose.

TABLE 2

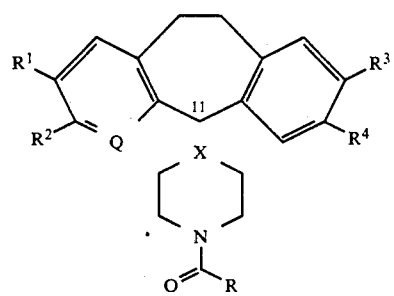

| | | | | | | | | PAF Antagonism (in vitro) IC$_{50}$ (μM) | Agonist Bronchospasm (in vivo) - oral | | | |
|---|---|---|---|---|---|---|---|---|---|---|---|---|
| | | | | | | | | | PAF | | Histamine | |
| R | Q | R$^1$ | R$^2$ | R$^3$ | R$^4$ | X | 11-double bond | | Dose | % Inhibition | Dose | % Inhibition |
| ![pyridine N-oxide] | N | H | H | Cl | H | C | yes | 0.2 | 10 mg/kg | 100 | 10 mg/kg | 90 |
| ![pyridine N-oxide] | N$^+$O$^-$ | H | H | Cl | H | C | yes | 0.5 | 10 mg/kg | 15 | — | — |
| ![pyridine N-oxide] | N | * | H | Cl | H | C | yes | 1.0 | 3 mg/kg | 40 | — | — |
| ![pyridine N-oxide] | N | CH$_3$ | H | Cl | H | C | yes | 0.1 | 3 mg/kg | 22 | — | — |
| ![pyridine N-oxide] | N | H | H | Cl | H | N | no | 0.2 | 3 mg/kg | 98 | 3 mg/kg | 0 |

*tertiary butyl

As seen from the data of TABLE 2 above, the compounds of structural formula I exhibit PAF antagonist Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or waterpropylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application. The appropriate dosage can be determined by comparing the activity of the compound with the activity of a known antihistaminic compound such as 8-chloro-6,11-dihydro-11-(1-ethoxycarbonyl-4-piperidylidene)-5H-benzo[5,6]cycloheptal[1,2-b]pyridine, which compound is disclosed in U.S. Pat. No. 4,282,233.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgement of the attending clinician considering such factors as age, condition and size of the patient as well as severity of the symptoms being treated. A typical recommended dosage regimen is oral administration of from 10 mg to 1500 mg/day preferably 10 to 750 mg/day, in two to four divided doses to achieve relief of the symptoms. The compounds are non-toxic when administered within this dosage range.

The following examples are intended to illustrate, but not to limit, the present invention.

PREPARATIVE EXAMPLE I

A.   N-(1,1-DIMETHYLETHYL)-3-METHYL-2-PYRIDINE CARBOXAMIDE

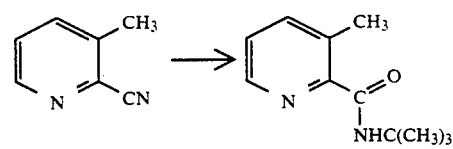

Suspend 2-cyano-3-methyl pyridine (400 g) in t-butanol (800 mL) and heat to 70° C. Add concentrated sulphuric acid (400 mL) dropwise over 45 minutes. Maintain the temperature at 75° C., until the reaction is complete, and for an additional 30 minutes. Dilute the mixture with water (400 mL), charge with toluene (600 mL) and bring to pH 10 with concentrated aqueous ammonia. Maintain the temperature at 50°-55° C. during the work up. Separate the toluene phase, and reextract the aqueous layer. Combine toluene phases and wash with water. Remove the toluene to yield the title compound N-(1,1-dimethylethyl)-3-methyl-2-pyridine carboxamide, as an oil, from which solid product is crystallized. (Yield 97%, as determined by an internal standard assay with gas chromatography).

B.   3-[2-(3-CHLOROPHENYL)ETHYL]-N-(1,1-DIMETHYLETHYL)-2-PYRIDINE CARBOXAMIDE

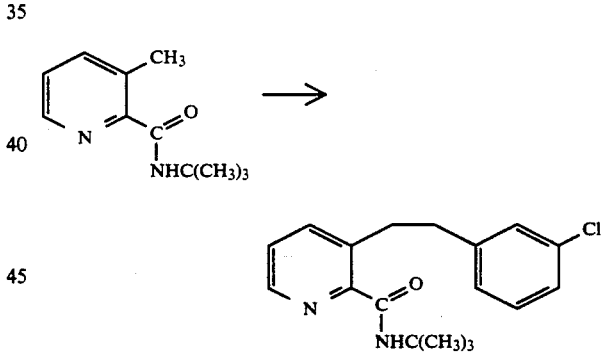

Dissolve the title compound of Preparative Example 1A, N-(1,1-dimethylethyl)-3-methyl-2-pyridine carboxamide (31.5 g.) in tetrahydrofuran (600 mL) and cool the resulting solution to −40° C. Add n-butylithium (2 eq.) in hexane while maintaining the temperature at −40° C. The solution turns deep purple-red. Add sodium bromide (1.6 g) and stir the mixture. Add solution of m-chlorobenzylchloride (26.5 g., 0.174 mole) in tetrahydrofuran (125 mL) while maintaining the temperature at −40° C. Stir the reaction mixture until the reaction is complete as determined by thin layer chromatography. Add water to the reaction until the color is dissipated. Extract the reaction mixture with ethyl acetate, wash with water, and concentrate to a residue which is the title compound. (Yield 92% as shown by chromatography).

C.   3-[2-(3-CHLOROPHENYL)ETHYL]-2-PYRIDINECARBONITRILE

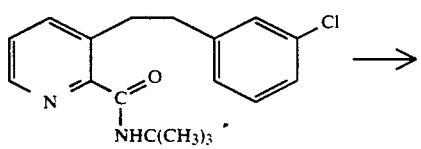

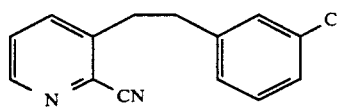

Heat a solution of the title compound of Preparative Example 1B, 3-[2-(3-chlorophenyl)ethyl]-N-(1,1-dimethylethyl)-2-pyridine carboxamide (175 g, 0.554 mole) in phosphorous oxychloride (525 mL, 863 g, 5.63 mole) and reflux for 3 hours. Determine completion of the reaction by thin layer chromatography. Remove any excess phosphorous oxychloride by distillation at reduced pressure and quench the reaction in a mixture of water and isopropanol. Bring to pH 5-7 by adding 50% aqueous sodium hydroxide solution while maintaining the temperature below 30° C. Filter the crystalline slurry of crude product and wash with water. Purify the crude product by slurrying the wet cake in hot isopropanol, and cool to 0°-5° C. Filter the product, wash with hexane and dry at a temperature below 50° C. to yield the title compound. (Yield: 118 g (HPLC purity 95.7%), m.p. 72° C.-73° C., 89.4% of theory).

D. 1-(METHYL-4-PIPERIDINYL)[3-(2-(3-CHLOROPHENYL)ETHYL)-2-PYRIDINYL]METHANONE HYDROCHLORIDE

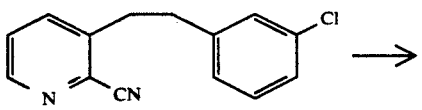

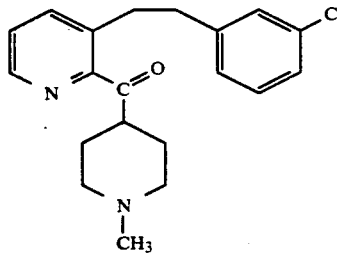

Dissolve the title compound of Preparative Example 1C, (118 g, 0.487 mole) in dry tetrahydrofuran (1.2 L) and add N-methylpiperidyl magnesium chloride (395 mL, 2.48 mole/liter, 0.585 mole, 1.2 eq.) over 15 minutes. Maintain the temperature at 40° C.-50° C. by cooling with water as necessary, for 30 minutes. Determine completion of the reaction by thin layer chromatography. Quench the reaction by reducing the pH to below 2 with 2N HCl and stir the resulting solution at 25° C. for 1 hour. Remove the bulk of the tetrahydrofuran by distillation and adjust the resulting solution to pH 3.5 by addition of aqueous sodium hydroxide. Cool to 0° to 5° C. and filter off the crystalline hydrochloride salt product. Wash with ice cold water and dry to constant weight at 60° C. to yield the title compound. (Yield: 168.2 g (HPLC purity 94%), m.p. 183°-185° C., 89% of theory).

E. 8-CHLORO-11-(1-METHYL-4-PIPERIDYLIDENE)-6,11-DIHYDRO-5H-BENZO[5,6]CYCLOHEPTA[1,2-b]PYRIDINE

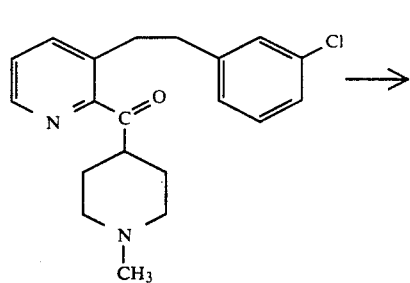

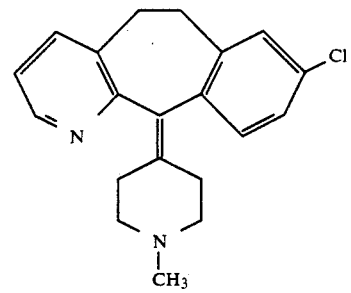

Dissolve the title compound of Preparative Example 1D above (59 g, 0.15 mole) in hydrofluoric acid (120 mL, 120 g, 6.0 mole) at −35° C. and add boron trifluoride (44.3 g, 0.66 mole) over 1 hour. Determine completeness of the reaction by thin layer chromatography. Quench the reaction using ice, water and potassium hydroxide bringing the solution to a final pH of 10. Extract the product with toluene and wash with water and brine. Concentrate the toluene solution to a residue, and dissolve in hot hexane. Remove the insolubles by filtration and concentrate the filtrate to yield the title compound as an off-white powder. (Yield: 45.7 g (HPLC purity: 95%), 92% of theory).

Alternative Step E: 8-CHLORO-11-(1-METHYL-4-PIPERIDYLIDENE)-6,11-DIHYDRO-5H-BENZO[5,6]CYCLOHEPTA[1,2-b]PYRIDINE React the title compound of Preparative Example 1D above (177 g, 0.49 mole) in trifluoromethanesulfonic acid (480 ml, 814.1 g, 5.31 mole) at 90°-95° C. for 18 hours under nitrogen. Determine the completeness of the reaction by thin layer chromatography. Cool the reaction and quench the reaction with ice-water and adjust the pH to 6 with barium carbonate. Extract the product with methylene chloride, and concentrate under reduced pressure to about 1 liter. Wash with water, and extract the product into 1N HCl which is treated with 30 g of activated charcoal, and filter through celite. Adjust the pH of the filtrate to 10 with aqueous sodium hydroxide (50%), extract the product into methylene chloride, and remove under reduced pressure to form a residue. Dissolve the residue in hot hexane, and filter to remove insolubles. Concentrate the filtrate to yield the title compound as a beige powder. (Yield: 126 g (HPLC purity 80%), 65% of theory).

F. 8-CHLORO-11-(1-ETHOXYCARBONYL-4-PIPERIDYLIDENE)-6,11-DIHYDRO-5H-BENZO[5,6]CYCLOHEPTA[1,2-b]PYRIDINE

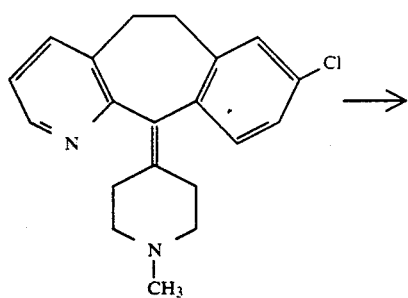

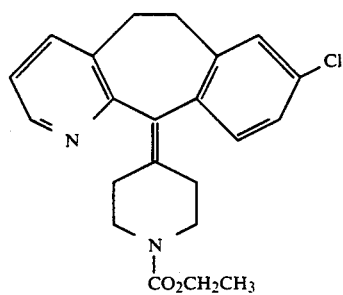

Dissolve the title compound of Preparative Example 1E above (45.6 g, 0.141 mole) in toluene (320 mL) at 80° C. and to it gradually add ethyl chloroformate (40.4 mL, 45.9 g, 0.423 mole). Following complete addition, maintain the temperature at 80° C. for 1 hour, then add diisopropylethylamine (2.7 mL, 2.00 g, 0.016 mole) and additional ethyl chloroformate (4.1 mL, 4.65 g, 0.0429 mole). Monitor completeness of the reaction by thin layer chromatography. Upon completion, cool the reaction mixture to ambient temperature, and wash the toluene solution with water. Concentrate the organic layer to a residue and dissolve in hot acetonitrile (320 mL). Decolorize the solution with 14 g of activated charcoal. Remove the activated charcoal by filtration and concentrate the filtrate to a crystalline slurry. Cool the mixture to 0°–5° C., and isolate the product by filtration. Wash with cold acetonitrile and dry the product at below 70° C. to yield the title compound. (Yield: 42.4 g (HPLC purity 97.4%), 80% of theory).

G. 8-CHLORO-11-(4-PIPERIDYLIDENE)-6,11-DIHYDRO-5H-BENZO[5,6]CYCLOHEPTA[1,2-b]PYRIDINE

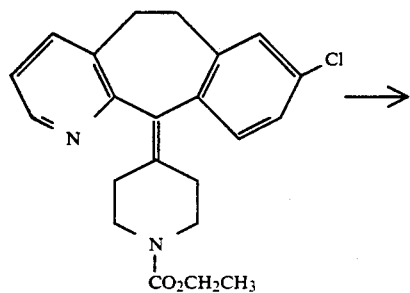

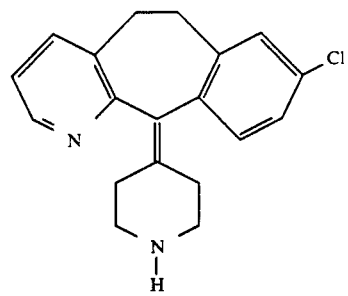

Hydrolize the title compound of Preparative Example 1F, 8-chloro-11-(1-ethoxycarbonyl-4-piperidylidene)-6,11-dihydro-5H-benzo[5,6]cyclohepta[1,2-b]pyridine (39 g, 0.101 mole) with KOH (50 g) in ethanol (305 mL) and water (270 mL) at reflux under an argon atmosphere for 64 hours. Partially distill off the ethanol and dilute the residue with brine, and extract with ethyl acetate (3×). Wash the combined organic phases with water and dry with Na$_2$SO$_4$. Remove the solvent to give a solid which can be recrystallized from toluene to give the title compound as a white solid. (Yield: 24.5 g, 77%, melting point 154°–155° C.).

H. By substituting in step 1B above, an appropriately substituted benzylic halide listed in TABLE 3 below for meta-chlorobenzylchloride, and employing basically the same methods as steps C through G, the products listed in TABLE 3 below are prepared. Reaction times are determined by TLC or HPLC. In some instances purification of the product by chromatography is necessary.

TABLE 3

Product of step G

| halide | R$^3$ | R$^4$ | A | m.p. |
|---|---|---|---|---|
| Br-C₆H₄-F (meta) | F | H | H | 133.5–134.5° C.$^a$ |
| Cl-C₆H₃(Cl)(Cl) | Cl | Cl | H | 150–152° C.$^b$ |
| Br-C₆H₄-CH$_3$ | CH$_3$ | H | H | 142–144° C.$^c$ |
| Br-C₆H₄-Br | Br | H | H | 146–148° C. |
| Br-C₆H₄-OCH$_3$ | OCH$_3$ | H | H | crude solid |

TABLE 3-continued

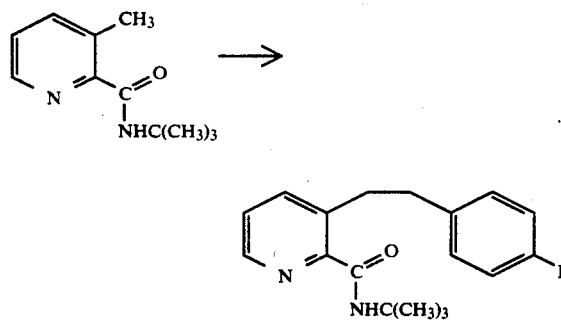

| halide | R³ | R⁴ | A | m.p. |
|---|---|---|---|---|
| Br-CH₂-naphthyl | R³ & R⁴ = benzo | | H | glass |
| CH₃I— Then repeat step B with Br-CH₂-C₆H₄-Cl (3-Cl) | Cl | H | CH₃ | glass |

*Step E required trifluoromethanesulfonic acid.
ᵇRecrystallized from toluene.
ᶜRecrystallized from acetone and pentane.

PREPARATION EXAMPLE 2

A. N-(1,1-DIMETHYLETHYL)-3-[2-(4-FLUOROPHENYL)ETHYL]-2-PYRIDINE CARBOXAMIDE

Cool a solution of N-(1,1-dimethylethyl)-3methyl-2-pyridinecarboxamide (38.4 g, 0.2 mole) in dry THF (250 mL) to −40° C. and add n-butyl lithium (185 mL, 0.44 mole). Add sodium bromide (1.9 g, 18 mmol.) and stir for 15 minutes. Add 4-fluorobenzylchloride (31.8 g, 0.22 mole) and stir for 2.5 hours while warming to −5° C. Quench the reaction with water and extract the product twice with ethyl acetate, then wash with brine (2×). Dry the organic phase over Na₂SO₄, filter and remove the solvent to give the title compound. (60.0 g, Yield 99%, m.p. 59°-61° C.)

B. 3-[2-(4-FLUOROPHENYL)ETHYL]-2-PYRIDINE CARBONITRILE

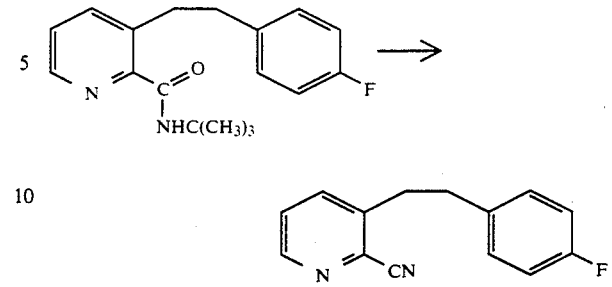

Heat the title compound of Preparative Example 2A above (60.0 g, 0.2 mole) in POCl₃ (200 mL) to 110° C. under an argon atmosphere for 3.5 hours. Pour the reaction onto ice and basify with NaOH (50%) solution. Extract the mixture with ethyl acetate (3×) and wash with water. Wash with brine and dry over Na₂SO₄. Remove the solvent and pass the residue through a coarse SiO₂ (60-200 mesh) column to give the title compound as a white solid (40 g, Yield 88%, m.p. 48°-49° C.).

C. 9-FLUORO-5,6-DIHYDRO-11H-BENZO[5,6-]CYCLOHEPTA[1,2-b]PYRIDIN-11-ONE

Cyclize the title compound of Preparative Example 2B above (31.5 g, 139 mmol) in polyphosphoric acid (1.24 kg) at 200° C. for 5.5 hours. Pour onto ice and basify with NaOH solution (50%). Extract the product with chloroform (3×) and wash with brine. Dry the organic phase with Na₂SO₄, filter and remove the solvent to give the title compound (20.4 g, yield 64%, m.p. 78°-81° C. after recrystallization from diisopropyl ether).

D. 9-FLUORO-11-(1-METHYL-4-PIPERIDINYL)-6,11-DIHYDRO-5H-BENZO[5,6-]CYCLOHEPTA[1,2-b]PYRIDIN-11-OL

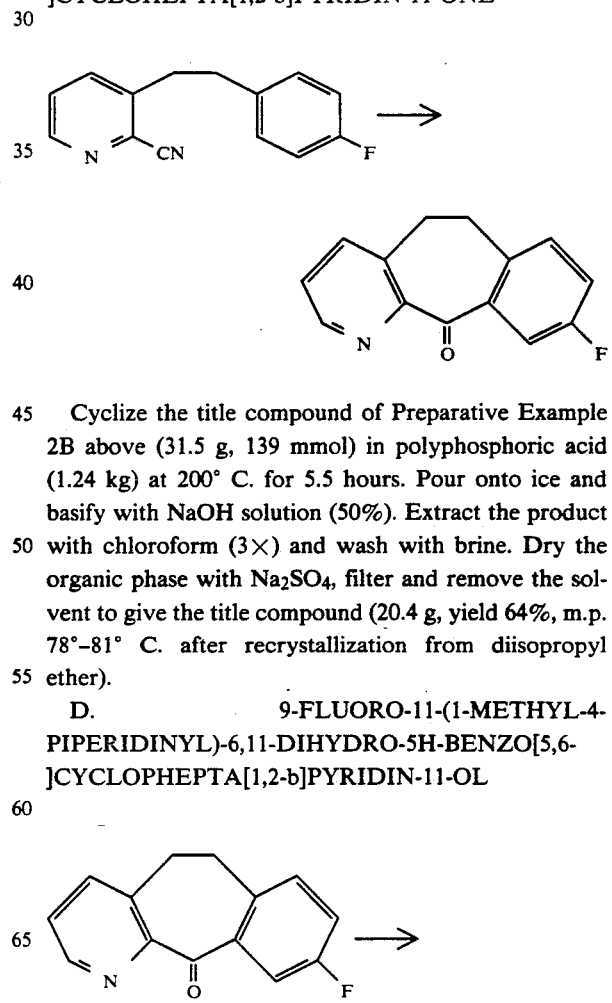

-continued

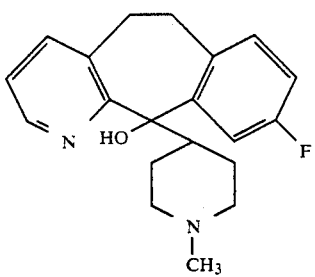

Dissolve the title compound of Preparative Example 2C above (10.0 g, 44 mmol) in THF (100 mL) and add slowly to a cooled (−40° C.) solution of the Grignard reagent prepared from N-methyl-4-chloropiperidine (57.9 mL, 88 mmol) and magnesium in THF (70 mL). Stir the mixture for about 1 hour while warming up to 0° C. Quench the reaction with NH4Cl solution and extract with ethyl acetate (2×). Wash the organic phase with brine and dry over Na2SO4, filter and remove the solvent. Purify the residue with flash chromatography and elute with methanol (5%) in CHCl3 to give the title compound as white granular crystals. (10.1 g, Yield 70%, m.p. 126°–127° C. after recystallization from diisopropyl ether.)

E. 9-FLUORO-11-(1-METHYL-4-PIPERIDYLENE)-6,11-DIHYDRO-5H-BENZO[5,6-]CYCLOHEPTA[1,2-b]PYRIDINE

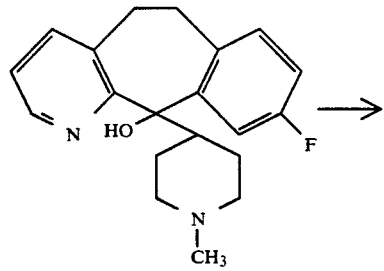

Add the title compound of Preparative Example 2D above (7.3 g, 22.3 mmol) to a mixture of cooled H2SO4 and CF3SO3H (1:1), (146 mL). Stir the reaction mixture for 0.5 hours at ice bath temperature and then at room temperature for 1.5 hours. Pour the reaction mixture onto ice and basify with NaOH (50%) solution. Extract the product with ethyl acetate (3×) and wash with brine. Dry the organic phase over Na2SO4, filter and remove the solvent to give a crude oil. Charcoal the oil and recrystallize from ethyl acetate and isopropyl ether to give the title compound. (5.6 g, Yield 82%, m.p. 134.5°–135.5° C.).

F. 9-FLUORO-11-(1-ETHOXYCARBONYL-4-PIPERIDYLIDENE)-6,11-DIHYDRO-5H-BENZO[5,6]CYCLOHEPTA[1,2-b]PYRIDINE

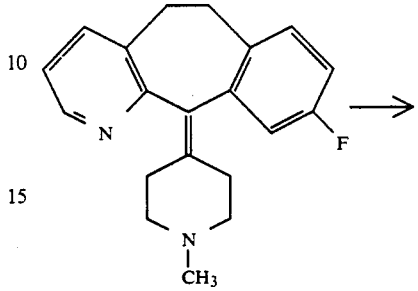

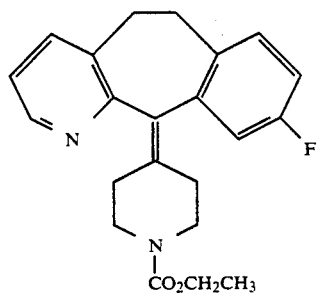

Stir a solution of the title compound of Preparative Example 2E above (5.0 g, 16.2 mmol) and triethylamine (2.6 g, 26 mmol) in dry toluene (60 mL) at 80° C. under an argon atmosphere, and add ethylchloroformate (9.8 g, 90 mmol) via a syringe. Stir the reaction at this temperature for 30 minutes and at room temperature for one hour. Filter the reaction and remove the solvent. Pass the residue through a coarse SiO2 column (60–200 mesh), and elute with CHCl3 to yield the title compound as a white solid. (4.5 g, Yield 76%, m.p. 112°–114° C. after trituration with pentane).

G. 9-FLUORO-11-(4-PIPERIDYLIDENE)-6,11-DIHYDRO-5H-BENZO[5,6]CYCLOHEPTA[1,2-b]PYRIDINE

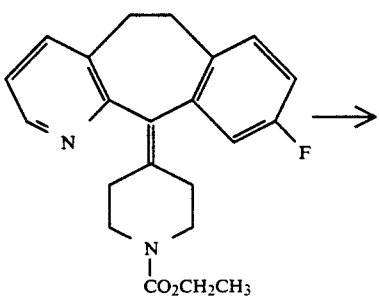

-continued

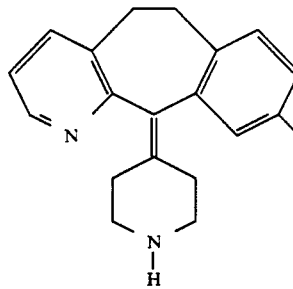

Reflux the title compound of Preparative Example 2F above (3.83 g, 10.4 mmol) with KOH (4.6 g) in 50 mL of ethanol/H₂O (1:1) for 4 hours under an argon atmosphere. Pour the reaction mixture into a brine solution and extract with ethyl acetate (2×), dry over Na₂SO₄ and filter. Remove the solvent to give the title compound (2.86 g, Yield 90%, m.p. 138°–140° C.).

H. By employing the appropriately substituted benzyl halide listed in Table 4 in place of 4-fluorobenzyl chloride in step 2A above, the desired products shown in the second column of TABLE 4 below are prepared by employing basically the same process as described in steps 2A–2G. Workup time is determined by either TLC or HPLC. In some instances purification of the product by chromatography is necessary.

TABLE 4

Product of step G

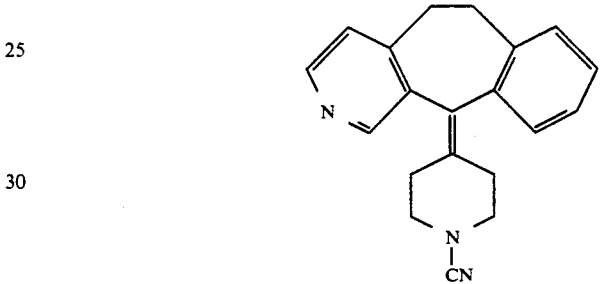

| halide | R³ | R⁴ | m.p. |
|---|---|---|---|
| 4-Br-benzyl-Cl | H | Cl | 134–135° C.ᵃ |
| 4-Cl-benzyl-F | H | F | 138–140° C.ᵇ |
| 3,4-diF-benzyl-Br | F | F | 120–122° C.ᵇ |

ᵃRecrystallized from ethyl acetate and pentane.
ᵇTriturated with pentane.

PREPARATIVE EXAMPLE 3

A. 6,11-DIHYDRO-11-(1-METHYL-4-PIPERIDYLIDENE)-5H-BENZO[5,6]CYCLOHEPTA[1,2-c]PYRIDINE

The compound 5,6-dihydro-11H-benzo[5,6]cyclohepta[1,2-c]pyridine-11-one, may be prepared by following the methods described in U.S. Pat. No. 3,419,565. This ketone may be converted to the title compound by the methods previously described in Preparative Example 2, steps D and E.

B. 11-(1-CYANO-4-PIPERIDYLIDENE)-6,11-DIHYDRO-5H-BENZO[5,6]CYCLOHEPTA[1,2-c]PYRIDINE

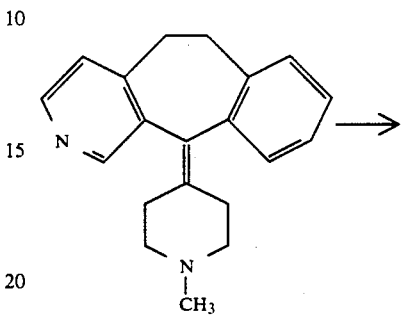

To a solution of 400 mg (1.35 mmole) of 11-(1-methyl-4-piperidylidene)-6,11-dihydro-5H-benzo[5,6]cyclohepta[1,2-c]pyridine in 5.0 mL of benzene at room temperature and under an argon atmosphere was added dropwise a solution of 168 mg (1.59 mmole) of cyanogen bromide in 4 mL of benzene. After 30 min. the mixture was poured into water and extracted once with EtOAc. The organic layer was isolated, washed once with brine, dried over Na₂SO₄, filtered, and concentrated in vacuo. The residue was purified via flash chromatography [2.5% CH₃OH in CH₂Cl₂] to give 150 mg (37%) of the title compound as a solid: m.p. 212°–214° C.

C. 11-(4-PIPERIDYLIDENE)-6,11-DIHYDRO-5H-BENZO[5,6]CYCLOHEPTA[1,2-c]PYRIDINE

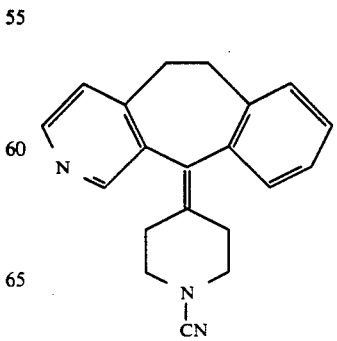

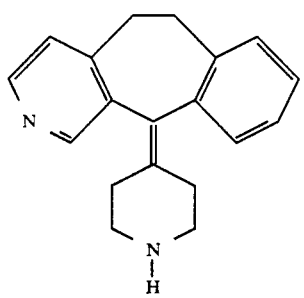

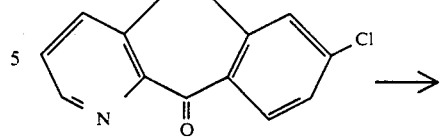

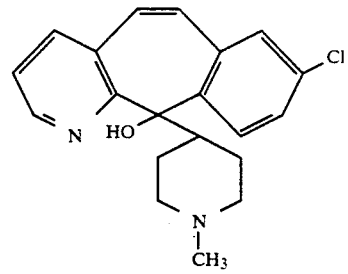

A mixture of 140 mg (0.46 mmole) of 11-(1-cyano-4-piperidylidene)-6,11-dihydro-5H-benzo[5,6]cyclohepta[1,2-c]pyridine in 20 mL of 30% aqueous HCl was refluxed for about 22.5 hrs. The mixture was poured into ice water, basified with 25% aqueous NaOH, and extracted twice with $CH_2Cl_2$. The combined organic portions were dried over $Na_2SO_4$, filtered, and concentrated in vacuo. The product was purified via flash chromatography [5% $CH_3OH$ saturated with $NH_3$ in $CH_2Cl_2$] to give 95 mg (75%) of the title compound as a glass.

PREPARATIVE EXAMPLE 4

A. 8-CHLORO-11H-BENZO[5,6]CYCLOHEPTA[1,2-b]PYRIDIN-11-ONE

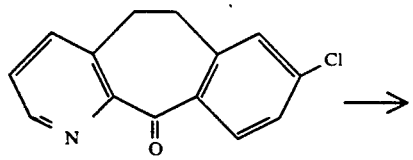

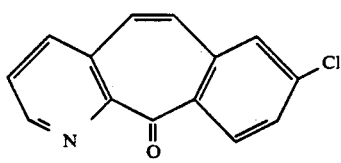

Reflux a mixture of 8-chloro-5,6-dihydro-11H-benzo[5,6]cyclohepta[1,2-b]pyridin-11-one (25.99 g, 0.107 mol.), recrystallized N-bromosuccinimide (21.35 g, 0.120 mol) and 167 mg (0.102 mmol) of azobisisobutyrylnitrile (AIBN) in 400 mL of carbon tetrachloride under an argon atmosphere for 1.25 hours. Cool the solution slowly to 50° C. and filter off the resultant precipitate.

Reflux the precipitate with 1,8-diazabicyclo[5.4.0]undec-7-ene (DBU) (20 mL, 0.134 mol) in $CH_2Cl_2$ (400 mL) for 1 hour. Wash with water (3×), dry over magnesium sulfate, filter and concentrate in vacuo. Recrystallize the crude product from $CH_2Cl_2$/toluene to give the title compound as colorless needles (8.93 g, yield 35%).

B. 8-CHLORO-11-(1-METHYL-4-PIPERIDINYL)-11H-BENZO[5,6]CYCLOHEPTA[1,2-b]PYRIDIN-11-OL

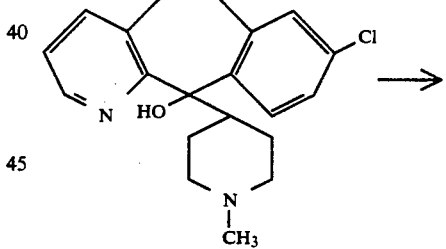

To a mixture of 22 mL of 0.5M Grignard reagent of N-methyl-4-chloropiperidine (11.0 mmole) in THF at 45° C. and under a nitrogen atmosphere was added dropwise over 15 min. a solution of 1.06 gm (4.39 mmole) of 8-chloro-11H-benzo[5,6]cyclohepta[1,2-b]pyridin-1-one in 23 mL of dry THF. After 2 hr. 40 min. the reaction mixture was poured into water and extracted three times with ethyl acetate (EtAcO). The organic portions were combined, washed two times with brine, dried over $MgSO_4$, filtered, and concentrated in vacuo. The residue was purified via flash chromatography [10% $CH_3OH$ in $CH_2Cl_2$] to give 970 mg (65%) of the title compound as a glass.

C. 8-CHLORO-11-(1-METHYL-4-PIPERIDILIDENE)-11H-BENZO[5,6]CYCLOPHEPTA[1,2-b]PYRIDINE

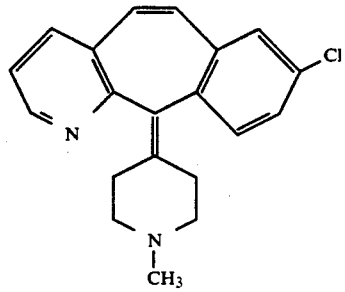

A mixture of 847 mg (2.48 mmole) of 8-chloro-11-(1-methyl-4-piperidinyl)-11H-benzo[5,6]cyclohepta[1,2-b]pyridin-11-ol in 5 mL of concentrated sulfuric acid and 5 mL of trifluoromethanesulfonic acid was heated at 70° C. for 4.1 hr. The mixture was cooled to room temperature, poured into ice cold 30% aqueous KOH, and extracted three times with $CH_2Cl_2$. The organic D. 8-CHLORO-11-[1-(2,2,2-TRICHLOROETHOX-YCARBONYL)-4-PIPERIDYLIDENE]-11H-BENZO[5,6]CYCLOHEPTA[1,2-b]PYRIDINE

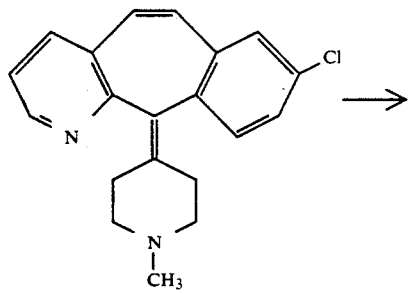

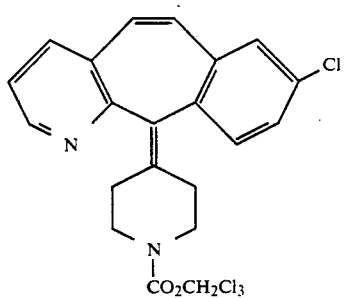

To a mixture of 755 mg (2.34 mmole) of 8-chloro-11-(1-methyl-4-piperidylidene)-11H-benzo[5,6]cyclohepta[1,2-b]pyridine and 1.5 mL of triethylamine in 25 mL of dry toluene at room temperature and under a nitrogen atmosphere was added 650 μL (4.72 mmole) of 2,2,2-trichloroethyl chloroformate. The mixture was then heated to 90° C. Additional amounts of the chloroformate (500 μL and 300 μL) and triethylamine (1.0 mL each time) were added to the mixture after 2 hr. and 3 hr. 40 min., respectively. After total reaction time of 5 hr. the mixture was poured into water and extracted three times with CH$_2$Cl$_2$. The combined organic portions were dried over MgSO$_4$, filtered and concentrated in vacuo. The residue was purified via flash chromatography [1.5% CH$_3$OH in CH$_2$Cl$_2$] to afford 639 mg (56%) of the title compound as a glass.

E. 8-CHLORO-11-(4-PIPERIDYLIDENE)-11H-BENZO[5,6]CYCLOHEPTA[1,2-b]PYRIDINE

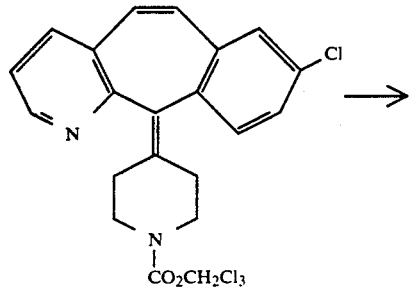

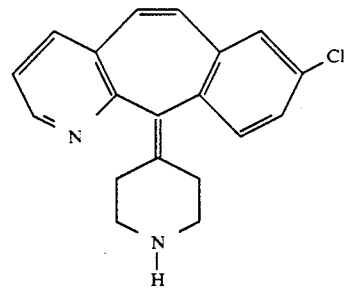

A mixture of 210 mg (0.434 mmole) of 8-chloro-11-[1-(2,2,2-trichloroethoxycarbonyl)-4-piperidylidene]-11H-benzo[5,6]cyclohepta[1,2-b]pyridine and 526 mg (8.05 mmole) of zinc dust in 4 mL of acetic acid was heated at 60°-70° C. After 2 hr. 20 min. another 547 mg (8.37 mmole) of zinc dust was added. After another 30 min. the mixture was basified with 10% aqueous NaOH and extracted four times with CH$_2$Cl$_2$. The combined organic portions were washed once with water, dried over MgSO$_4$, filtered, and concentrated in vacuo. The residue was purified via flash chromatography [5→6% CH$_3$OH/NH$_3$ in CHCl$_3$] to yield 71 mg (53%) of the title compound as a glass.

PREPARATIVE EXAMPLE 5

A. 5-METHOXY-8-CHLORO-11H-BENZO[5,6]CYCLOHEPTA[1,2-b]PYRIDIN-11-ONE
B. 6-METHOXY-8-CHLORO-11H-BENZO[5,6]CYCLOHEPTA[1,2-b]PYRIDIN-11-ONE

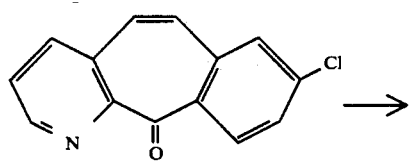

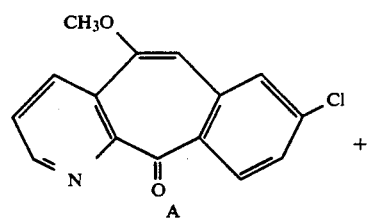

A

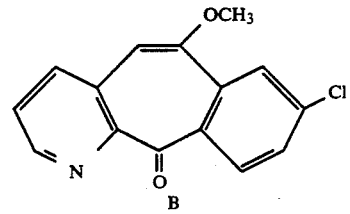

B

Add Br$_2$ (5.10 mL, 99 mmol) to a mixture of 8-chloro-11H-benzo[5,6]cyclohepta[1,2-b]pyridin-11-one (8.15 g, 33.7 mmol) and powdered AgNO$_3$ (23.19 g, 137 mmol) in 300 mL of dry methanol at room temperature and under an argon atmosphere. After 8 hours, add additional AgNO$_3$ (5.90 g, 34.7 mmol) followed by additional Br$_2$ (1.7 mL, 33.0 mmol). After 0.5 hours pour the mixture into water and extract (4×) with CH$_2$Cl$_2$. Combine the organic phases, dry over magnesium sulfate, filter and concentrate in vacuo to give a mixture of the crude bromo ethers.

Dissolve the crude product in CH₂Cl₂ (200 mL) at room temperature and place under an argon atmosphere. Add DBU (20 mL, 134 mmol) and reflux for 1.3 hours. Add additional DBU (10 mL, 67 mmol) and reflux the mixture for an additional hour. Pour the mixture into water and extract (3×) with CH₂Cl₂. Combine the organic phases, wash with water and dry over magnesium sulfate. Filter and concentrate in vacuo. The two isomeric vinyl ethers, title compounds A and B, are separated via flash chromatography [40%→75% ethyl acetate in hexanes] and recrystallize from ethyl acetate hexanes to give title compound A (1.51 g, 14.3%, mp 156° to 158° C.) and title compound B (3.68 g, 35%, mp: 161°–162° C.).

C. 5-METHOXY-8-CHLORO-11-(1-METHYL-4-PIPERIDINYL)-11H-BENZO[5,6]CYCLOHEPTA[1,2-b]PYRIDIN-11-OL

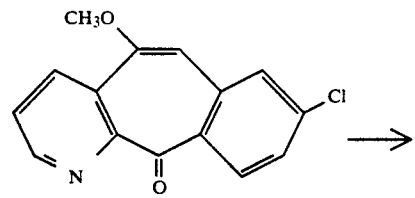

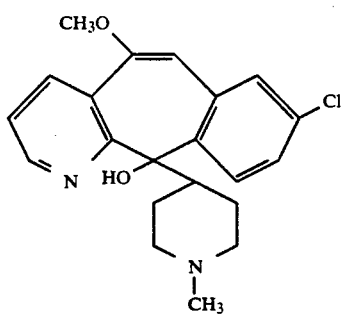

Add a 1.5M Grignard solution of N-methyl 4-chloropiperidine (150 mL, 22.5 mmol) in THF dropwise over a 7 minute period to 5-methoxy-8-chloro-11H-benzo[5,6]cyclohepta[1,2-b]pyridin-11-one (5.00 g, 18.4 mmol) in THF (70 mL) at 0° C. and under an argon atmosphere. Quench the reaction after 30 minutes with a saturated solution of NH₄Cl (pH 8) and extract (3×) with CHCl₃. Combine the organic portions, wash with brine, dry over sodium sulfate, filter and concentrate in vacuo. Purify via flash chromatography (5% CH₃OH in CH₂Cl₂) to give the title compound (3.60 g, 53%) as a solid. The solid may be recrystallized from isopropyl ether to give a white powder (mp: 168°–170° C).

D. 8-CHLORO-11-(1-METHYL-4-PIPERIDYLIDENE)-6,11-DIHYDRO-5H-BENZO[5,6]CYCLOHEPTA[1,2-b]PYRIDIN-5-ONE

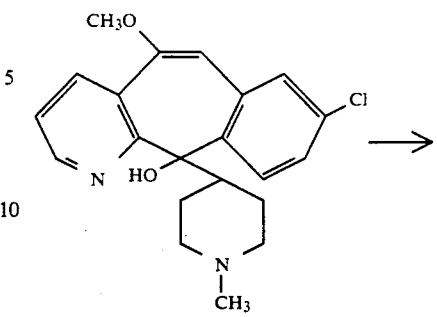

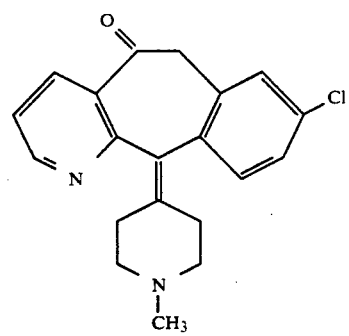

Dissolve 5-methoxy-8-chloro-11-(1-methyl-4-piperidinyl)-11H-benzo[5,6]cyclohepta[1,2-b]pyridin-11-ol (4.26 g) in CH₃OH (6 mL) at 0° C. under an argon atmosphere. Add slowly a cooled solution of 92% aqueous H₂SO₄ (54 mL). Allow the mixture to warm to room temperature for 35 minutes. Pour the solution onto ice, basify with aqueous NaOH (25%), and extract with methylene chloride (3×). Combine the organic portions, wash with brine and dry over sodium sulfate. Filter and concentrate in vacuo. Triturate the residue with isopropyl ether to give an intermediate, 8-Chloro-6,11-dihydro-11-(1-methyl-4-piperidinyl)-5,11-epoxy-5H-benzo[5,6]-cyclohepta[1,2-b]pyridin-5-ol as a white solid (3.58 g., 92%, m.p: 170° to 174° C. as HCl salt).

Dissolve the intermediate compound (3.58 g, 10.0 mmol) in trifluoromethane sulfonic acid (50 mL) and heat to 45° C. under an argon atmosphere for 3 hours. Pour the mixture onto ice, basify with aqueous NaOH (25% w/v), and extract with CHCl₃(3×). Combine the organic portions, wash with brine and dry over sodium sulfate. Filter and concentrate in vacuo. Chromatograph on silica gel (5% CH₃OH in CH₂Cl₂) to give the title compound as an off white solid (1.703 g, 50%, 58% based on recovered starting material). An analytical sample was prepared by recrystallization of the product with ethyl acetate/isopropyl ether (mp: 162°–163° C.).

E. ETHYL-4-(8-CHLORO-5-ETHOXYCARBONYLOXY-11H-BENZO[5,6]CYCLOHEPTA[1,2-b]PYRIDIN-11-YLIDENE)-1-PIPERIDINE CARBOXYLATE

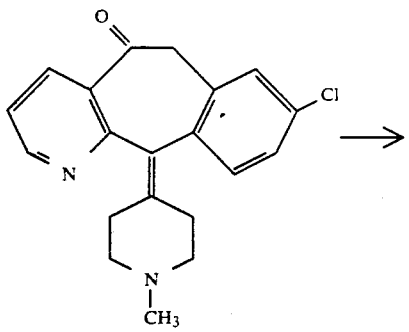

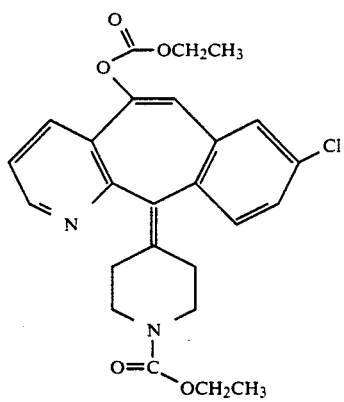

Dissolve the 8-chloro-11-(1-methyl-4-piperidylidene)-6,11-dihydro-5H-benzo[5,6]cyclohepta[1,2-b]pyridin-5-one (617 mg, 1.82 mmol) and triethylamine (0.50 mL, 3.58 mmol) in toluene (12 mL) at 80° C. under an argon atmosphere. Add dropwise over 2 minutes ethyl chloroformate (0.87 mL, 9.10 mmol). After 25 minutes cool the mixture to room temperature, filter, and concentrate in vacuo. Purify the crude product via flash chromatography (1% CH$_3$OH in CH$_2$Cl$_2$) to yield the title compound as a glass (834 mg, 98%).

F. 8-CHLORO-11-(4-PIPERIDYLIDENE)-6,11-DIHYDRO-5H-BENZO[5,6]CYCLOHEPTA-[1,2-b]PYRIDIN-5-ONE

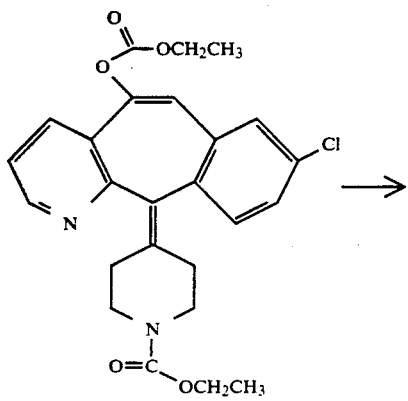

-continued

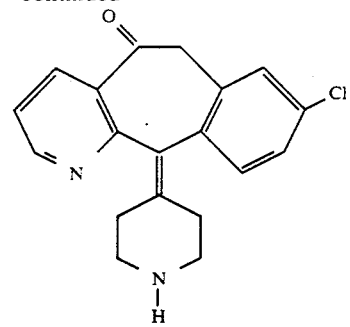

Mix ethyl 4-(8-chloro-5-ethoxycarbonyloxy-11H-benzo[5,6]cyclohepta[1,2-b]pyridi-11-ylidene)-1-piperidine carboxylate (897 mg, 1.91 mmol) and aqueous KOH (20 mL, 13% w/v) in ethanol (15 mL) and reflux under an argon atmosphere for 25 hours. Pour the mixture into water and extract with CHCl$_3$ (3×). Combine the organic portions, wash with brine, dry over sodium sulfate, filter, and concentrate in vacuo. Purify the residue via flash chromatography (2% CH$_3$OH saturated with NH$_3$ in CH$_2$Cl$_2$) and triturate with isopropyl ether to give the title compound as a white solid (417 mg, 67%, mp: 194°-196° C. (dec)).

G. 5-HYDROXY-8-CHLORO-11-(4-PIPERIDYLIDENE)-6,11-DIHYDRO-5H-BENZO[5,6]CYCLOHEPTA[1,2-b]PYRIDINE

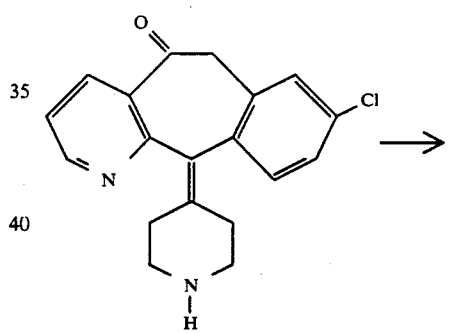

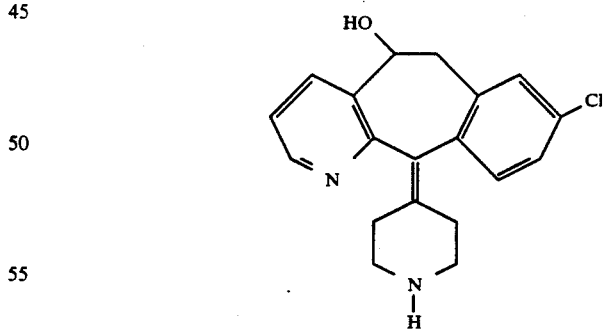

Mix 8-chloro-11-(4-piperidylidene)-6,11-dihydro-5H-benzo[5,6]cyclohepta[1,2-b]pyridin-5-one (400 mg, 1.23 mmol) in CH$_3$OH (20 mL) at 0° C. under an argon atmosphere, and add in 3 portions NaBH$_4$ (total 231 mg, 6.10 mmol). After 30 minutes, pour the mixture into water and extract (3×) with ethyl acetate. Combine the organic portions, wash with brine, dry over sodium sulfate, filter and concentrate in vacuo. Triturate the solid with isopropyl ether/ethyl acetate to give the title compound as a white solid (351 mg, 87%).

H. By using a similar procedure to that described in Parts C through G above of Preparative Example 5, one can prepare 6-hydroxy-8-chloro-11-(4-piperidylidene)-6,11-dihydro-5H-benzo[5,6]cyclohepta[1,2-b]pyridine from 6-methoxy-8-chloro-11H-benzo[5,6]cyclohepta[1,2-b]pyridin-11-one of in Part B. However, in Part D of Preparative Example 5, one may use the following procedure in its place:

A mixture of 2.00 g (5.39 mmol) of 6-methoxy-8-chloro-11-(1-methyl-4-piperidinyl)-11H-benzo[5,6]cyclohepta[1,2-b]pyridin-11-ol in 87% aqueous sulfuric acid was stirred at room temperature and under an argon atmosphere. After 30 min 30 mL of trifluoromethanesulfonic acid was added and the mixture was heated to 115° C. One hour later the mixture was cooled to room temperature, poured onto ice, basified with 5% aqueous sodium hydroxide and extracted with methylene chloride (2×). The combined organic portions were washed with brine, dried over Na2SO4, filtered, and concentrated in vacuo to give 1.41 g of 8-chloro-5,11-dihydro-11-(1-methyl-4-piperidinylidene)-6H-benzo[5,6]cyclohepta-[1,2-b]pyridin-6-one. The material was recrystallized from ethyl acetate/isopropyl ether to give 1.12 g (61%) of the ketone as a granular solid: mp 181°-183° C.

PREPARATIVE EXAMPLE 6

A. 1,2,6-TRIMETHYL-4-CHLOROPIPERIDINE

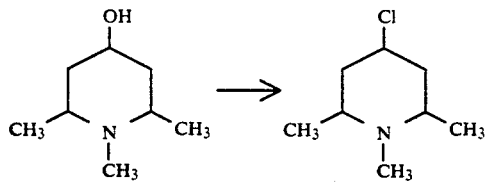

The starting material, 1,2,6-trimethyl-4-piperidinol, may be prepared by the method disclosed in *Archi Kem*, Volume 27, pages 189-192 (1955). To a cooled (ice-bath) solution of 1,2,6-trimethyl-4-piperidinol (12.2 g, 85.3 mmol) in 120 mL of dry benzene was slowly added thionylchloride (17 mL, 233 mmole). The dark reaction mixture was then warmed to 70° C. for 20 min. The reaction was cooled and then suspended in water followed by filtration. The filtrate was extracted once with diethylether. The aqueous layer was separated and then basified with 30% NaOH solution. The product was then extracted twice with CH2Cl2, washed once with brine, dried (Na2SO4), filtered and solvent removed to give a crude brown liquid which was distilled (2-4 mmHg, 62°-64° C.) to give the title compound (8.0 g, 58% yield).

B. 8-CHLORO-11-(1,2,6-TRIMETHYL-4-PIPERIDINYL)-6,11-DIHYDRO-5H-BENZO[5,6-]CYCLOHEPTA[1,2-b]PYRIDIN-11-OL

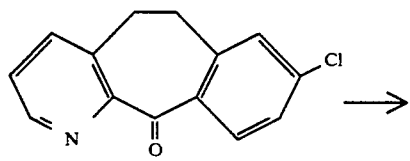

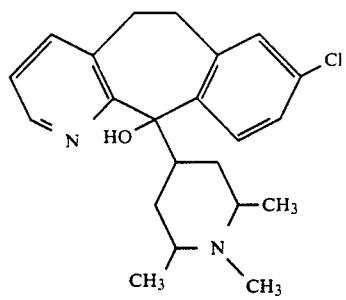

The chloride, 1,2,6-trimethyl-4-chloropiperidine, (4.2 g, 26 mmol) was slowly dripped into a solution of dry THF (18 mL) containing Mg (633 mg, 26.3 mm). The Grignard reagent was then formed after heating for 6 hours at 70° C.

To a cooled (ice-bath), stirred solution of 8-chloro-5,6-dihydro-11H-benzo[5,6]cyclohepta[1,2-b]pyridin-11-one (6.3 g, 26 mmol) in THF (50 mL) was added the above Grignard reagent. The reaction was allowed to stir for 1 hr. at this temperature and then quenched with NH4Cl solution. The product was extracted 3× with ethyl acetate, washed once with brine, dried (Na2SO4), filtered and solvent removed to give a crude brown material which was chromatographed to give the title compound (5.1 g, 53% yield) as a yellowish glass.

C. 8-CHLORO-11-(1-METHYL-(Z)-2,6-DIMETHYL-4-PIPERIDYLIDENE)-6,11-DIHYDRO-5H-BENZO[5,6]CYCLOHEPTA[1,2-b]PYRIDINE AND THE E ISOMER THEREOF

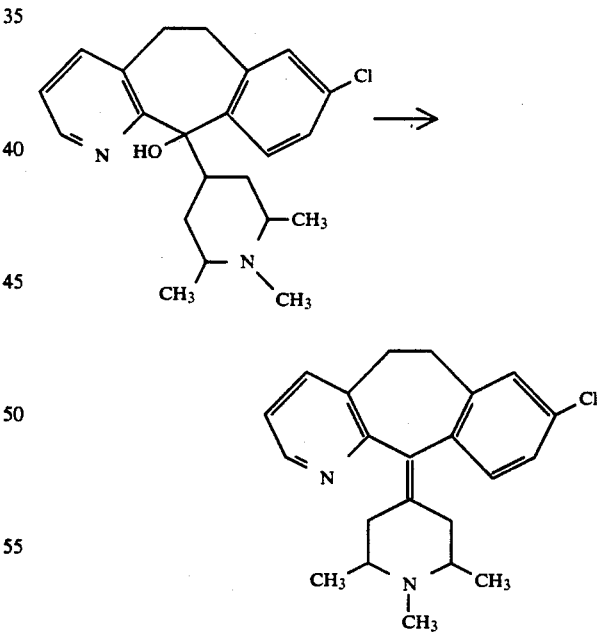

A mixture of 8-chloro-11-(1,2,6-trimethyl-4-piperidinyl)-6,11-dihydro-5H-benzo[5,6]cyclohepta[1,2-b]pyridin-11-ol (5.0 g, 14.1 mmol) in 85% H2SO4 (100 mL) was heated in an oil bath (60°-65° C.) for 3 hours. The reaction was cooled and diluted with water followed by basification with 25% aq. NaOH solution. The crude product was extracted with CH2Cl2, washed with brine, dried (Na2SO4), filtered and solvent removed. Purification and separation of the E and Z isomers via chromatography (2% →5% MeOH saturated with NH₃ in CH₂Cl₂) gave a fraction of the pure Z isomer (300 mg, 6%) and a fraction containing a mixture of E and Z isomers (4.18 g, 82%).

D. 8-CHLORO-11-(1-CYANO-(Z)-2,6-DIMETHYL-4-PIPERIDYLIDENE)-6,11-DIHYDRO-5H-BENZO[5,6]CYCLOHEPTA[1,2-b]PYRIDINE

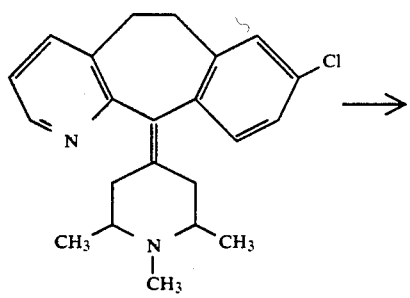

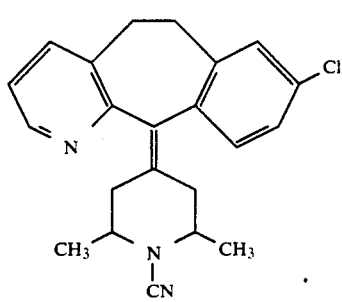

A solution of 300 mg (0.85 mmol) of 8-chloro-11-(1-methyl-(Z)-2,6-dimethyl-4-piperidylidene)-6,11-dihydro-5H-benzo[5,6]cyclohepta[1,2-b]pyridine in benzene (4.5 mL) was slowly dripped into a stirred solution of BrCN (133 mg, 1.2 mmol) in benzene (4.5 mL) at room temperature. This was allowed to stir for 2½ hr under argon. The reaction mixture was suspended between water and ethyl acetate (EtOAc). The EtOAc layer was washed with brine and dried (Na₂SO₄). After filtration the solvent was removed and the crude material was chromatographed (3% CH₃OH in CH₂Cl₂) to give the title compound (251 mg, 81% yield).

E. 8-CHLORO-11-((Z)-2,6-DIMETHYL-4-PIPERIDYLIDENE)-6,11-DIHYDRO-5H-BENZO[5,6]CYCLOHEPTA[1,2-b]PYRIDINE

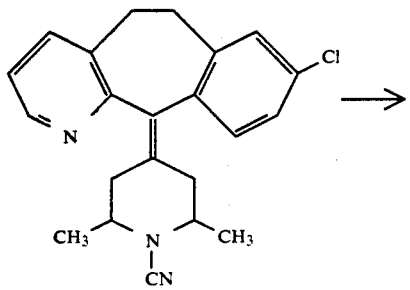

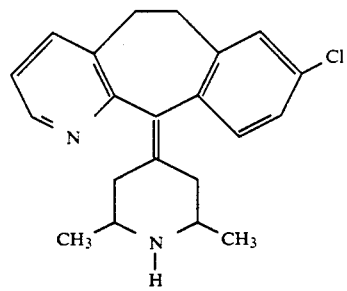

A mixture of 8-chloro-11-(1-cyano-(Z)-2,6-dimethyl-4-piperidylidene)-6,11-dihydro-5H-benzo[5,6]cyclohepta[1,2-b]pyridine (200 mg, 0.55 mmol) in 80% HCl (20 mL) was allowed to reflux for 7 hours. The mixture was cooled and then basified with 25% NaOH. The product was extracted with CH₂Cl₂ (2×), separated, washed once with brine, dried (Na₂SO₄), filtered and solvent removed to give the title compound (174 mg, 93% yield) as a white glass.

F. By following similar procedures in steps D and E above, 8-chloro-11-(1-methyl-(E)-2,6-dimethyl-4-piperidylidene)-6,11-dihydro-5H-benzo[5,6]cyclohepta[1,2-b]pyridine was converted to 8-chloro-11-((E)-2,6-dimethyl-4-piperidylidene)-6,11-dihydro-5H-benzo[5,6]cyclohepta[1,2-b]pyridine.

PREPARATIVE EXAMPLE 7

A. 3,5-DIMETHYLPYRIDINIUM N-OXIDE

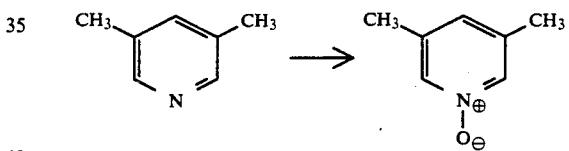

A solution of 285 mL (1.31 mol) of 35% peracetic acid was slowly added to a stirred solution of 149 g (1.39 mol) of 3,5-dimethylpyridine during which the temperature rose to 85° C. and was maintained at this temperature during addition. After the temperature of the mixture dropped to about 35° C. the reaction was stored at 5° C. overnight.

After partial removal of 185 ml of acetic acid via distillation under vacuum, the reaction was washed with NaHSO₄ solution and then neutralized with 10% NaOH solution to pH of about 7. The product was extracted with CH₂Cl₂ to give the title compound as a white solid (yield 142 g, 83%).

B. 1-METHOXY-3,5-DIMETHYLPYRIDINIUM METHYL SULFATE

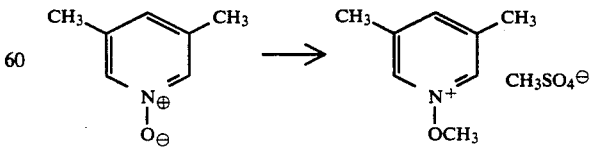

Dimethylsulfate (42.0 g, 0.33 mol) was slowly added to 41.0 g (0.33 mol) of 3,5-dimethylpyridinium N-oxide with mechanical stirring. The mixture was then heated on a steam bath for 1 hr. Then vacuum was applied while cooling to give a brownish solid of the title compound in quantitative yield.

C. 2-CYANO-3,5-DIMETHYLPYRIDINE

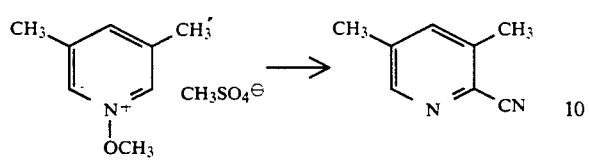

To a cooled (0° C.) solution of sodium cyanide (49.0 g, 0.999 mol, 3.0 eq.) in 135 mL of water (air free) was dripped 1-methoxy-3,5-dimethyl pyridinium methyl sulfate (83.0 g, 0.33 mol) in 100 mL water (air free) in 1.25 hr., keeping the temperature below 3° C. The reaction mixture was stored at about 3° C. overnight. The mixture was filtered and washed with water to give 40 g of the title compound. An analytical sample was recrystallized from isopropyl ether and pentane (4:1) (m.p.: 61°–62° C.).

D. N-(1,1-DIMETHYLETHYL)-3,5-DIMETHYL-2-PYRIDINE CARBOXAMIDE

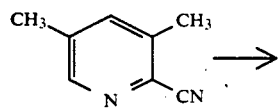

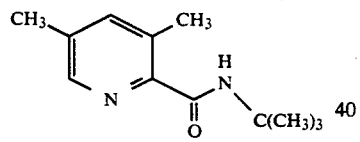

To a stirred solution of 20.3 g (0.153 mol) of 2-cyano-3,5-dimethylpyridine in 100 mL of 20 mL of conc. sulfuric acid within 10 minutes, followed by 20 mL of t-butanol over an additional 15 minutes. The solution was warmed at 75° C. for 30 minutes after which it was cooled to room temperature and basified with 25% NaOH. The product was extracted 3× with EtOAc (600 mL), which was combined and washed 1× with brine, dried (Na₂SO₄), filtered and concentrated in vacuo to give the title compound (31.26 g) as a yellowish oil.

E. 8-CHLORO-3-METHYL-11-(4-PIPERIDYLIDENE)-6,11-DIHYDRO-5H-BENZO[5,6]CYCLOHEPTA[1,2-b]PYRIDINE

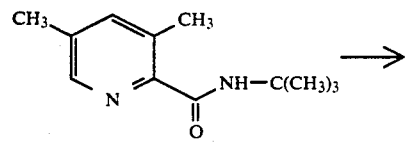

By substituting in step 1B above N-(1,1-dimethylethyl)-3,5-dimethyl-2-pyridine carboxamide for N-(1,1-dimethylethyl)-3-methyl-2-pyridine carboxamide and employing basically the same methods as steps B through G of Preparative Example 1, one obtains 8-chloro-3-methyl-11-(4-piperidylidene)-6,11-dihydro-5H-benzo[5,6]cyclohepta[1,2-b]pyridine. Reaction times are determined by TLC or HPLC.

PREPARATIVE EXAMPLE 8

A. 1-(1-METHYL-4-PIPERIDINYL)-1-[3-(2-PHENYLETHYL)-2-PYRIDYL]METHANOL

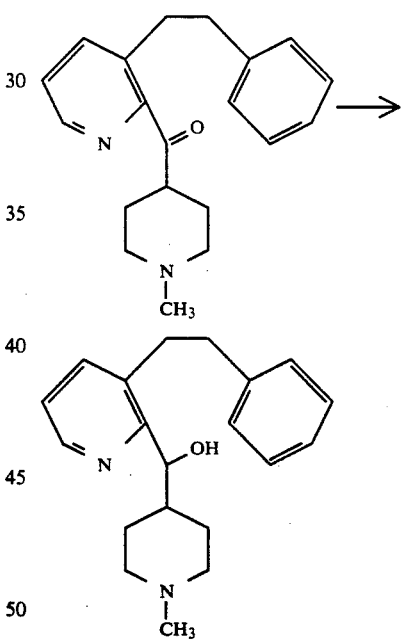

To a mixture of 5.0 g (16.2 mmole) of (1-methyl-4-piperidinyl)[3-(2-phenylethyl)-2-pyridinyl]methanone (which can be prepared in the same manner as described in Preparative Example 1 Steps A–D except using benzyl chloride in place of meta-chlorobenzyl chloride) in 70 mL of methanol was added portionwise 0.8 g (21.1 mmole) of sodium borohydride. The next day the solution was concentrated in vacuo to give a slurry which was dissolved in water and extracted with CHCl₃. The combined organic portions were dried over MgSO₄, filtered, and concentrated in vacuo to provide a liquid which was distilled (bp 190°–195° C. at 1 mm Hg) to give 4.4 g of the title compound as a viscous oil.

B. 11-1-METHYL-4-PIPERIDYL)-6,11-DIHYDRO-5H-BENZO[5,6]CYCLOHEPTA[1,2-b]PYRIDINE

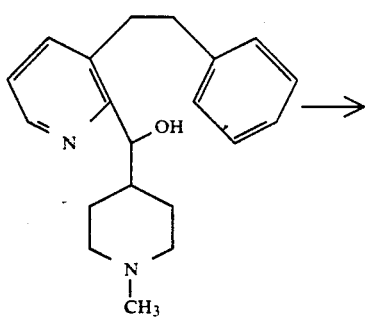

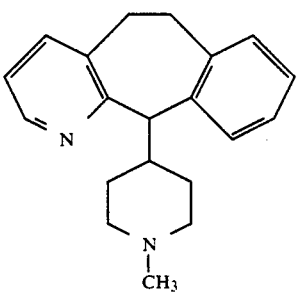

A mixture of 3.5 g (11.3 mmole) of 1-(1-methyl-4-piperidyl)-1-[3-(2-phenylethyl)-2-pyridyl]methanol and 200 g of polyphosphoric acid was heated between 160°–170° C. for 13 hours. The mixture was cooled to room temperature, poured into water, basified with aqueous NaOH and extracted with ether. The combined organic portions were concentrated in vacuo and the product recrystallized to give the title compound as a white solid, (mp 111°–114° C.).

C. 11-(4-PIPERIDYL)-6,11-DIHYDRO-5H-BENZO[5,6]CYCLOHEPTA[1,2-B]PYRIDINE

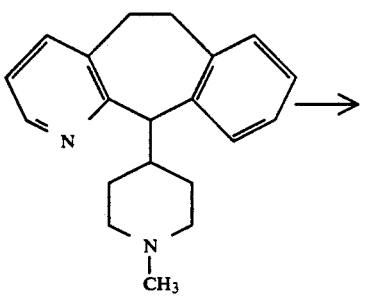

In a similar manner to that described in Preparative Example 1, Steps F–G, 11-(1-methyl-4-piperidyl)-6,11-dihydro-5H-benzo[5,6]cyclohepta[1,2-b]pyridine can be converted to 11-(4-piperidyl)-6,11-dihydro-5H-benzo[5,6]cyclohepta[1,2-b]pyridine.

PREPARATIVE EXAMPLE 9

A. 8-CHLORO-5,6-DIHYDRO-11H-BENZO[5,6-]CYCLOHEPTA-[1,2-B]PYRIDIN-11-ONE N-OXIDE

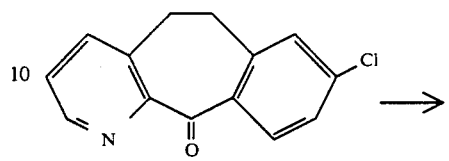

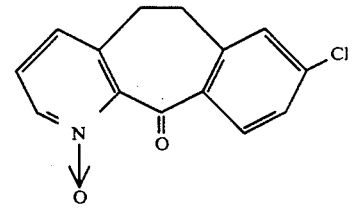

To a mixture of 25.1 grams (0.103 mole) of 8-chloro-5,6-dihydro-11H-benzo[5,6]cyclohepta[1,2-b]pyridin-11-one in 175 ml of dry methylene chloride at 0° C. under an argon atmosphere was added dropwise over 70 minutes a solution of 24.12 grams of 3-chloroperoxybenzoic acid in 150 ml of methylene chloride. After the addition the solution was stirred for ½ hour after which the ice bath was removed. After two days the reaction was poured into 1.0N aqueous sodium hydroxide and extracted with methylene chloride. The organic portions were combined, washed once with water, dried over magnesium sulfate, filtered and concentrated in vacuo. The resultant product was triturated with isopropyl ether and filtered to provide 25.8 grams (96%) yield of the title compound.

B. 2,8-DICHLORO-5,6-DIHYDRO-11H-BENZO[5,6]CYCLOHEPTA[1,2-B]PYRIDIN-11-ONE AND 4,8-DICHLORO-5,6-DIHYDRO-11H-BENZO[5,6]CYCLOHEPTA[1,2-b]PYRIDIN-11-ONE

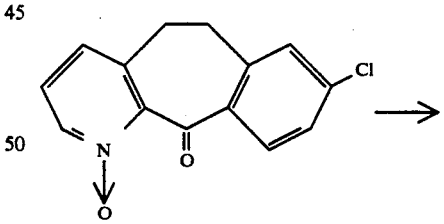

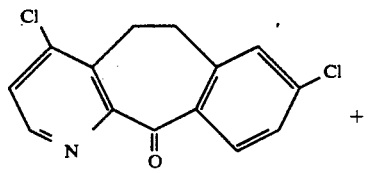

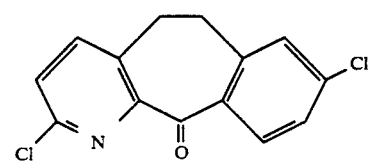

To a mixture of 29.13 grams (112.2 mmol) of the title compound from Preparative Example 9A above, in 40 ml of dry methylene chloride at 0° C. and under argon atmosphere was added 500 ml of 1.0M SO$_2$Cl$_2$ dropwise over 1 hour. The ice bath was then removed and the reaction stirred at room temperature for 1 hr and then refluxed for seven hours. The mixture was poured into 1.0N aqueous NaOH and extracted three times with CH$_2$Cl$_2$. The organic portions were combined, dried over MgSO$_4$, filtered and concentrated in vacuo to yield a product which was purified and separated via flash chromatography to yield the two title compounds.

C. 4-(2,8-DICHLORO-5,6-DIHYDRO-11H-BENZO[5,6]CYCLOHEPTA[1,2-b]PYRIDIN-11-YLIDENE)PIPERIDINE AND 4-(4,8-DICHLORO-5,6-DIHYDRO-11H-BENZO[5,6]CYCLOHEPTA-[1,2-b]PYRIDIN-11-YLIDENE)PIPERIDINE

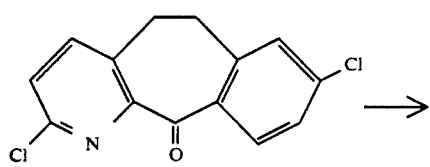

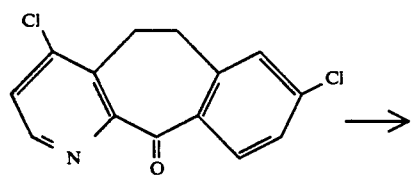

By following essentially the same procedure as that described in parts D-G of Preparative Example 2 above, the 2,8-dichloro and 4,8-dichloro products of Preparative Example 9B above were converted to the corresponding title compounds.

PREPARATIVE EXAMPLE 10

A. 4-(8-CHLORO-2-HYDROXY-5,6-DIHYDRO-11H-BENZO[5,6]CYCLOHEPTA[1,2-b]PYRIDIN-11-YLIDENE)PIPERIDINE

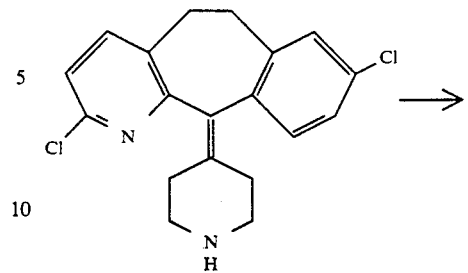

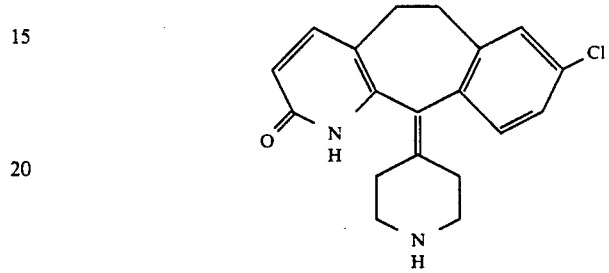

A mixture of 180 mg of the 2,8-dichloro title compound of Preparative Example 9-C above, 7 ml of 2.0N aqueous sodium hydroxide and 7 ml of methanol were heated at 160° C. under a nitrogen atmosphere in a sealed pressure vessel for two days. The vessel was then cooled to room temperature. The mixture was poured into water and extracted three times with methylene chloride. The organic portions were combined, dried over magnesium sulfate, filtered and concentrated in vacuo to provide a residue which was triturated with isopropyl ether/methylene chloride to provide 85 mg of the title compound as a white solid. B. By using the procedure of Preparative Example 10 above, one can make substitutions of other groups at the 2-position by employing the appropriate nucleophile in place of sodium hydroxide (e.g. dimethylamine, ammonia, potassium thiolate, etc.).

PREPARATIVE EXAMPLE 11

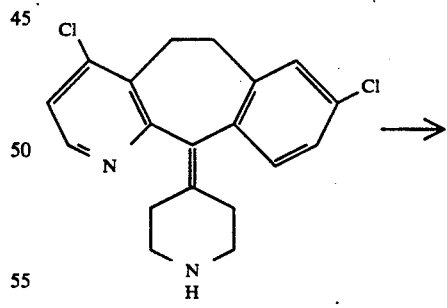

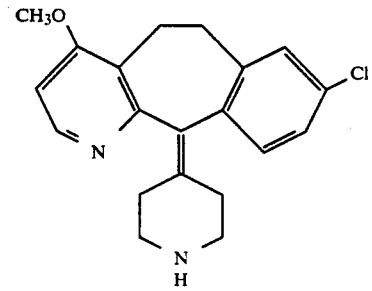

A. 4-(8-CHLORO-4-METHOXY-5,6-DIHYDRO-11H-BENZO[5,6]CYCLOHEPTA[1,2-b]PYRIDIN-11-YLIDENE)PIPERIDINE

A mixture of 212 mg of the 4,8-dichloro title compound of Preparative Example 9-C above, 7 ml of 2.0N aqueous sodium hydroxide and 7 ml of methanol were heated at 135° C. under a nitrogen atmosphere in a sealed pressure vessel for 18 hours. The vessel was then cooled to room temperature. The mixture was poured into water and extracted three times with methylene chloride. The organic portions were combined, dried over magnesium sulfate, filtered and concentrated in vacuo to provide a residue which was purified via flash chromatography (4→7% methanol saturated with ammonia in methylene chloride) and then triturated with isopropyl ether/methylene chloride to provide 144 mg of the title compound as a white glass.

B. By using the procedure of Preparative Example 11 above, one can make substitutions of other groups at the 4-position by employing the appropriate nucleophile in place of sodium hydroxide (e.g. dimethylamine, ammonia, potassium thiolate, etc.).

PREPARATIVE EXAMPLE 12

A. By substituting the compound listed in Column 1 TABLE 5 below for 3,5-dimethylpyridine in Preparative Example 7 above and following basically the same procedure (steps A-E), the compounds listed in Column 2 below can be prepared. Note that the addition of the nitrile group to the pyridine in step C. of Preparative Example 7 can result in the formation of other undesirable isomers which can be removed via flash chromatography.

TABLE 5

| Column 1 | Column 2 | R' = | R" = | R''' = | R'''' = |
|---|---|---|---|---|---|
| Cl, CH₃ pyridine | | H | Cl | H | H |
| | | H | Cl | H | Cl |
| Br, CH₃ pyridine | | H | Br | H | Cl |
| phenyl-CH₃ pyridine | phenyl | H | | H | Cl |
| CH₃, H₃C pyridine | | CH₃ | H | H | Cl |
| CH₃, CH₃ pyridine | | H | H | CH₃ | Cl |

PREPARATIVE EXAMPLE 13

A. 3-(1,1-DIMETHYL-1-ETHYL)-8-CHLORO-5,6-DIHYDRO-11H-BENZO[5,6]CYCLOHEPTA[1,2-b]PYRIDIN-11-ONE

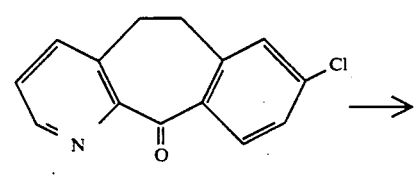

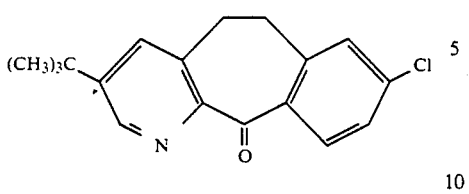

To a mixture of 20.05 grams (82.28 mmol) of 8-chloro-5,6-dihydro-11H-benzo[5,6]cyclohepta[1,2-b]pyridin-11-one in 400 ml of dry tetrahydrofuran at −72° C. and under an atmosphere of nitrogen was added dropwise over 40 minutes 66.0 ml of 2.7M t-butyl magnesium chloride in tetrahydrofuran. The reaction mixture was slowly warmed to room temperature and stirred overnight. The mixture was then poured into 10% aqueous ammonium chloride and extracted four times with methylene chloride. The combined organic portions were dried over magnesium sulfate, filtered, and concentrated in vacuo to give the title compound, along with 8-chloro-11-(1,1-dimethyl-1-ethyl)-6,11-dihydro-5H-benzo[5,6]cyclohepta[1,2-b]pyridin-11-ol. These compounds were separated via flash chromatography to give the title compound, which was recrystallized from isopropyl ether to give 4.37 grams (18%) of the title compound as a white solid.

B. 4-[3-(1,1-DIMETHYL-1-ETHYL)-8-CHLORO-5,6-DIHYDRO-11H-BENZO[5,6]CYCLOHEPTA[1,2-b]PYRIDIN-11-YLIDENE]PIPERIDINE

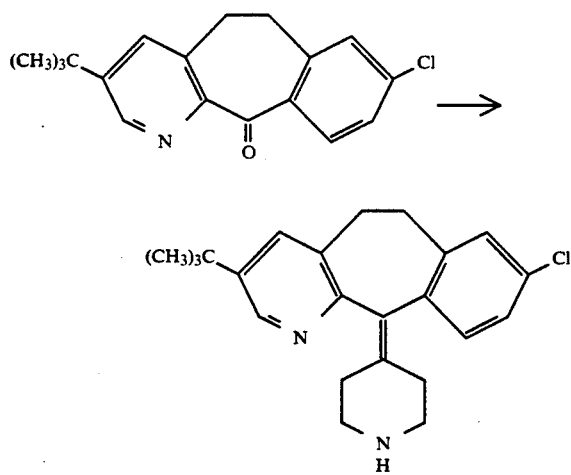

By using the title compound of Part A above and applying essentially the same procedure described in parts D-G of Preparative Example 2 above, one can obtain the title compound.

PREPARATIVE EXAMPLE 14

A. 4-[8-CHLORO-5,6-DIHYDRO-3-(1-HYDROXY-1-ETHYL)-11H-BENZO[5,6]CYCLOHEPTA[1,2-B]PRYIDIN-11-YLIDENE]-PIPERIDINE

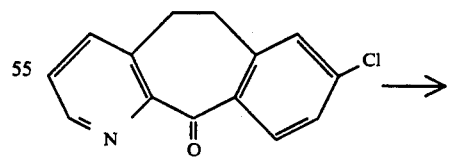

3-Bromo-8-chloro-6,11-dihydro-11-(4-piperidylidene)-5H-benzo[5,6]cyclohepta[1,2-b]pyridine (779.4 mg) in dry tetrahydrofuran (25 mL) was cooled to −76° C. under argon. To this was dripped in n-butyl lithium (1.76 mL in hexane, 2.2 eq.) keeping the temperature below −74° C. After stirring for 10 minutes acetaldehyde was bubbled into the solution until the reaction color turned yellowish in approximately 20 minutes. The mixture was allowed to stir for 20 minutes and then quenched with water followed by extraction with methylene chloride. The organic phase was dried ($Na_2SO_4$) and the filtered. Solvent was removed and the crude product was chromatographed on $SiO_2$, eluted with 10% methanol saturated with ammonia in methylene chloride to give 219 mg of the title compound.

B. By following essentially the same procedure as described above in Preparative Example 14, but using other electrophiles in place of acetaldehyde (e.g., $CO_2$, ethyl propargylate, ethyl formate, etc.), one can make compounds which contain a carboxy, a 3-carboethoxy-1-propen-1-yl, and formyl, respectively, at the 3-position.

PREPARATIVE EXAMPLE 15

A. 8-CHLORO-6,11-DIHYDRO-11-HYDROXY-5H-BENZO[5,6]CYCLOHEPTA[1,2-B]PYRIDINE

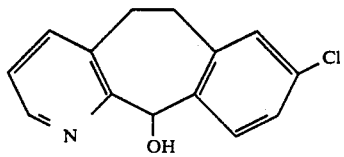

To a mixture of 25.03 (103 mmol) of 8-chloro-5,6-dihydro-11H-benzo[5,6]cyclohepta[1,2-b]pyridin- 11-one in 200 mL of methanol at room temperature and under a nitrogen atmosphere was added portionwise over a period of about 1 hour 4.82 g (124 mmol) of sodium borohydride. Occasional cooling with an ice bath was necessary at times during the addition in order to avoid excessive reflux. After 1.6 hour the mixture was poured into ice cold water and then extracted with ethyl acetate (3×). The combined organic portions were washed with brine, dried over magnesium sulfate, filtered, and concentrated in vacuo. The residue was recrystallized from hot isopropyl ether. The remaining filtrate was purified via flash chromatography (20% ethyl acetate in hexanes) to yield more product which solidified on standing. Both batches were combined to yield 20.41 g of the title compound as a white solid.

B. 8,11-DICHLORO-6,11-DIHYDRO-5H-BENZO[5,6]CYCLOHEPTA[1,2-B]PYRIDINE

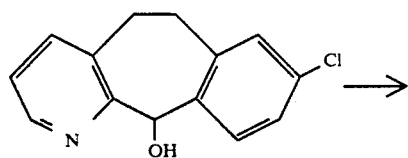

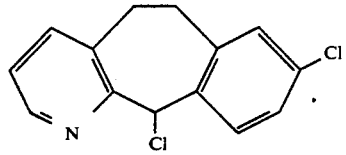

To a mixture of 13.3 g (54 mmol) of 8-chloro-6,11-dihydro-11-hydroxy-5H-benzo[5,6]cyclohepta[1,2-b]pyridine in 290 mL of toluene at −15° C. and under an atmosphere of nitrogen was added via syringe pump over a period of 1 hour 6.20 mL (85.7 mmol) of thionyl chloride. The extent of reaction was monitored by TLC (50% ethyl acetate in hexanes). When completed the mixture was poured into 300 mL of 1.0N aqueous sodium hydroxide and extracted with ethyl acetate (5×). The combined organic portions were washed with brine, dried over sodium sulfate, filtered, and concentrated in vacuo. The residue was taken up in ethyl acetate, quickly filtered through basic alumina, and concentrated again to yield a product which was triturated with pentane to yield 10.22 g of the title compound as a tan solid.

C. 8-CHLORO-11-(1-PIPERAZINYL)-6,11-DIHYDRO-5H-BENZO[5,6]CYCLOHEPTA[1,2-B]PYRIDINE

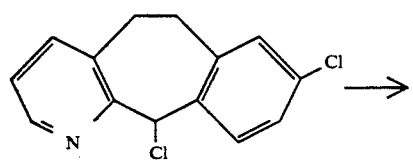

-continued

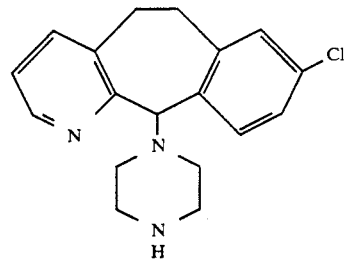

To a mixture of 10.0 g (37.9 mmol) of 8,11-dichloro-6,11-dihydro-5H-benzo[5,6]cyclohepta[1,2-b]pyridine and 1.0 mL of triethylamine in 200 mL of dry tetrahydrofuran at room temperature and under a nitrogen atmosphere was added 33.0 g of piperazine. The mixture was stirred at room temperature for 22.5 hours and then refluxed for 5.5 hours. It was then cooled to room temperature, poured into 250 mL of 5% aqueous sodium hydroxide, and extracted with methylene chloride (3×). The combined organic portions were washed with brine, dried over magnesium sulfate, filtered, and concentrated in vacuo. The residue was purified via flash chromatography (2→5% methanol saturated with ammonia in methylene chloride) to yield the title compound as a glass.

EXAMPLE 1

1-(4-PYRIDINYLCARBONYL)-4-(8-CHLORO-5,6-DIHYDRO-11H-BENZO[5,6]CYCLOHEPTA[1,2-b]PYRIDIN-11-YLIDENE)PIPERIDINE N¹-OXIDE

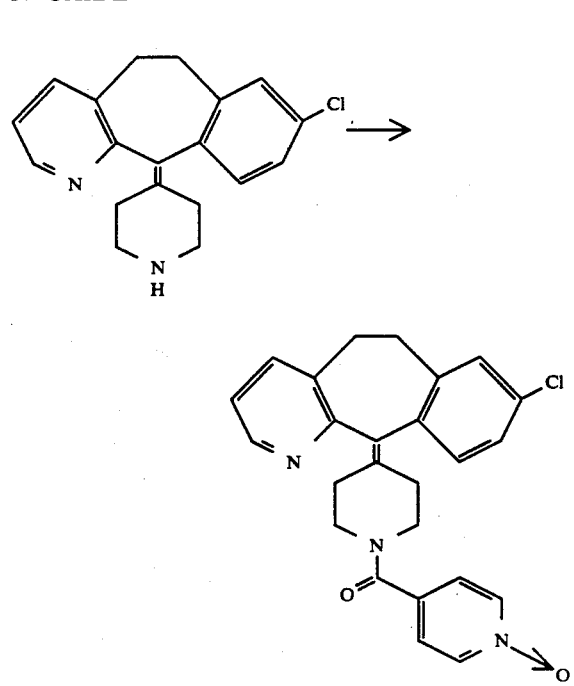

To a mixture of 5.01 g (16.1 mmol) of 4-(8-chloro-5,6-dihydro-11H-benzo[5,6]cyclohepta[1,2-b]pyridin-11-ylidene)piperidine (product from Preparative Example 1, Step G), 2.19 g (15.7 mmol) of isonicotinic acid N-oxide, and 2.33 g (17.2 mmol) of 1-hydroxybenzotriazole hydrate in 30 mL of dry methylene chloride at −15° C. and under a nitrogen atmosphere was added dropwise over 25 minutes a solution of 3.26 g (16.9 mmol) of 1-(3-dimethylaminopropyl)-3-ethylcarbodiimide hydrochloride (DEC) in 60 mL of dry methylene chloride. The reaction mixture was slowly allowed to warm to room temperature. After 3 hours the mixture was poured into a solution of 10% aqueous sodium dihydrogen phosphate and extracted three times with methylene chloride. The combined organic portions were dried over MgSO₄, filtered, and concentrated in vacuo to give a product which was purified via flash chromatography and recrystallized using isopropyl ether to give 1.35 gms (82%) of 1-(4-pyridinyl carbonyl)-4-(8-chloro-5,6-dihydro-11H-benzo[5,6]cyclohepta[1,2-b]pyridin-11-ylidene)piperidine N¹-oxide as a white solid (228° C., dec).

EXAMPLE 2

By essentially the same procedure as set forth in Example 1 above but using the amines set forth in Column 1 below in place of 4-(8-chloro-5,6-dihydro-11H-benzo[5,6]cyclohepta[1,2-b]pyridin-11-ylidene)piperidine, one can obtain the compounds listed in Column 2 of TABLE 6 below:

TABLE 6

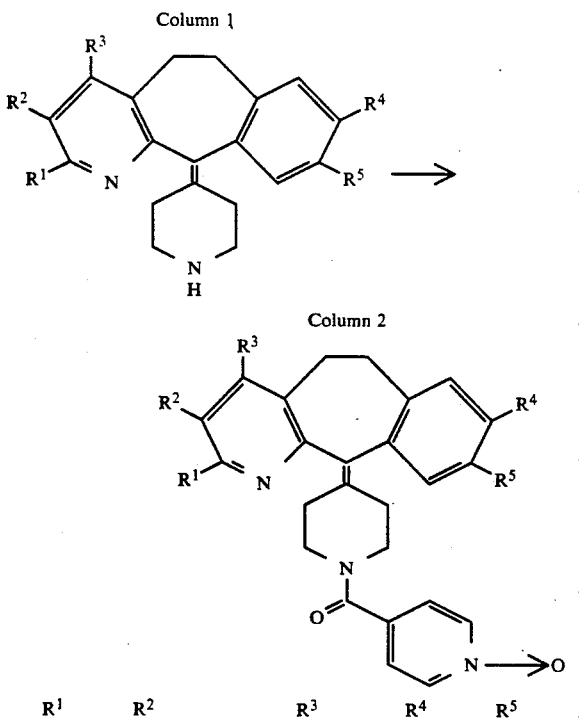

| R¹ | R² | R³ | R⁴ | R⁵ |
|---|---|---|---|---|
| CH₃ | H | H | Cl | H |
| H | t-butyl- | H | Cl | H |
| H | CH₃C(OH)— | H | Cl | H |
| H | H | CH₃ | Cl | H |
| Cl | H | H | Cl | H |
| H | Cl | H | Cl | H |
| H | H | H | Cl | H |
| H | Br | H | Cl | H |
| HO | H | H | Cl | H |
| H | H | OCH₃ | Cl | H |
| H | H | H | H | Cl |
| H | H | H | F | F |
| H | H | H | CH₃ | H |

EXAMPLE 3

By employing essentially the same procedure set forth in Example 1 above but using the amines set forth in column 1 below in place of 4-(8-chloro-5,6-dihydro-11H-benzo[5,6]cyclohepta[1,2-b]pyridin-11-ylidene)-piperidine, one can obtain the compounds listed in column 2 of TABLE 7 below:

TABLE 7

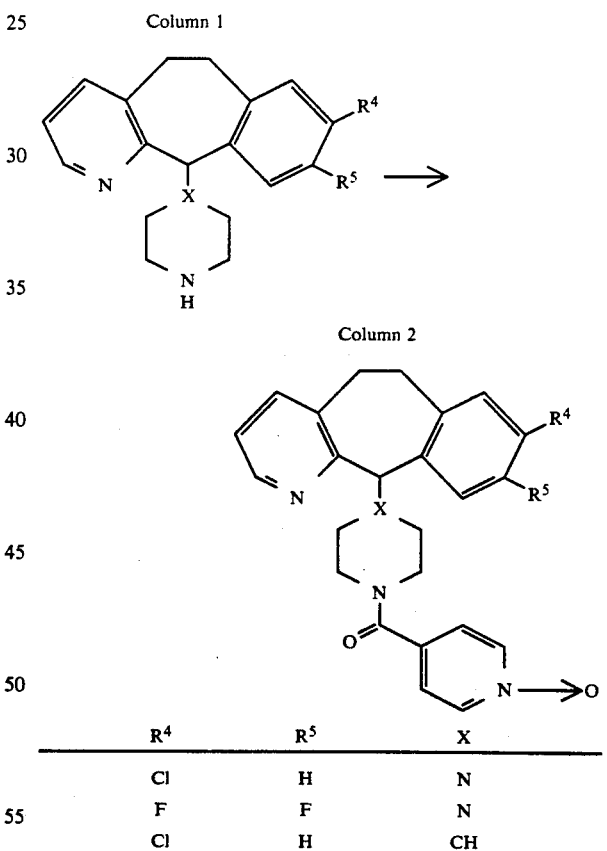

| R⁴ | R⁵ | X |
|---|---|---|
| Cl | H | N |
| F | F | N |
| Cl | H | CH |

EXAMPLE 4

By employing essentially the same procedure set forth in Example 1 above but using the amines set forth in column 1 below in place of 4-(8-chloro-5,6-dihydro-11H-benzo[5,6]cyclohepta[1,2-b]pyridin-11-ylidene)-piperidine, one can obtain the compounds listed in column 2 of TABLE 8 below:

TABLE 8
| Column 1 | Column 2 |
|---|---|
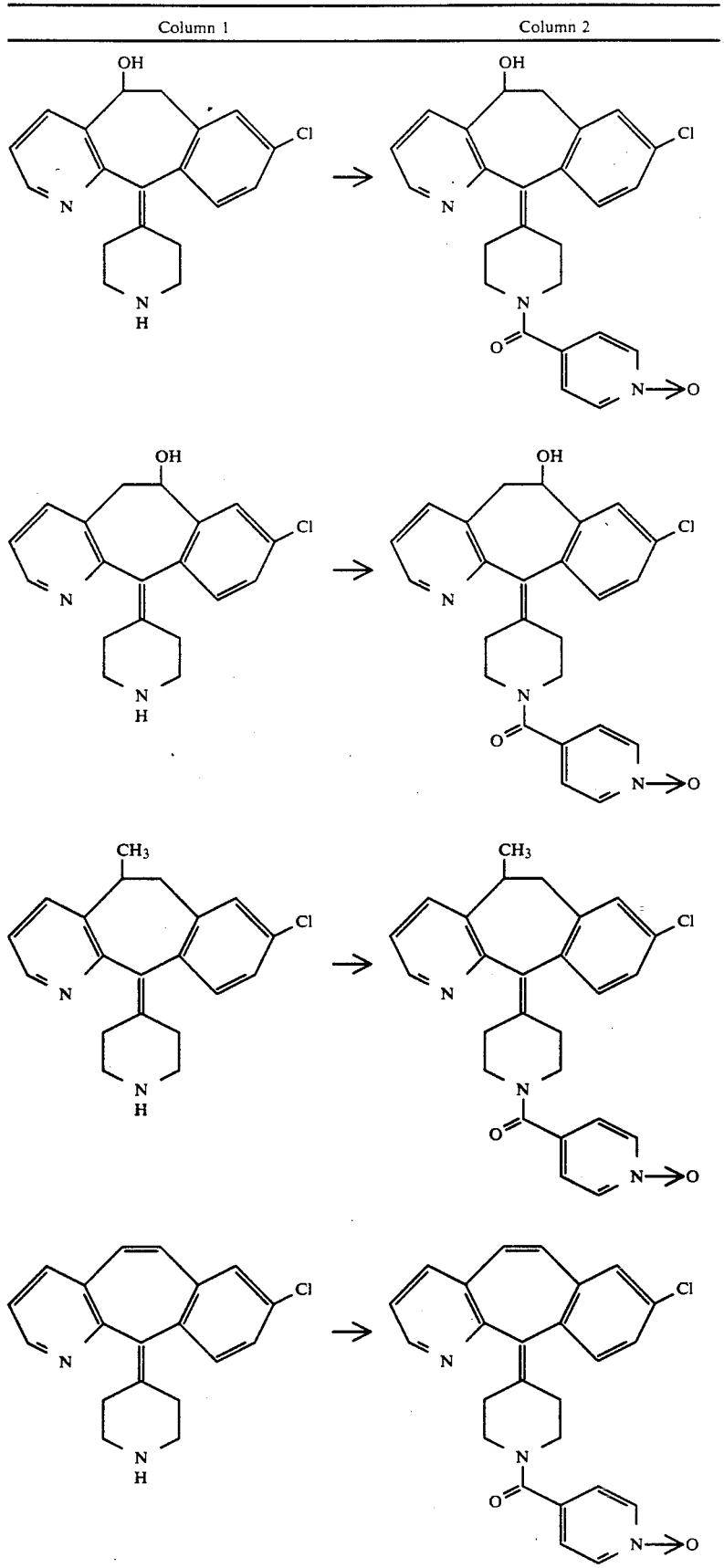

TABLE 8-continued
| Column 1 | Column 2 |
|---|---|
| 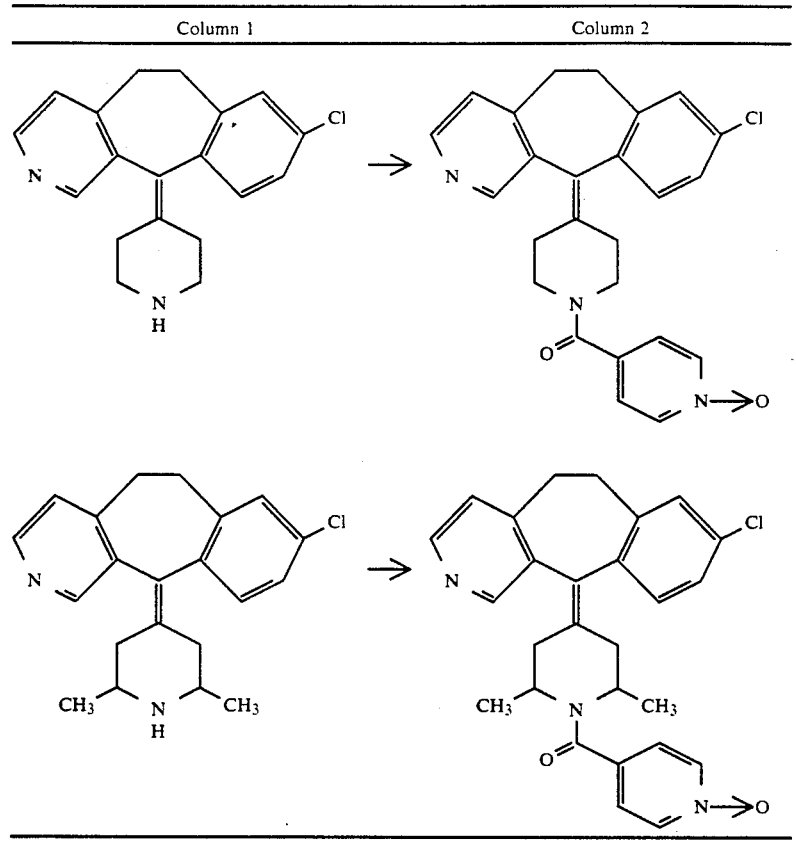 | |
EXAMPLE 5
By employing essentially the same procedure set forth in Example 1 above, but using the carboxlic acids set forth in column 1 below in place of isonicotinamic acid N-oxide, one can obtain the compounds listed in column 2 of TABLE 9 below:
TABLE 9
| Column 1 | Column 2 |
|---|---|
| 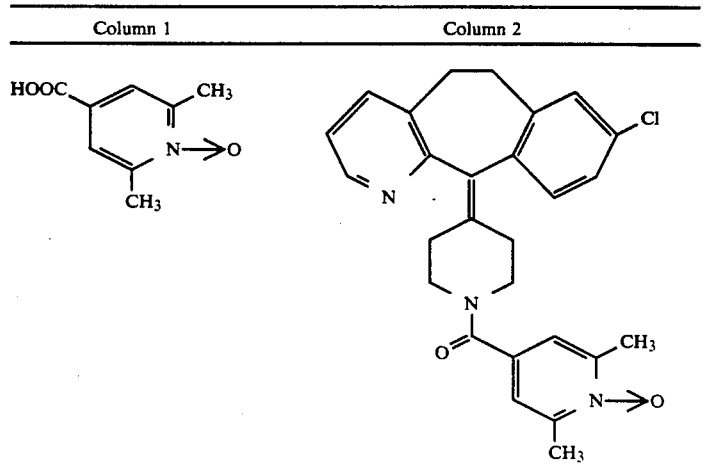 | |

TABLE 9-continued

| Column 1 | Column 2 |
|---|---|
| 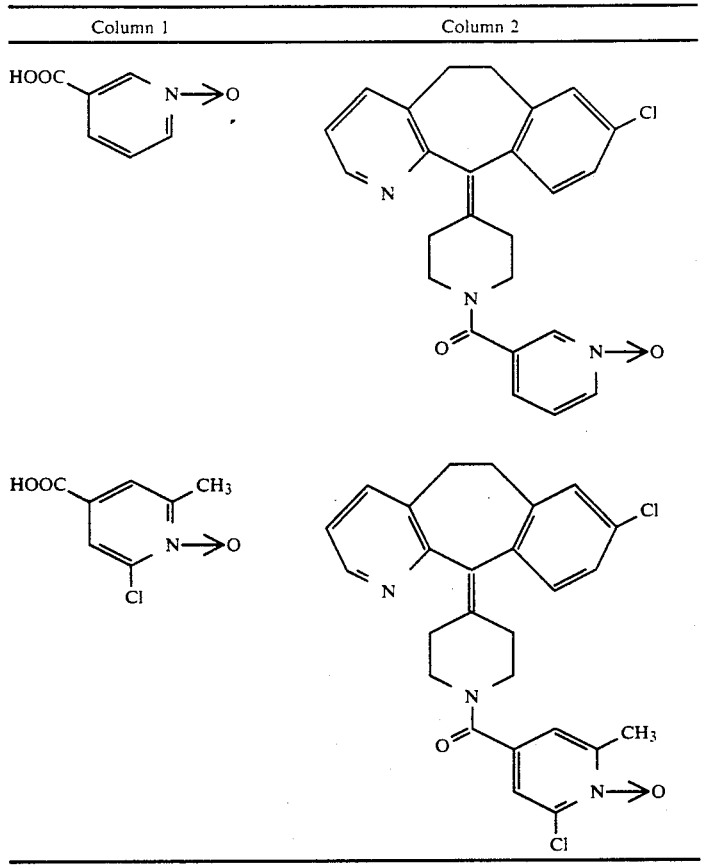 | |

EXAMPLE 6

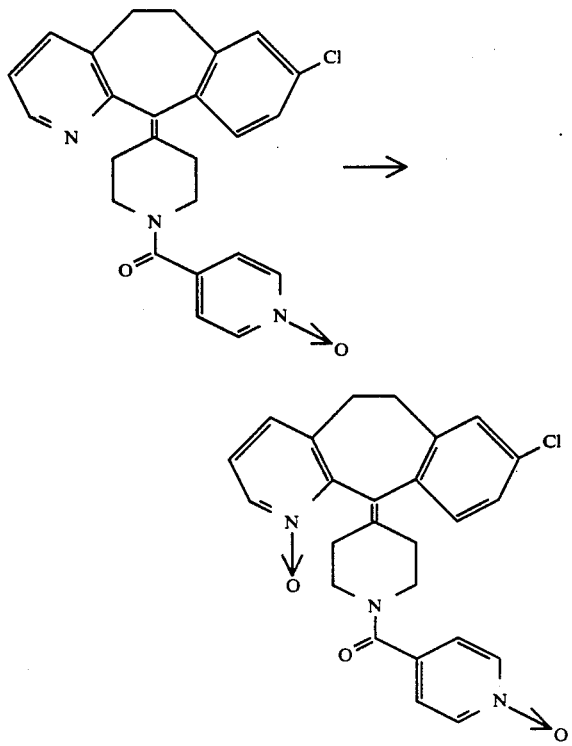

1-(4-PYRIDINYLCARBONYL)-4-(8-CHLORO-5,6-DIHYDRO-11H-BENZO[5,6]CYCLOHEPTA[1,2-b]PYRIDIN-11-YLIDENE)PIPERIDINE $N^1,N^4$-DIOXIDE

To a mixture of 1.35 grams of the title compound from Example 1 above in 15 ml of dry methylene chloride at −15° C. in under an atmosphere of nitrogen was added in several portions over a period of three and one half hours 649 mg of 3-chloroperoxybenzoic acid. The mixture was allowed to come to room temperature and stir over night. The reaction mixture was then poured into a solution of 10% sodium bisulfite and extracted with methylene chloride. The combined organic portions were washed with 1.0M sodium hydroxide, dried over magnesium sulfate, filtered and concentrated in vacuo. The product was then purified via flash chromatography (20% methanol saturated with ammonia in ethyl acetate) and the appropriate fractions combined and recrystallized from ethyl acetate/methanol/isopropyl ether to give 707 mg (51%) of 1-(4-pyridinylcarbonyl)-4-(8-chloro-5,6-dihydro-11H-benzo[5,6]cyclohepta[1,2-b]pyridin-11-ylidene)piperidine $N^1,N^4$-dioxide as a white powder.

EXAMPLE 7

1-(3-PYRIDINYLCARBONYL)-4-(8-CHLORO-5,6-DIHYDRO-11H-BENZO[5,6]CYCLOHEPTA[1,2-B]PYRIDIN-11-YLIDENE)PIPERIDINE $N^1,N^4$-DIOXIDE

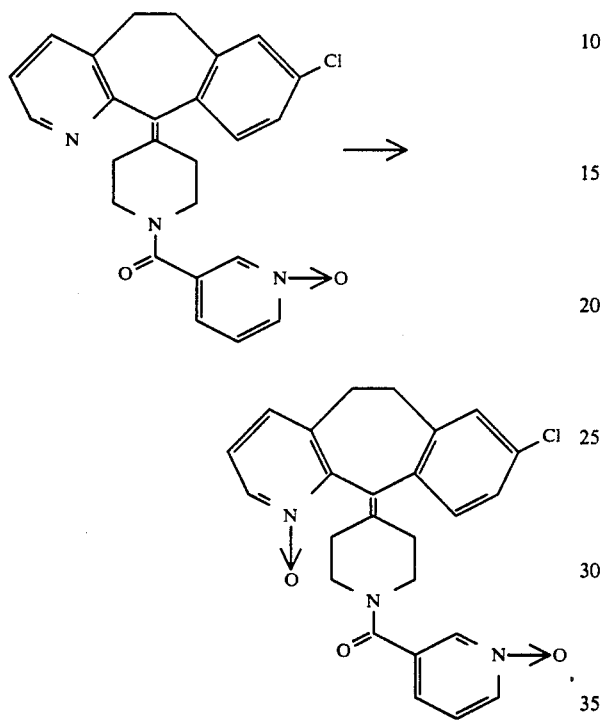

By employing essentially the same procedure as set forth in Example 6 above, but using 1-(3-pyridinylcarbonyl)-4-(8-chloro-5,6-dihydro-11H-benzo[5,6]cyclohepta[1,2-b]pyridin-11-ylidene)piperidine $N^1$-oxide in place of 1-(4-pyridinylcarbonyl)-4-(8-chloro-5,6-dihydro-11H-benzo[5,6]cyclohepta[1,2-b]pyridin-11-ylidene)piperidine $N^1$oxide, one can obtain 1-(3-pyridinylcarbonyl)-4-(8-chloro-5,6-dihydro-11H-benzo[5,6]cyclohepta[1,2-b]pyridin-11-ylidene)piperidine $N^1,N^4$-dioxide.

The following are examples of pharmaceutical dosage forms which contain a compound of the invention. As used therein, the term "active compound" is used to designate the compound

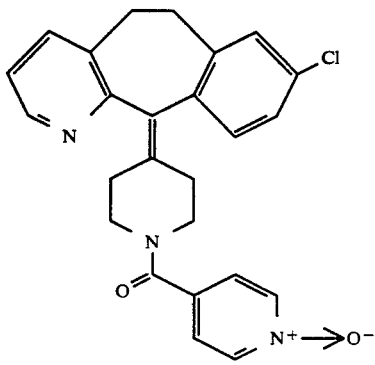

EXAMPLE 8

4-[8-CHLORO-5,6-DIHYDRO-3-METHYL-11H-BENZO[5,6]CYCLOHEPTA[1,2-B]PYRIDIN-11-YLIDENE]-1-(4-PYRIDINYL CARBONYL)PIPERIDINE $N^1$-OXIDE

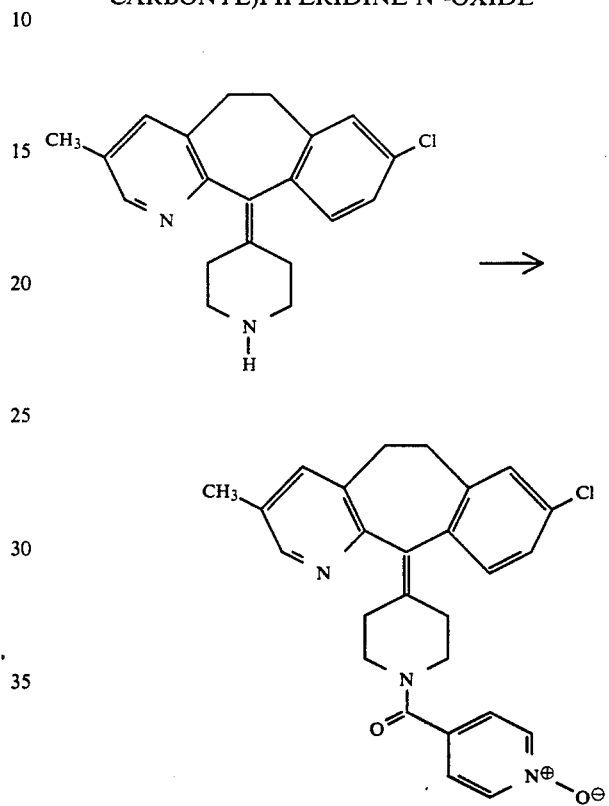

To a mixture of 20 g of 8-chloro-11-(4-piperidylidene)-6,11-dihydro-3-methyl-5H-benzo[5,6-]cyclohepta[1,2-b]pyridine (product from Preparative Example 7, Step E), 1.39 g of isonicotinic acid N-oxide, and 1.35 g of 1-hydroxybenzotriazole in 60 mL CH$_2$Cl$_2$ at 0° C. was added 1.91 g of 1-(3-dimethylaminopropyl)-3-ethyl carbodiimide hydrochloride (DEC). The reaction mixture was slowly allowed to warm to room temperature overnight. The reaction mixture was quenched with water, basified with 10% NaOH, and extracted with CH$_2$Cl$_2$. The combined organic portions were washed with brine, dried over Na$_2$SO$_4$, and concentrated in vacuo. The product was flash chromatographed using 5% methanol in methylene chloride to give 2.52 g of a product which could be triturated with CH$_2$Cl$_2$/diisopropylether (1:20 parts by volume) to give the title compound as a white solid.

EXAMPLE 9

4-[8-CHLORO-5,6-DIHYDRO-3-METHYL-11H-BENZO[5,6]CYCLOHEPTA[1,2-B]PYRIDIN-11-YLIDENE]-1-(4-PYRIDINYLCARBONYL)-PIPERIDINE N¹-OXIDE

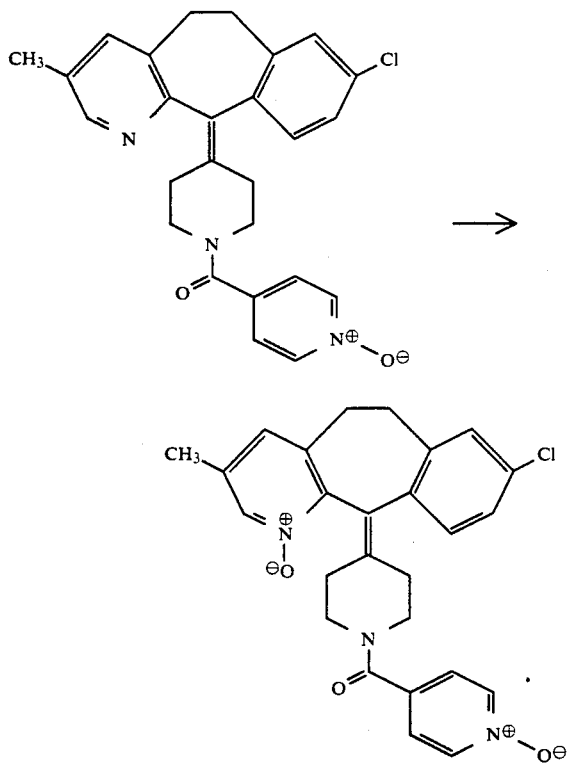

To a solution of 900 mg of the title compound of Example 8 above in 25 mL dry CH$_2$Cl$_2$ at 0° C. was added 700 mg of m-chloroperoxybenzoic acid in 4 portions 15 minutes apart. The reaction was then continued to stir for 1 hr. The mixture was taken up in CH$_2$Cl$_2$, washed with 10% NaHSO$_3$ solution, with 1.0N sodium hydroxide solution and with brine. It was then dried (Na$_2$SO$_4$) and filtered. The solvent was removed under vacuum with a rotavap to give 950 mg of a white foam which was chromatographed with SiO$_2$ (230–400 mesh, 10% methanol saturated with ammonia in ethyl acetate) to give 689 mg of the title compound as a white glass.

The scope of the invention in its pharmaceutical composition aspect is not to be limited by the examples provided, since any other compound of structural formula I can be substituted into the pharmaceutical composition examples.

Pharmaceutical Dosage Form Examples

EXAMPLE A

| No. | Ingredients | Tablets mg/tablet | mg/tablet |
|---|---|---|---|
| 1. | Active compound | 100 | 500 |
| 2. | Lactose USP | 122 | 113 |
| 3. | Corn Starch, Food Grade. as a 10% paste in Purified Water | 30 | 40 |
| 4. | Corn Starch, Food Grade | 45 | 40 |
| 5. | Magnesium Stearate | 3 | 7 |

| No. | Ingredients | Tablets mg/tablet | mg/tablet |
|---|---|---|---|
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

| No. | Ingredient | Capsules mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the structural formula

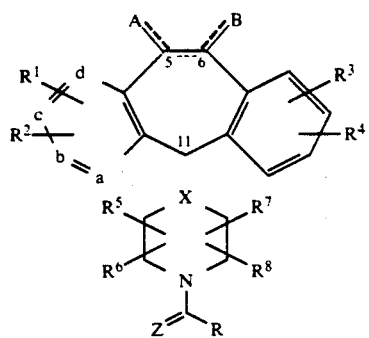

or a pharmaceutically acceptable salt or solvate thereof, wherein:

R represents an N-oxide heterocyclic group of the formula (i), (ii), (iii) or (iv)

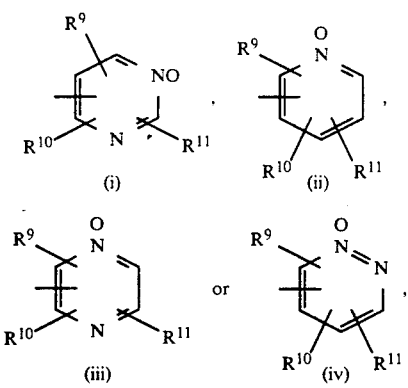

or R represents an alkyl group substituted with a heterocyclic N-oxide group of the formula (i), (ii), (iii) or (iv) above;

one of a, b, c and d represents N or $NR^{12}$ where $R^{12}$ is O, $-CH_3$ or $-(CH_2)_nCO_2H$ where n is 1 to 3, and the remaining a, b, c and d groups are CH, which remaining a, b, c and d groups optionally may be substituted with $R^1$ or $R^2$;

$R^1$ and $R^2$ may be the same or different and each independently represents halo, $-CF_3$, $-OR^{13}$, $-COR^{13}$, $-SR^{13}$, $-S(O)_eR^{14}$ where e is 1 or 2, $-N(R^{13})_2$, $-NO_2$, $-OC(O)R^{13}$, $-CO_2R^{13}$, $-OCO_2R^{14}$, $-CN$, $-NR^{13}OC(O)R^{13}$, alkynyl, alkenyl or alkyl, which alkyl group may be substituted with halo, $-OR^{13}$ or $-CO_2R^{13}$ and which alkenyl group may be substituted with halo, $-OR^{14}$ or $-CO_2R^{13}$;

$R^3$ and $R^4$ may be the same or different and each independently represents H or any of the substituents of $R^1$ and $R^2$, or $R^3$ and $R^4$ together may represent a saturated or unsaturated $C_5-C_7$ carbocyclic ring fused to the benzene ring;

$R^5$, $R^6$, $R^7$ and $R^8$ each independently represent H, $-CF_3$, alkyl or aryl, which alkyl or aryl may be substituted with $-OR^{13}$, $-SR^{13}$, or $-N(R^{13})_2$;

in addition, $R^5$ may be combined with $R^6$ to represent =O or =S and/or $R^7$ may be combined with $R^8$ to represent =O or =S;

$R^9$, $R^{10}$, and $R^{11}$ may be the same or different and each is independently selected from H, halo, $-CF_3$, $-OR^{13}$, $-C(O)R^{13}$, $-SR^{13}$, $-S(O)_eR^{14}$ where e is 1 or 2, $-N(R^{13})_2$, $-NO_2$, $-CO_2R^{13}$, $-OCO_2R^{14}$, $-OCOR^{13}$, alkyl, aryl, alkenyl or alkynyl, which alkyl or alkenyl may be substituted with $-OR^{13}$, $-SR^{13}$ or $-N(R^{13})_2$ and which alkenyl may be substituted with $OR^{14}$ or $SR^{14}$;

$R^{13}$ represents H, alkyl or aryl;

$R^{14}$ represents alkyl or aryl;

$R^{15}$ represents H or alkyl;

X represents N, CH or C;

when X represents C, an optional double bond indicated by the dotted lines to carbon atom 11 is present, and when X is N or CH, the double bond is absent;

the dotted line between carbon atoms 5 and 6 represents an optional double bond, such that when a double bond is present, A and B each independently represent $-R^{13}$, halo, $-OR^{14}$, $-OC(O)R^{13}$ or $-OCO_2R^{14}$ and when no double bond is present between carbon atoms 5 and 6, A and B each independently represent $H_2$, $-(OR^{14})_2$, [H and halo], dihalo, [alkyl and H], (alkyl)$_2$, [—H and —OC(O)$R^{13}$], [H and —$OR^{13}$], =O, [aryl and H], =$NOR^{15}$ or —O—(CH$_2$)$_p$—O— where p is 2, 3 or 4 and $R^{13}$ is as previously defined;

Z represents =O or =S;

alkyl as used herein represents a straight and branched carbon chain containing from one to twenty carbon atoms;

alkenyl as used herein represents a straight and branched carbon chain having at least one carbon to carbon double bond and containing from 2 to 12 carbon atoms;

alkynyl as used herein represents a straight and branched carbon chain having at least one carbon to carbon triple bond and containing from 2 to 12 carbon atoms; and aryl as used herein represents a carbocyclic group containing from 6 to 15 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, $CF_3$, amino, alkylamino, dialkylamino, $-COOR^{15}$ or $-NO_2$.

2. A compound of claim 1 wherein the double bond between carbon atoms 5 and 6 is absent.

3. A compound of claim 1 wherein the double bond between carbons atoms 5 and 6 is present.

4. A compound of claim 1 wherein $R^5$ and $R^6$ are H and $R^7$ and $R^8$ each independently represents H or alkyl.

5. A compound of claim 4 wherein $R^1$ and $R^2$ each independently represents H, alkyl, $OR^{13}$, $NR^{13}_2$ or halo.

6. A compound of claim 5 wherein $R^3$ and $R^4$ each independently represents H, alkyl, $OR^{13}$, $NR^{13}_2$ or halo.

7. A compound of claim 6 wherein X represents C and the dotted line thereto is a double bond.

8. A compound of claims 6 wherein X represents CH and the double bond indicated by the dotted lines thereto is absent.

9. A compound of claim 6 wherein X represents N and the double bond indicated by the dotted lines thereto is absent.

10. A compound of claim 6 wherein Z represents O.

11. A compound of claim 10 wherein R represents

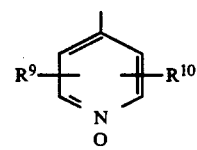

wherein each of $R^9$ and $R^{10}$ independently represents H, alkyl, halo, $OR^{13}$ or $N(R^{13})_2$.

12. A compound of claim 10 wherein R represents

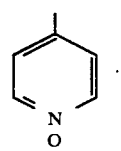

13. A compound having the structural formula

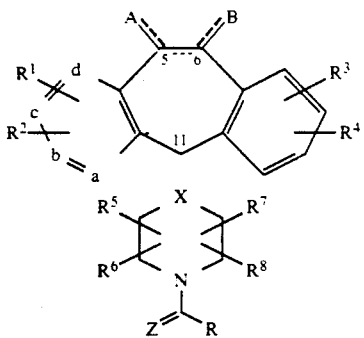

or a pharmaceutically acceptable salt or solvate thereof, wherein:

R represents an N-oxide heterocyclic group of the formula (ia), (iia), (iiia) or (iva):

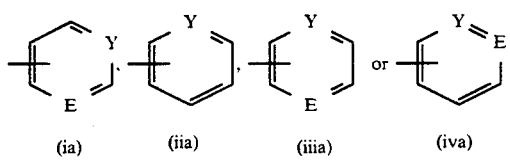

wherein Y represents $N^+$—$O^-$ and E represents $N^+$—$O^-$ or N, or R represents an alkyl group substituted with one of said N-oxide heterocyclic groups (ia), (iia), (iiia) or (iva);

one of a, b, c and d represents N or $NR^{12}$ where $R^{12}$ is O, —$CH_3$ or —$(CH_2)_nCO_2H$ where n is 1 to 3, and the remaining a, b, c and d groups are CH, which remaining a, b, c and d groups optionally may be substituted with $R^1$ or $R^2$;

$R^1$ and $R^2$ may be the same or different and each independently represents halo, —$CF_3$, —$OR^{13}$, —$COR^{13}$, —$SR^{13}$, —$S(O)_eR^{14}$ where e is 1 or 2, —$N(R^{13})_2$, —$NO_2$, —$OC(O)R^{13}$, —$CO_2R^{13}$, —$OCO_2R^{14}$, —CN, —$NR^{13}OC(O)R^{13}$, alkynyl, alkenyl or alkyl, which alkyl group may be substituted with halo, —$OR^{13}$ or —$CO_2R^{13}$ and which alkenyl group may be substituted with halo, —$OR^{14}$ or —$CO_2R^{13}$;

$R^3$ and $R^4$ may be the same or different and each independently represents H or any of the substituents of $R^1$ and $R^2$, or $R^3$ and $R^4$ together may represent a saturated or unsaturated $C_5$-$C_7$ carbocyclic ring fused to the benzene ring;

$R^5$, $R^6$, $R^7$ and $R^8$ each independently represent H, —$CF_3$, alkyl or aryl, which alkyl or aryl may be substituted with —$OR^{13}$, —$SR^{13}$, or —$N(R^{13})_2$;

in addition, $R^5$ may be combined with $R^6$ to represent =O or =S and/or $R^7$ may be combined with $R^8$ to represent =O or =S;

$R^9$, $R^{10}$, and $R^{11}$ may be the same or different and each is independently selected from H, halo, —$CF_3$, —$OR^{13}$, —$C(O)R^{13}$, —$SR^{13}$, —$S(O)_eR^{14}$ where e is 1 or 2, —$N(R^{13})_2$, —$NO_2$, —$CO_2R^{13}$, —$OCO_2R^{14}$, —$OCOR^{13}$, alkyl, aryl, alkenyl or alkynyl, which alkyl or alkenyl may be substituted with —$OR^{13}$, —$SR^{13}$ or —$N(R^{13})_2$ and which alkenyl may be substituted with $OR^{14}$ or $SR^{14}$;

$R^{13}$ represents H, alkyl or aryl;
$R^{14}$ represents alkyl or aryl;
$R^{15}$ represents H or alkyl;

X represents N, CH or C;

when X represents C, an optional double bond indicated by the dotted lines to carbon atom 11 is present, and when X is N or CH, the double bond is absent;

the dotted line between carbon atoms 5 and 6 represents an optional double bond, such that when a double bond is present, A and B each independently represent —$R^{13}$, halo, —$OR^{14}$, —OC(O)$R^{13}$ or —$OCO_2R^{14}$ and when no double bond is present between carbon atoms 5 and 6, A and B each independently represent $H_2$, —$(OR^{14})_2$, [H and halo], dihalo, [alkyl and H], (alkyl)$_2$, [—H and —OC(O)$R^{13}$], [H and —$OR^{13}$], =O, [aryl and H], =$NOR^{15}$ or —O—$(CH_2)_p$—O— where p is 2, 3 or 4 and $R^{13}$ is as previously defined; and Z represents =O or =S;

alkyl as used herein represents a straight and branched carbon chain containing from one to twenty carbon atoms;

alkenyl as used herein represents a straight and branched carbon chain having at least one carbon to carbon double bond and containing from 2 to 12 carbon atoms;

alkynyl as used herein represents a straight and branched carbon chain having at least one carbon to carbon triple bond and containing from 2 to 12 carbon atoms; and aryl as used herein represents a carbocyclic group containing from 6 to 15 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, $CF_3$, amino, alkylamino, dialkylamino, —$COOR^{15}$ or —$NO_2$.

14. A compound of claim 13 having the stuctural formula Ib:

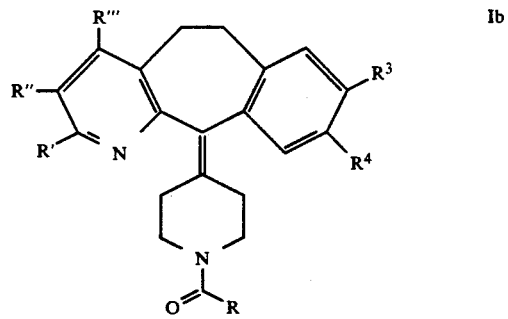

where at least one of R', R" and R''' is other than H and each independently represents halo, phenyl, substituted phenyl, hydroxy, mercapto, alkyl of 2 to 6 carbon atoms, alkyl—C(O)—, alkyl substituted with a hydroxy or $CF_3$; $R^3$ and $R^4$ are the same or different and are as defined in claim 13; and R represents a heterocyclic group of formula (ia), (iia), (iiia) or (iva).

15. A compound of claim 14 which is selected from:
4-(8-chloro-5,6-dihydro-11H-benzo[5,6]cyclohepta[1,2-b]pyridin-11-ylidene)-1-(3-pyridinyl carbonyl)piperidine $N^1$-oxide;
4-(8-chloro-5,6-dihydro-11H-benzo[5,6]cyclohepta[1,2-b]pyridin-11-ylidene)-1-(3-pyridinylcarbonyl)piperidine $N^1$, $N^4$-dioxide;

4-(8-chloro-5,6-dihydro-11H-benzo[5,6]cyclohepta[1,2-b]pyridin-11-ylidene)-1-(4-pyridinyl carbonyl)piperidine N¹-oxide, i.e.,

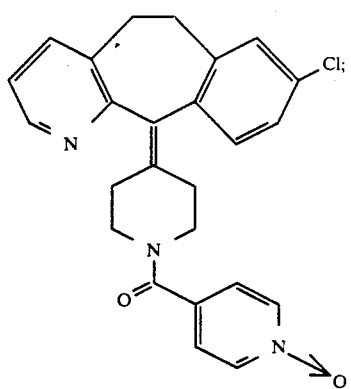

and
4-(8-chloro-5,6-dihydro-11H-benzo[5,6]cyclohepta[1,2-b]pyridin-11-ylidene)-1-(4-pyridinylcarbonyl)piperidine N¹, N⁴-dioxide.

16. A compound of claim 14 which is:
4-(8-chloro-5,6-dihydro-11H-benzo[5,6]cyclohepta[1,2-b]pyridin-11-ylidene)-1-(4-pyridinyl carbonyl)piperidine N¹-oxide; or
4-(8-chloro-5,6-dihydro-11H-benzo[5,6]cyclohepta[1,2-b]pyridin-11-ylidene)-1-(4-pyridinylcarbonyl)piperidine N¹,N⁴-dioxide.

17. A compound of claim 1 having the structural formula

Ic

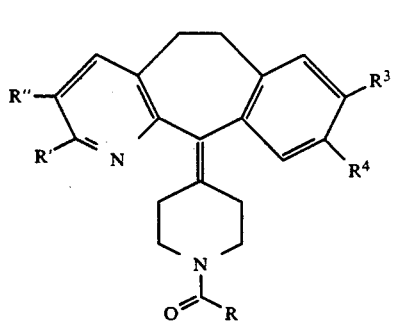

where R' and R" are independently H, halo, alkyl, OH or CF₃; R³ and R⁴ are the same or different and are as defined in claim 1; and R represents a heterocyclic N-oxide group of the formula (i), (ii), (iii) or (iv).

18. A compound of claim 1 which is:

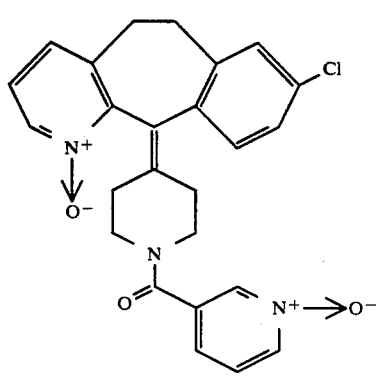

-continued

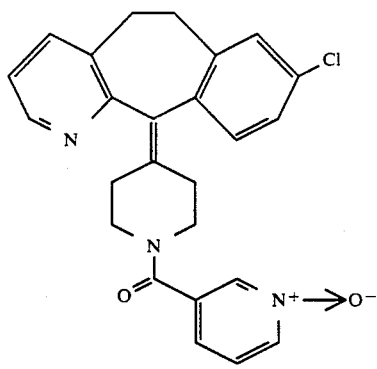

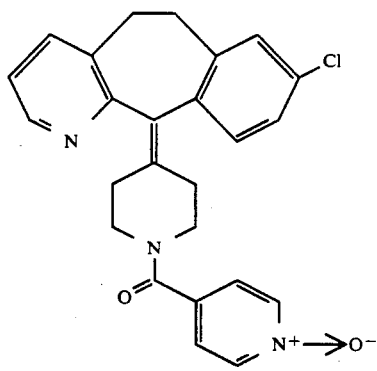

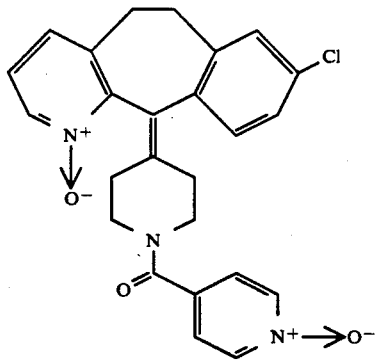

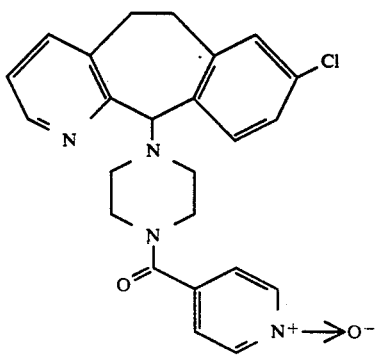

-continued
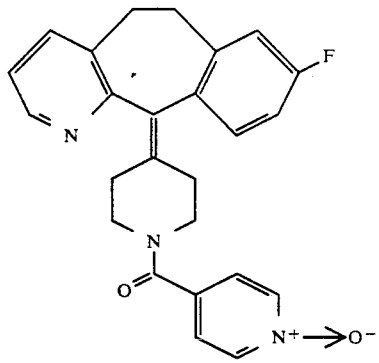
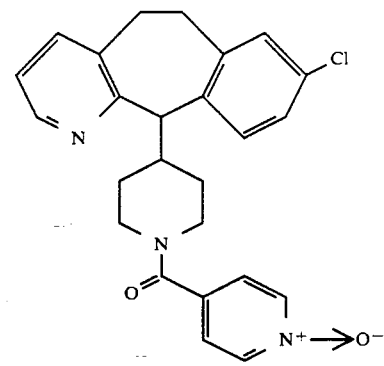
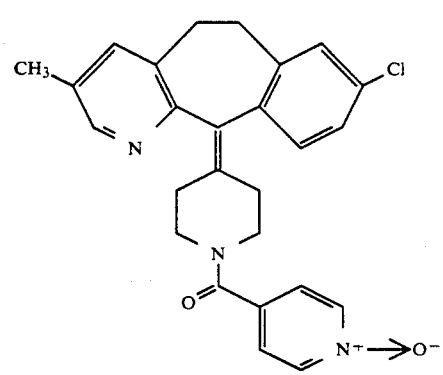
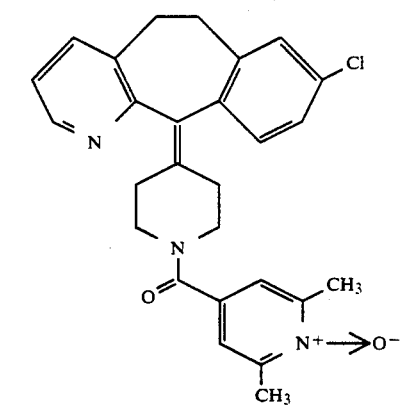
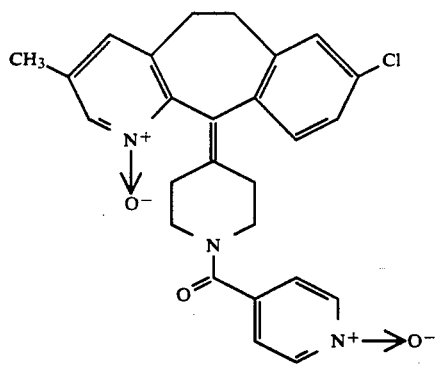
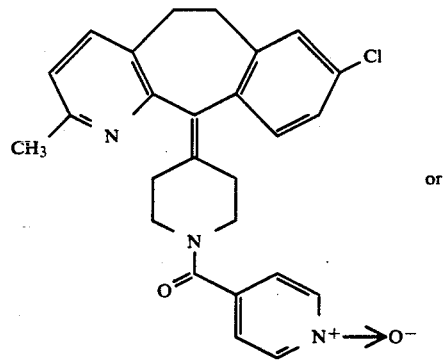
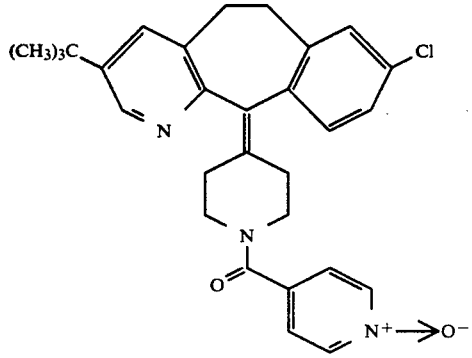
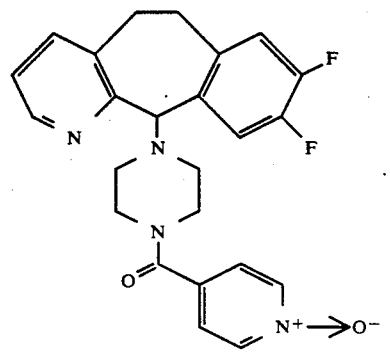
or
19. A compound having the structural formula:

-continued

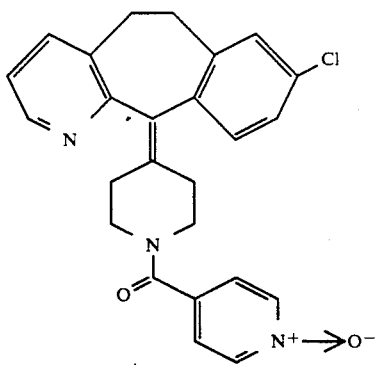

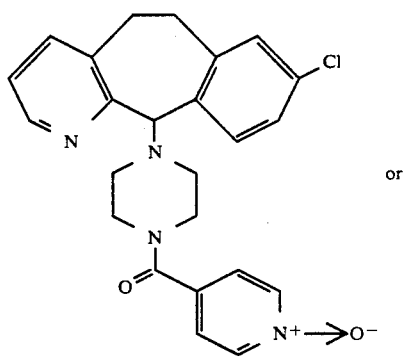

or

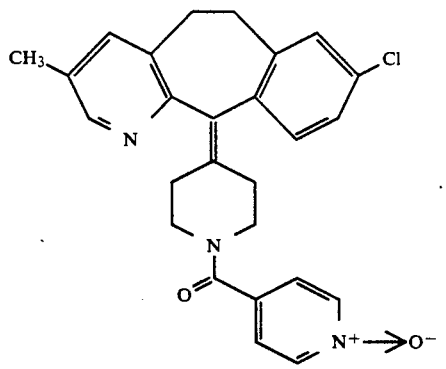

19. A compound having the structural formula:

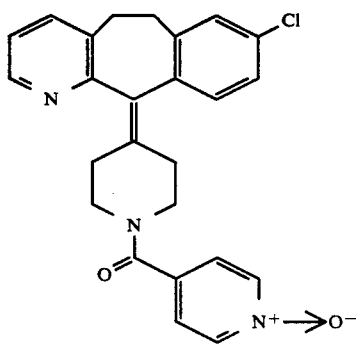

-continued

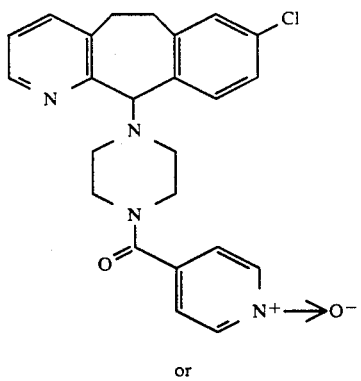

or

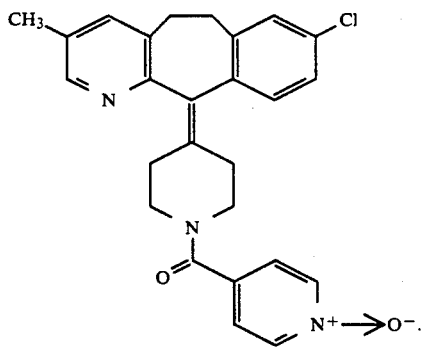

20. A pharmaceutical composition for treating allergy or inflammation comprising an effective amount of a compound of formula I as defined in claim 1 in combination with a pharmaceutically acceptable carrier.

21. A method of treating allergy comprising administering a compound of formula I as defined in claim 1 to a mammal in need of such treatment in an amount effective to treat allergy.

22. A method of treating inflammation comprising administering to a mammal in need of such treatment an antiinflammatory effective amount of a compound of formula I as defined in claim 1.

23. A pharmaceutical composition for treating allergy or inflammation comprising an effective amount of a compound of formula I as defined in claim 14 in combination with a pharmaceutically acceptable carrier.

24. A method of treating allergy comprising administering a compound of formula I as defined in claim 14 to a mammal in need of such treatment in an amount effective to treat allergy.

25. A method of treating inflammation comprising administering to a mammal in need of such treatment an antiinflammatory effective amount of a compound of formula I as defined in claim 14.

26. A pharmaceutical composition for treating allergy or inflammation comprising an effective amount of a compound of formula I as defined in claim 18 in combination with a pharmaceutically acceptable carrier.

27. A method of treating allergy comprising administering a compound of formula I as defined in claim 18 to a mammal in need of such treatment in an amount effective to treat allergy.

28. A method of treating inflammation comprising administering to a mammal in need of such treatment an antiinflammatory effective amount of a compound of formula I as defined in claim 18.

29. A compound having the structural formula

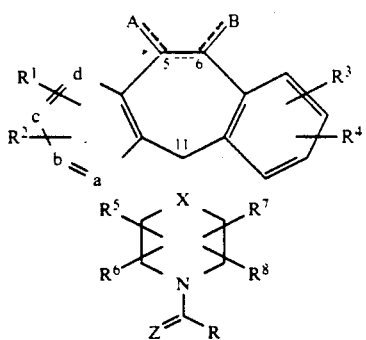

I or a pharmaceutically acceptable salt or solvate thereof, wherein:

R represents an N-oxide heterocyclic group of the formula (i), (ii), (iii) or (iv)

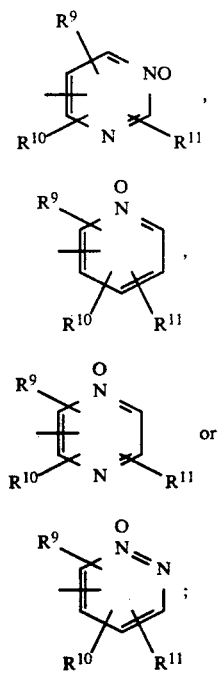

one of a, b, c and d represents N or $NR^{12}$ where $R^{12}$ is O, $-CH_3$ or $-(CH_2)_nCO_2H$ where n is 1 to 3, and the remaining a, b, c and d groups are CH, which remaining a, b, c and d groups optionally may be substituted with $R^1$ or $R^2$;

$R^1$ and $R^2$ may be the same or different and each independently represents halo, $-CF_3$, $-OR^{13}$, $-COR^{13}$, $-SR^{13}$, $-S(O)_eR^{14}$ where e is 1 or 2, $-N(R^{13})_2$, $-NO_2$, $-OC(O)R^{13}$, $-CO_2R^{13}$, $-O-CO_2R^{14}$, $-CN$, $-NR^{13}OC(O)R^{13}$, alkynyl, alkenyl or alkyl, which alkyl group may be substituted with halo, $-OR^{13}$ or $-CO_2R^{13}$ and which alkenyl group may be substituted with halo, $-OR^{14}$ or $-CO_2R^{13}$;

$R^3$ and $R^4$ may be the same or different and each independently represents H or any of the substituents of $R^1$ and $R^2$, or $R^3$ and $R^4$ together may represent a saturated or unsaturated $C_5$-$C_7$ carbocyclic ring fused to the benzene ring;

$R^5$, $R^6$, $R^7$ and $R^8$ each independently represent H, $-CF_3$, alkyl or aryl, which alkyl or aryl may be substituted with $-OR^{13}$, $-SR^{13}$, or $-N(R^{13})_2$;

in addition, $R^5$ may be combined with $R^6$ to represent $=O$ or $=S$ and/or $R^7$ may be combined with $R^8$ to represent $=O$ or $=S$;

$R^9$, $R^{10}$, and $R^{11}$ may be the same or different and each is independently selected from H, halo, $-CF_3$, $-OR^{13}$, $-C(O)R^{13}$, $-SR^{13}$, $-S(O)_eR^{14}$ where e is 1 or 2, $-N(R^{13})_2$, $-NO_2$, $-CO_2R^{13}$, $-OCO_2R^{14}$, $-OCOR^{13}$, alkyl, aryl, alkenyl or alkynyl, which alkyl or alkenyl may be substituted with $-OR^{13}$, $-SR^{13}$ or $-N(R^{13})_2$ and which alkenyl may be substituted with $OR^{14}$ or $SR^{14}$;

$R^{13}$ represents H, alkyl or aryl;

$R^{14}$ represents alkyl or aryl;

$R^{15}$ represents H or alkyl;

X represents N, CH or C;

when X represents C, an optional double bond indicated by the dotted lines to carbon atom 11 is present, and when X is N or CH, the double bond is absent;

the dotted line between carbon atoms 5 and 6 represents an optional double bond, such that when a double bond is present, A and B each independently represent $-R^{13}$, halo, $-OR^{14}$, $-OC(O)R^{13}$ or $-OCO_2R^{14}$ and when no double bond is present between carbon atoms 5 and 6, A and B each independently represent $H_2$, $-(OR^{14})_2$, [H and halo], dihalo, [alkyl and H], (alkyl)$_2$, [$-H$ and $-OC(O)R^{13}$], [H and $-OR^{13}$], $=O$, [aryl and H], $=NOR^{15}$ or $-O-(CH_2)_p-O-$ where p is 2, 3 or 4 and $R^{13}$ is as previously defined;

Z represents $=O$ or $=S$;

alkyl as used herein represents a straight and branched carbon chain containing from one to twenty carbon atoms;

alkenyl as used herein represents a straight and branched carbon chain having at least one carbon to carbon double bond and containing from 2 to 12 carbon atoms;

alkynyl as used herein represents a straight and branched carbon chain having at least one carbon to carbon triple bond and containing from 2 to 12 carbon atoms; and aryl as used herein represents a carbocyclic group containing from 6 to 15 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, $CF_3$, amino, alkylamino, dialkylamino, $-COOR^{15}$ or $-NO_2$.

30. A compound having the structural formula

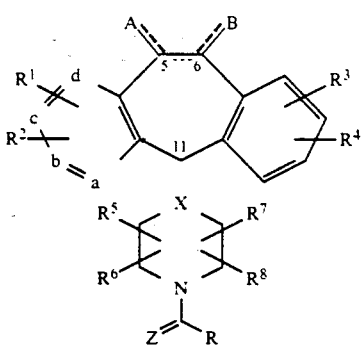

or a pharmaceutically acceptable salt or solvate thereof, wherein:

R represents an N-oxide heterocyclic group of the formula (ia), (iia), (iiia) or (iva):

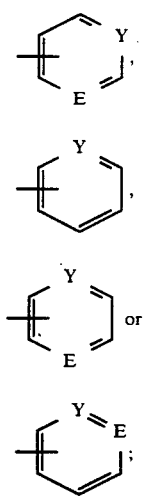

one of a, b, c and d represents N or NR$^{12}$ where R$^{12}$ is O, —CH$_3$ or —(CH$_2$)$_n$CO$_2$H where n is 1 to 3, and the remaining a, b, c and d groups are CH, which remaining a, b, c and d groups optionally may be substituted with R$^1$ or R$^2$;

R$^1$ and R$^2$ may be the same or different and each independently represents halo, —CF$_3$, —OR$^{13}$, —COR$^{13}$, —SR$^{13}$, —S(O)$_e$R$^{14}$ where e is 1 or 2, —N(R$^{13}$)$_2$, —NO$_2$, —OC(O)R$^{13}$, —CO$_2$R$^{13}$, —O-CO$_2$R$^{14}$, —CN, —NR$^{13}$OC(O)R$^{13}$, alkynyl, alkenyl or alkyl, which alkyl group may be substituted with halo, —OR$^{13}$ or —CO$_2$R$^{13}$ and which alkenyl group may be substituted with halo, —OR$^{14}$ or —CO$_2$R$^{13}$;

R$^3$ and R$^4$ may be the same or different and each independently represents H or any of the substituents of R$^1$ and R$^2$, or R$^3$ and R$^4$ together may represent a saturated or unsaturated C$_5$-C$_7$ carbocyclic ring fused to the benzene ring;

R$^5$, R$^6$, R$^7$ and R$^8$ each independently represent H, —CF$_3$, alkyl or aryl, which alkyl or aryl may be substituted with —OR$^{13}$, —SR$^{13}$, or —N(R$^{13}$)$_2$;

in addition, R$^5$ may be combined with R$^6$ to represent =O or =S and/or R$^7$ may be combined with R$^8$ to represent =O or =S and/or R$^7$ may be combined with R$^8$ to represent =O or =S;

R$^9$, R$^{10}$, and R$^{11}$ may be the same or different and each is independently selected from H, halo, —CF$_3$, —OR$^{13}$, —C(O)R$^{13}$, —SR$^{13}$, —S(O)$_e$R$^{14}$ where e is 1 or 2, —N(R$^{13}$)$_2$, —NO$_2$, —CO$_2$R$^{13}$, —OCO$_2$R$^{14}$, —OCOR$^{13}$, alkyl, aryl, alkenyl or alkynyl, which alkyl or alkenyl may be substituted with —OR$^{13}$, —SR$^{13}$ or —N(R$^{13}$)$_2$ and which alkenyl may be substituted with OR$^{14}$ or SR$^{14}$;

R$^{13}$ represents H, alkyl or aryl;

R$^{14}$ represents alkyl or aryl;

R$^{15}$ represents H or alkyl;

X represents N, CH or C;

when X represents C, an optional double bond indicated by the dotted lines to carbon atom 11 is present, and when X is N or CH, the double bond is absent;

the dotted line between carbon atoms 5 and 6 represents an optional double bond, such that when a double bond is present, A and B each independently represent —R$^{13}$, halo, —OR$^{14}$, —OC(O)R$^{13}$ or —OCO$_2$R$^{14}$ and when no double bond is present between carbon atoms 5 and 6, A and B each independently represent H$_2$, —(OR$^{14}$)$_2$, [H and halo], dihalo, [alkyl and H], (alkyl)$_2$, [—H and —OC(O)R$^{13}$], [H and —OR$^{13}$], =O, [aryl and H], =NOR$^{15}$ or —O—(CH$_2$)$_p$—O— where p is 2, 3 or 4 and R$^{13}$ is as previously defined; and Z represents =O or =S;

alkyl as used herein represents a straight and branched carbon chain containing from one to twenty carbon atoms;

alkenyl as used herein represents a straight and branched carbon chain having at least one carbon to carbon double bond and containing from 2 to 12 carbon atoms;

alkynyl as used herein represents a straight and branched carbon chain having at least one carbon to carbon triple bond and containing from 2 to 12 carbon atoms; and aryl as used herein represents a carbocyclic group containing from 6 to 15 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, CF$_3$, amino, alkylamino, dialkylamino, —COOR$^{15}$ or —NO$_2$.

31. A compound of the structural formula:

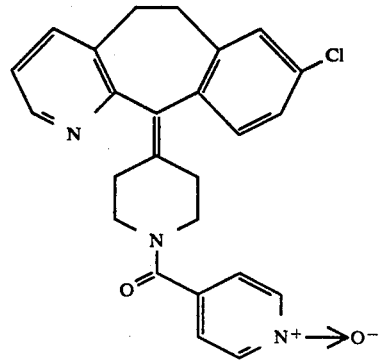

or a pharmaceutically acceptable salt or solvate thereof.

* * * * *

REEXAMINATION CERTIFICATE (2372nd)

United States Patent [19]

Piwinski et al.

[11] B1 5,151,423

[45] Certificate Issued   Aug. 30, 1994

[54] HETEROCYCLIC N-OXIDE DERIVATIVES OF SUBSTITUTED BENZO[5,6]CYCLOHEPTAPYRIDINES, COMPOSITIONS AND METHODS OF USE

[75] Inventors: John J. Piwinski, Parsippany; Michael J. Green, Skillman; Jesse Wong, Union, all of N.J.

[73] Assignee: Schering Corp., Kenilworth, N.J.

Reexamination Request:
No. 90/003,213, Oct. 5, 1993

Reexamination Certificate for:
Patent No.: 5,151,423
Issued: Sep. 29, 1992
Appl. No.: 625,261
Filed: Dec. 10, 1990

Related U.S. Application Data

[63] Continuation of Ser. No. 345,604, May 1, 1989, Pat. No. 5,089,496.

[30] Foreign Application Priority Data

Apr. 30, 1990 [EP]   European Pat. Off. ........ 90108225.5

[51] Int. Cl.$^5$ .................. A61K 31/495; A61K 31/50; C07D 401/04; C07D 221/06

[52] U.S. Cl. .................. 514/254; 514/253; 514/254; 514/256; 514/269; 514/275; 514/290; 544/238; 544/295; 544/298; 544/322; 544/333; 544/361; 544/405; 546/77; 546/93; 546/187; 546/196; 546/202; 546/203

[58] Field of Search .......... 544/361, 295, 298, 238, 544/322, 333, 405; 546/77, 93, 187, 196, 202, 203; 514/253, 254, 269, 275, 256, 290

[56] References Cited

FOREIGN PATENT DOCUMENTS

WO89/10363   11/1989   World Int. Prop. O. .

*Primary Examiner*—Cecilia Tsang

[57] ABSTRACT

Heterocyclic N-oxide derivatives of substituted benzo[5,6]cycloheptapyridines, and pharmaceutically acceptable salts and solvates thereof are disclosed, which possess anti-allergic and anti-inflammatory activity. Methods for preparing and using the compounds are also described.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-12, 17, 19 (second occurrance and one of the two identical claims 19) and 29-30 are cancelled.

Claims 13, 18, 19 (first occurrance) and 20-22 are determined to be patentable as amended.

Claims 14-16, 23-28 and 31, dependent on an amended claim, are determined to be patentable.

13. A compound having the structural formula

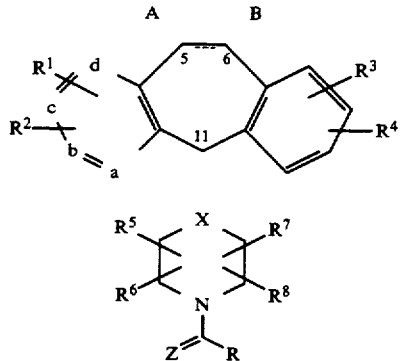

or a pharmaceutically acceptable salt or solvate thereof, wherein:

R represents an N-oxide heterocyclic group of the formula (ia), (iia), (iiia), or (iva):

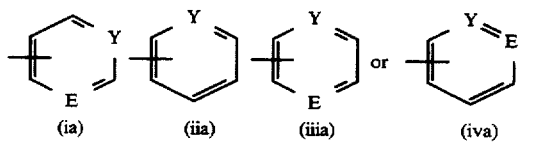

wherein Y represents $N^+-O^-$ and E represents $N^+-O^-$ or N, or R represents an alkyl group substituted with one of said N-oxide heterocyclic groups (ia), (iia), (iiia) or (iva):

one of a, b, c and d represents N or $NR^{12}$ where $R^{12}$ is O, $-CH_3$ or $-(CH_2)_nCO_2H$ where n is 1 to 3, and the remaining a, b, c and d groups are CH, which remaining a, b, c and d groups optionally may be substituted with $R^1$ or $R^2$;

$R^1$ and $R^2$ may be the same or different and each independently represents halo, $-CF_3$, $-OR^{13}$, $-COR^{13}$, $-SR^{13}$, $-S(O)_eR^{14}$ where e is 1 or 2, $-N(R^{13})_2$, $-NO_2$, $-OC(O)R^{13}$, [$-CO_2R^{13}$,] $-OCO_{21}R^{14}$, $-CN$, $-NR^{13}OC(O)R^{13}$, alkynyl, alkenyl or alkyl, which alkyl group may be substituted with halo, $-OR^{13}$ or $-CO_2R^{13}$ and which alkenyl group may be substituted with halo, $-OR^{14}$ or $-CO_2R^{13}$;

$R^3$ and $R^4$ may be the same or different and each independently represents H or any of the substituents of $R^1$ and $R^2$, or $R^3$ and $R^4$ together may represent a saturated or unsaturated $C_5$-$C_7$ carbocyclic ring fused to the benzene ring;

$R^5$, $R^6$, $R^7$ and $R^8$ each independently represent H, $-CF_3$, alkyl or aryl, which alkyl or aryl may be substituted with $-OR^{13}$, $-SR^{13}$, or $-N(R^{13})_2$;

in addition, $R^5$ may be combined with $R^6$ to represent $=O$ or $=S$ and/or $R^7$ may be combined with $R^8$ to represent $=O$ or $=S$;

[$R^9$, $R^{10}$, and $R^{11}$ may be the same or different and each is independently selected from H, halo, $-CF_3$, $-OR^{13}$, $-OR^{13}$, $-C(O)R^{13}$, $-SR^{13}$, $-S(O)_eR^{14}$ where e is 1 or 2, $-N(R^{13})_2$, $-NO_2$, $-CO_2R^{13}$, $-OCO_2R^{14}$, $-OCOR^{13}$, alkyl, aryl, alkenyl or alkynyl, which alkyl or alkenyl may be substituted with $-OR^{13}$, $-SR^{13}$ or $-N(R^{13})_2$ and which alkenyl may be substituted with $OR^{14}$ or $SR^{14}$;]

$R^{13}$ represents H, alkyl or aryl;

$R^{14}$ represents alkyl or aryl;

$R^{15}$ represents H or alkyl;

X represents N, [CH] or C;

when X represents C, an optional double bond indicated by the dotted lines to carbon atom 11 is present, and when X is N [or CH,] the double bond is absent;

the dotted line between carbon atoms 5 and 6 represents an optional double bond, such that when a double bond is present, A and B each independently represent $-R^{13}$, [halo,] $-OR^{14}$, or $-OC(O)R^{13}$ [or $-OCO_2R^{14}$] and when no double bond is present between carbon atoms 5 and 6, A and B each independently represent $H_2$, $-(OR^{14})_2$, [H and halo,] dihalo, [alkyl and H,] (alkyl)$_2$, [$-H$ and $-OC(O)R^{13}$, [H and $-OR^{13}$,] $=O$, [aryl and H,] $=NOR^{15}$ or $-O-(CH_2)_p-O-$ where p is 2, 3 or 4 and $R^{13}$ is as previously defined; and Z represents $=O$ or $=S$;

alkyl as used herein represents a straight and branched carbon chain containing from one to twenty carbon atoms;

alkenyl as used herein represents a straight and branched carbon chain having at least one carbon to carbon double bond and containing from 2 to 12 carbon atoms;

alkynyl as used herein represents a straight and branched carbon chain having at least one carbon to carbon triple bond and containing from 2 to 12 carbon atoms; and aryl as used herein represents a carbocyclic group containing from 6 to 15 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, $CF_3$, amino, alkylamino, dialkylamino, $-COOR^{15}$ or $-NO_2$.

18. A compound of claim [1] *13* which is:

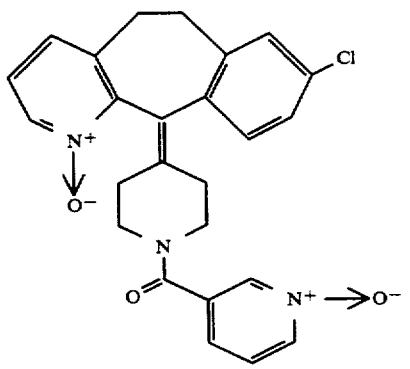
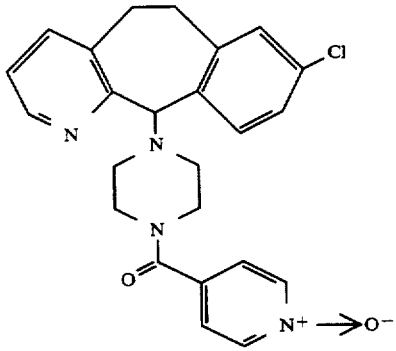
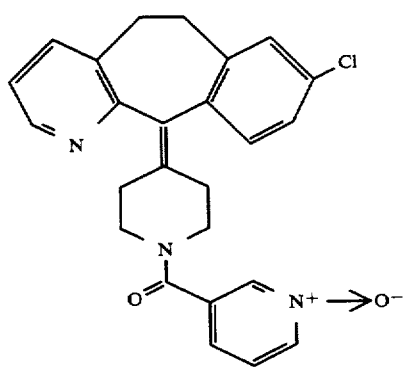
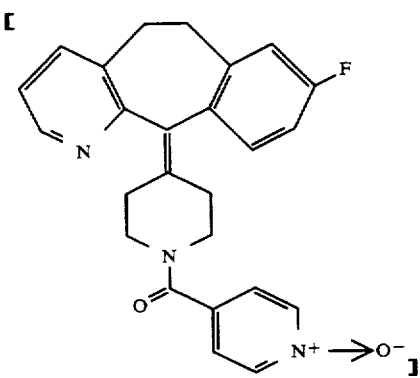
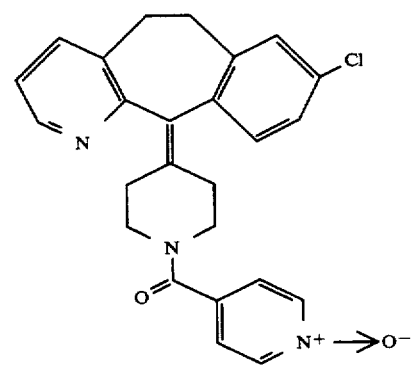
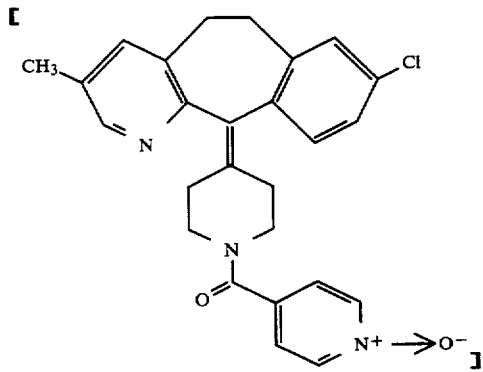
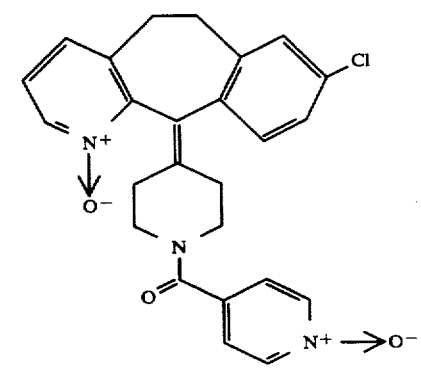
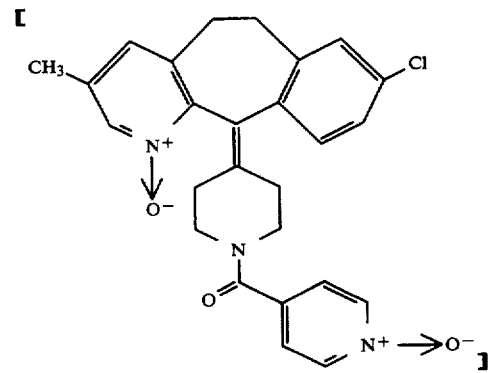

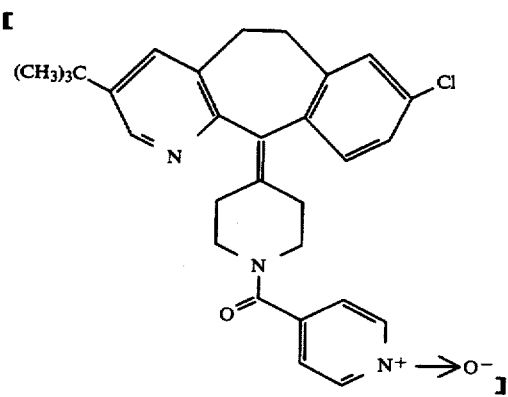
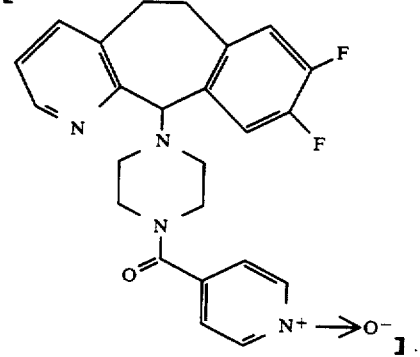
19. A compound having the structural formula:
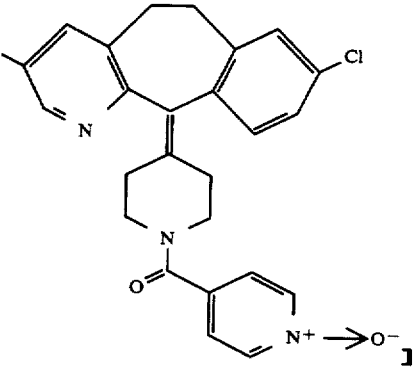
20. A pharmaceutical composition for treating allergy or inflammation comprising an effective amount of a compound of formula I as defined in claim [1] *13* in combination with a pharmaceutically acceptable carrier.
21. A method of treating allergy comprising administering a compound of formula I as defined in claim

[1] 13 to a mammal in need of such treatment in an amount effective to treat allergy.

22. A method of treating inflammation comprising administering to a mammal in need of such treatment an anti-inflammatory effective amount of a compound of formula I as defined in claim [1] 13.

* * * * *